(12) United States Patent
Masko et al.

(10) Patent No.: US 12,280,254 B2
(45) Date of Patent: *Apr. 22, 2025

(54) APPARATUS AND METHOD FOR MICROCURRENT-STIMULATION THERAPY

(71) Applicant: i-Lumen Scientific, Inc., Bloomington, MN (US)

(72) Inventors: Marshall T. Masko, Minnetonka, MN (US); Blair P. Mowery, College Grove, TN (US); John C. Velure, Minnetonka, MN (US); Charles A. Lemaire, Apple Valley, MN (US)

(73) Assignee: i-Lumen Scientific, Inc., Bloomington, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/405,162

(22) Filed: Jan. 5, 2024

(65) Prior Publication Data

US 2024/0216687 A1 Jul. 4, 2024

Related U.S. Application Data

(63) Continuation of application No. 18/144,812, filed on May 8, 2023, now Pat. No. 11,865,340, which is a
(Continued)

(51) Int. Cl.
*A61N 1/36* (2006.01)
*A61N 1/04* (2006.01)
(Continued)

(52) U.S. Cl.
CPC ....... *A61N 1/36046* (2013.01); *A61N 1/0456* (2013.01); *A61N 1/3603* (2017.08);
(Continued)

(58) Field of Classification Search
CPC .................. A61N 1/36046; A61N 1/3603
(Continued)

(56) References Cited

U.S. PATENT DOCUMENTS 3,376,870 A 4/1968 Yamamoto et al.
3,669,119 A 6/1972 Symmes
(Continued)

FOREIGN PATENT DOCUMENTS

EP 3103507 A1 12/2016
WO 2014110575 A1 7/2014
(Continued)

OTHER PUBLICATIONS

Chaikin, et al., "Microcurrent stimulation in the treatment of dry and wet macular degeneration", "Clinical Ophthalmology", Dec. 2015, pp. 2345-2353, vol. 2015:9.
(Continued)

*Primary Examiner* — Nadia A Mahmood
(74) *Attorney, Agent, or Firm* — Fox Rothschild LLP

(57) ABSTRACT

A system and method for applying stimulation therapy to a patient, the system including a first stimulation strip that includes a first elongated portion configured to be placed on the upper eyelid of the first eye of the patient and a second elongated portion configured to be placed on the lower eyelid of the first eye of the patient, wherein the first stimulation strip includes: a first plurality of individually controlled electrodes configured to deliver a microcurrent stimulation therapy to the patient, a first plurality of individually controlled light emitters configured to deliver light stimulation therapy to the patient, and a first plurality of individually controlled heat sources configured to deliver heat therapy to the patient; and a controller operatively coupled to the first stimulation strip and configured to
(Continued)

control delivery of the microcurrent stimulation therapy, the light stimulation therapy, and the heat therapy.

30 Claims, 12 Drawing Sheets

Related U.S. Application Data continuation of application No. 17/866,259, filed on Jul. 15, 2022, now Pat. No. 11,642,526, which is a continuation of application No. 17/416,024, filed as application No. PCT/US2019/067627 on Dec. 19, 2019, now Pat. No. 11,439,823.

(60) Provisional application No. 62/783,116, filed on Dec. 20, 2018.

(51) Int. Cl.
| | | |
|---|---|---|
| *A61N 5/06* | (2006.01) | |
| *G06F 21/62* | (2013.01) | |
| *G16H 10/60* | (2018.01) | |
| *G16H 20/30* | (2018.01) | |
| *G16H 40/67* | (2018.01) | |

(52) U.S. Cl.
CPC ............ *A61N 5/06* (2013.01); *G06F 21/6245* (2013.01); *G16H 10/60* (2018.01); *G16H 20/30* (2018.01); *G16H 40/67* (2018.01); *A61N 2005/0648* (2013.01)

(58) Field of Classification Search
USPC .......................................................... 607/53
See application file for complete search history.

(56) References Cited

U.S. PATENT DOCUMENTS

| | | | |
|---|---|---|---|
| 4,018,218 | A | 4/1977 | Carlson et al. |
| 4,989,605 | A | 2/1991 | Rossen |
| 5,522,864 | A | 6/1996 | Wallace et al. |
| 5,730,720 | A | 3/1998 | Sites et al. |
| 5,843,147 | A | 12/1998 | Testerman et al. |
| 6,035,236 | A | 3/2000 | Jarding et al. |
| 6,275,735 | B1 | 8/2001 | Jarding et al. |
| 6,350,275 | B1 | 2/2002 | Vreman et al. |
| 6,385,727 | B1 | 5/2002 | Cassagnol et al. |
| 6,445,955 | B1 | 9/2002 | Michelson et al. |
| 6,454,709 | B1 | 9/2002 | Kleinschmidt et al. |
| 6,516,227 | B1 | 2/2003 | Meadows et al. |
| 6,587,728 | B2 | 7/2003 | Fang et al. |
| 6,636,754 | B1 | 10/2003 | Baura et al. |
| 6,792,314 | B2 | 9/2004 | Byers et al. |
| 6,993,387 | B2 | 1/2006 | Connelly et al. |
| 7,062,319 | B1 | 6/2006 | Ihme et al. |
| 7,069,084 | B2 | 6/2006 | Yee |
| 7,158,834 | B2 | 1/2007 | Paul, Jr. |
| 7,215,989 | B1 | 5/2007 | Burks |
| 7,239,910 | B2 | 7/2007 | Tanner |
| 7,251,528 | B2 | 7/2007 | Harold |
| 7,326,181 | B2 | 2/2008 | Katims |
| 7,771,342 | B2 | 8/2010 | Rademacher et al. |
| 7,883,536 | B1 | 2/2011 | Bendett et al. |
| 8,116,841 | B2 | 2/2012 | Bly et al. |
| 8,160,696 | B2 | 4/2012 | Bendett et al. |
| 8,494,625 | B2 | 7/2013 | Hargrove |
| 8,554,324 | B2 | 10/2013 | Brocke |
| 8,560,077 | B2 | 10/2013 | Feinstein |
| 8,639,345 | B2 | 1/2014 | Eipper et al. |
| 8,731,657 | B1 | 5/2014 | Shambayati et al. |
| 8,781,594 | B2 | 7/2014 | Lindenthaler |
| 8,956,274 | B2 | 2/2015 | Schneider et al. |
| 8,958,883 | B2 | 2/2015 | Mueller et al. |
| 8,996,131 | B1 | 3/2015 | Owen et al. |
| 9,061,148 | B2 | 6/2015 | Bachinski et al. |
| 9,199,080 | B2 | 12/2015 | Gekeler et al. |
| 9,308,363 | B2 | 4/2016 | Goroszeniuk et al. |
| 9,387,321 | B2 | 7/2016 | Greenberg et al. |
| 9,474,446 | B2 | 10/2016 | Amann et al. |
| 9,510,972 | B2 | 12/2016 | Badawi |
| 9,566,427 | B2 | 2/2017 | Wagner |
| 9,579,040 | B2 | 2/2017 | Rafferty et al. |
| 9,675,794 | B2 | 6/2017 | Miller |
| 9,719,977 | B2 | 8/2017 | Korb et al. |
| 9,724,230 | B2 | 8/2017 | Badawi |
| 9,918,875 | B2 | 3/2018 | Ha et al. |
| 9,977,865 | B1 | 5/2018 | LaBorde |
| 9,999,766 | B2 | 6/2018 | Elliott |
| 10,016,600 | B2 | 7/2018 | Creasey et al. |
| 10,080,683 | B2 | 9/2018 | Ha et al. |
| 10,124,160 | B2 | 11/2018 | Dorvall et al. |
| 10,272,256 | B2 | 4/2019 | Toyos |
| 10,376,691 | B2 | 8/2019 | De Toni et al. |
| 10,391,312 | B2 | 8/2019 | Mowery et al. |
| 10,456,579 | B2 | 10/2019 | Salazar |
| 10,507,135 | B2 | 12/2019 | Ha et al. |
| 10,520,997 | B2 | 12/2019 | Sen et al. |
| 10,525,255 | B2 | 1/2020 | Wingeier et al. |
| 10,537,476 | B2 | 1/2020 | Ha et al. |
| 10,543,124 | B2 | 1/2020 | Ha |
| 10,695,219 | B2 | 6/2020 | Herchman et al. |
| 10,869,781 | B2 | 12/2020 | Ha |
| 10,973,680 | B2 | 4/2021 | Badawi et al. |
| 11,007,367 | B2 | 5/2021 | O'Clock |
| 11,172,750 | B2 | 11/2021 | Park et al. |
| 11,213,427 | B2 | 1/2022 | Xiao |
| 11,305,118 | B2 | 4/2022 | Rockley et al. |
| 11,364,380 | B2 | 6/2022 | Goodall et al. |
| 2002/0026225 | A1 | 2/2002 | Segal |
| 2005/0137649 | A1 | 6/2005 | Paul, Jr. |
| 2008/0028214 | A1 | 1/2008 | Tafoya et al. |
| 2008/0171929 | A1 | 7/2008 | Katims |
| 2009/0048642 | A1 | 2/2009 | Goroszeniuk |
| 2009/0099405 | A1 | 4/2009 | Schneider et al. |
| 2010/0049180 | A1 | 2/2010 | Wells et al. |
| 2010/0298863 | A1 | 11/2010 | Hindinger et al. |
| 2011/0081333 | A1 | 4/2011 | Shantha et al. |
| 2012/0203310 | A1 | 8/2012 | Pugh et al. |
| 2014/0081369 | A1 | 3/2014 | Sosa et al. |
| 2015/0018927 | A1 | 1/2015 | Warschewske |
| 2016/0263376 | A1 | 9/2016 | Yoo et al. |
| 2017/0027812 | A1 | 2/2017 | Hyde et al. |
| 2017/0036009 | A1 | 2/2017 | Hughes et al. |
| 2017/0106203 | A1 | 4/2017 | Schneider et al. |
| 2018/0325729 | A1 | 11/2018 | Rynerson |
| 2019/0046794 | A1 | 2/2019 | Goodall et al. |

FOREIGN PATENT DOCUMENTS

| | | |
|---|---|---|
| WO | 2014142970 A1 | 9/2014 |
| WO | 2018071630 A1 | 4/2018 |

OTHER PUBLICATIONS

Fujikado, et al., "Effect of Transcorneal Electrical Stimulation in Patients with Nonarteritic Ischemic Optic Neuropathy or Traumatic Optic Neuropathy", "Jpn J Ophthalmol", May-Jun. 2006, pp. 266-273, vol. 50.

Groppa, et al., "A practical guide to diagnostic transcranial magnetic stimulation: Report of an IFCN committee", "Clin. Neurophysiol.", May 2012, pp. 858-882, vol. 123, No. 5.

Kloth, "Electrical Stimulation Technologies for Wound Healing", "Advances in Wound Care", Aug. 2014, pp. 81-90, vol. 3, No. 2.

Mayo Clinic, "Transcranial magnetic stimulation", "www.mayoclinic.org/tests-procedures/transcranial-magnetic-stimulation/about/pac-20384625?p=1", 1998.

Morimoto, et al., "Evaluation of residual retinal function by pupillary constrictions and phosphenes using transcorneal electrical stimulation in patients with retinal degeneration", Mar. 21, 2006, pp. 1283-1292, vol. 244.

(56) References Cited

OTHER PUBLICATIONS

Wrobel, et al., "Therapy for Retinal Degeneration", "Retina Today", Oct. 2011, pp. 80-81.

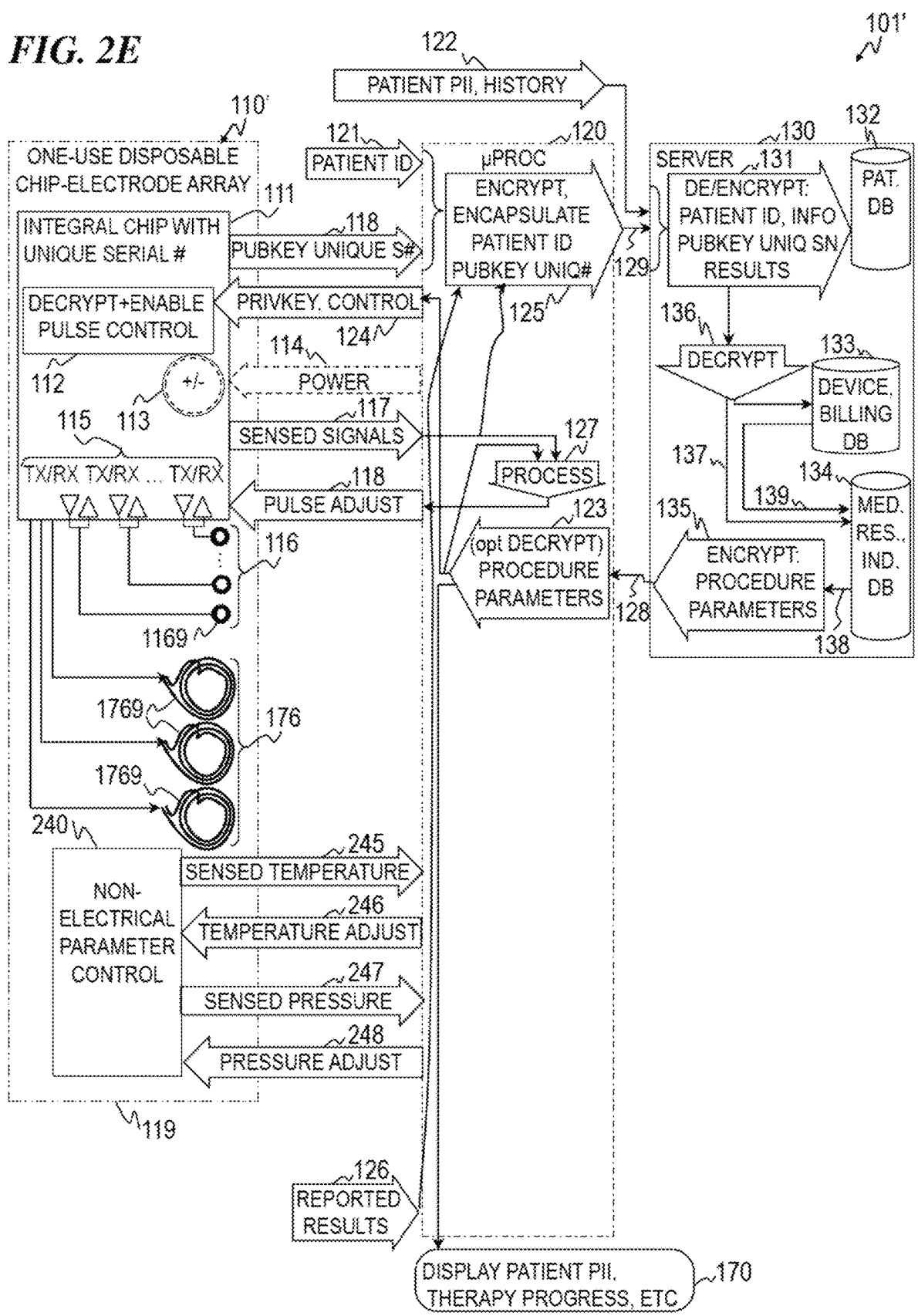

APPARATUS AND METHOD FOR MICROCURRENT-STIMULATION THERAPY

CROSS-REFERENCE TO RELATED APPLICATIONS

This application is a continuation application of U.S. patent application Ser. No. 18/144,812, filed May 8, 2023, which is a continuation application of U.S. patent application Ser. No. 17/866,259, filed Jul. 15, 2022, now U.S. Pat. No. 11,642,526, which is a continuation of U.S. patent application Ser. No. 17/416,024, filed Jun. 18, 2021, now U.S. Pat. No. 11,439,823, which is a national-phase filing of, and claims priority benefit of, PCT Patent Application No. PCT/US2019/067627, filed Dec. 19, 2019, which claims priority benefit, including under 35 U.S.C. § 119(e), of U.S. Provisional Patent Application 62/783,116 filed Dec. 20, 2018, each of which is incorporated herein by reference in its entirety.

FIELD OF THE INVENTION

The present invention relates to treatment of a human condition and more particularly to a system and method for applying bio-electric microcurrent-stimulation therapy, light-stimulation therapy, and/or heat therapy to the human body.

BACKGROUND OF THE INVENTION

Chronic pain is a problem for millions of individuals throughout the world. One method of treating such pain is to provide microcurrent stimulation around or near the areas where the pain is occurring. Microcurrent, which typically is defined as current below 1 milliamp, can provide rapid and long-lasting pain relief for a wide variety of pain syndromes. Generally, microcurrent stimulation therapy typically includes applying a current in the range of about 20 to about 300 microamps to the affected area. The current blocks neuronal transmission of pain signals and stimulates the release of endorphins to help relieve the pain in chronic and acute pain patients. Within certain levels of this range, the microcurrent mimics the body's own electrical current level and is what we term "bio-electric current."

In addition to chronic pain relief, microcurrent therapy is being used to treat a number of visual diseases, including macular degeneration, retinitis pigmentosa, and glaucoma, among other eye diseases. It is believed through secondary literature that this microcurrent treatment stimulates blood flow, increases ATP (adenosine triphosphate) at the cellular level, and enhances cellular permeability. Further, it is believed such stimulation can re-establish functional neural pathways for muscle and brain, as well as for blood vessel and brain.

1. Primary Disease for Treatment (AMD)

Age-related Macular degeneration (AMD) is a very common eye disease, affecting more people than glaucoma. Macular degeneration is the most frequent cause of blindness for patients aged 60 and above in the United States, and is estimated to affect over 10 million Americans. (Source: National Health Institute). Macular degeneration results in the deterioration of various retinal tissues in the region of the macula, the central, most sensitive light-sensing area of the retina responsible for detailed central vision. Impaired blood circulation in the central retina, with partial to full corresponding vision loss, is a typical consequence of macular degeneration.

2. Costs of Healthcare and Eye Care

The U.S. spends $2.7 trillion in healthcare each year, of which eye care represents roughly three percent or $60-$70 billion of the total. According to Eurostat, the European Union (EU) spends 45.7% of that amount, or about $1.23 trillion. Expenditures for eye care are growing at six percent annually. According to the National Institutes of Health (NIH), it is expected to continue to grow at least six percent over the next several decades, driven by the aging population.

Macular degeneration causes about $184 billion in lost productivity each year and approximately $51 billion is spent treating macular degeneration each year in the United States. 90% of macular degeneration cases are the "Dry" or non-bleeding form, termed "Atrophic AMD," and about 10% of cases are the "Wet" or bleeding form, termed "Exudative AMD."

3. Disease Prevalence

Because there is currently no approved treatment for dry AMD, little research has been done on the market potential. There is, however, significant data on the large numbers of people affected by AMD and is estimated to cause about 8.7% of blindness and low vision globally. According to a report from the World Health Organization, "AMD is the primary cause of blindness in the developed countries and the third leading cause worldwide." The prevalence of AMD in Europe is estimated to be: 16.3 million people (excluding southeastern and Eastern Europe), and in the United States 10.2 million people. (Source: www.wrongdiagnosis.com).

Further, this increases to a combined total of 41 million when adding in Canada, Australia/New Zealand, Russia, and Japan. Ninety percent (90%) of these cases are dry AMD for which there is no currently approved treatment to restore vision.

Approximately 25% of the population (in the target markets, aged 65 to 75 years old) has AMD, and this increases to 35% for ages 75 and older. Within the next 10 to 20 years, as baby boomers reach their mid-sixties and older, the prevalence of the disease is projected to dramatically increase. In a study funded by the U.S. Centers for Disease Control and Prevention, researchers reported that as many as 9.1 million people in the U.S. had AMD in 2010 and 17.8 million would have it by 2020.

4. Causes of AMD

Normal retinal cell function is a photochemical reaction converting light energy to an electrical impulse which travels to the brain and vision occurs. With AMD and other visual system diseases, diseased, inflamed retinal cells eventually lose cell function. Adenosine triphosphate (ATP) levels drop, protein synthesis drops, the electrical resistance goes up, and cell membrane electrical potential goes down. Basically, the cells would appear to go dormant for a time before they die.

It is believed that when electrical stimulation is provided to the cells before they die, blood vessel permeability is increased, normal cellular electrical potential is achieved, ATP levels increase, protein synthesis will occur again, and normal cell metabolism is restored thereby improving or restoring vision loss. In addition, in vitro studies have demonstrated that electrical stimulation appears to have a healing effect on the small blood vessels in the retina, promoting a more efficient delivery of nutrients to the retinal cells and a more efficient elimination of metabolic by-products.

The retinal pigment epithelium (RPE) is the support-cell complex for the photosensitive rod and cone cells which make up the light-sensing retina. The RPE is the first to be affected by circulation impairment. Once affected by poor circulation, the RPE cannot efficiently assist the rods and cones in removing the metabolic and photochemical response by-products, which are common during cellular function. Yellowish-colored sub-retinal deposits called "drusen" form when extracellular by-products are not carried away by blood circulating through the eye. As a result, the photoreceptor cells in the macula enter a dormant, toxic state and do not respond to light. If normal retinal cellular metabolism is not restored, the cells die and visual acuity is permanently lost. Thus, it is believed that microcurrent stimulation will help rejuvenate the cells in the retina to slow or stop degeneration of the eye due to AMD.

5. Potential Treatment/Solution

Clinical studies have demonstrated that with the proper bio-electric microcurrent-stimulation waveform and therapy procedure, AMD may be slowed or stopped in a large number of people suffering from the disease. But, the efficacy of these therapies can be affected by the manual techniques medical professionals use to administer said therapy. Where patients have significant skin impedance, or there is a poor conductivity, uptake of the stimulation level is limited and will limit the treatment efficacy. This invention, consisting of a headset appliance of electrodes in a circular, or semi-circular fashion around the eye addresses that problem by communicating, via sensors, with an apparatus that generates bio-electric microcurrent stimulation.

U.S. Pat. No. 10,391,312, issued Aug. 27, 2019 to Blair P. Mowery et al. and titled "Apparatus and method for ocular microcurrent stimulation therapy," is a U.S national phase of PCT Application Serial No. PCT/US2016/051550 filed on Sep. 13, 2016 with the title "Apparatus and method for ocular microcurrent stimulation therapy" (published as WO 2017/048731), which claims priority to U.S. Provisional Patent Application 62/283,870 filed on Sep. 15, 2015 by Blair Phillip Mowery et al., titled "Appliance for microstimulation therapy using a disposable material affixed to the upper and lower eye lid & other body parts," U.S. Provisional Patent Application 62/283,871 filed on Sep. 15, 2015 by Marshall T. Masko et al., titled "Apparatus for a method of application of microcurrent stimulation therapy, consisting of a goggle device affixed to and encircling the upper and/or lower eyelids, as well as other body parts," and U.S. Provisional Patent Application 62/365,838, filed Jul. 22, 2016 by Tapp et al., titled "Appliance for micro-current stimulation," each of which is incorporated herein by reference in its entirety. U.S. Pat. No. 10,391,312 describes devices and methods to deliver microcurrent stimulation therapy to the human body, when connected to a microstimulation current-generating apparatus. The method of applying microcurrent stimulation therapy to key points around the eye for treatment of problems such as macular degeneration, retinitis pigmentosa, glaucoma, optic neuritis and other eye-related or nerve-related conditions, as well as other diseases, such as Bell's Palsy, requiring localized stimulation to the eyes and/or on other body parts.

U.S. Pat. No. 6,035,236 issued to Jarding, et al. on Mar. 7, 2000 with the title "Methods and apparatus for electrical microcurrent stimulation therapy" and is incorporated herein by reference in its entirety. U.S. Pat. No. 6,035,236 describes an apparatus for supplying an electrical signal to a body part in order to provide microcurrent stimulation therapy to the body part. The apparatus preferably includes a first sweep wave or sweep frequency signal generator configured to generate a first sweep wave signal, a buffer amplifier circuit configured to receive the first sweep wave signal from the first sweep signal generator and amplify and buffer the sweep wave signal creating a buffered sweep wave signal. In addition, the apparatus preferably includes a current limiting circuit configured to receive the buffered sweep wave signal from the buffer amplifier circuit and limit the amount of current supplied to the body part. Finally, the apparatus preferably comprises a probe for applying the sweep wave signal to the body part. The apparatus may further comprise a second signal generator for generating a second signal which may comprise either a sweep wave signal or a non-sweep wave signal. The apparatus also will include a signal combining circuit configured to receive the first and second signals from the first and second signal generators and combine the first and second signals into a composite sweep wave signal.

U.S. Pat. No. 6,275,735 issued to Jarding et al. on Aug. 14, 2001 with the title "Methods and apparatus for electrical microcurrent stimulation therapy" and is incorporated herein by reference in its entirety. U.S. Pat. No. 6,275,735 describes a method and apparatus for providing microcurrent stimulation therapy to a body part. In one embodiment, a method allows digital control of the modulation frequency of the microcurrent signal. The method includes receiving a first digital data word which is used to produce a first frequency related to the first digital data word, whereupon, a first microcurrent signal at the first frequency is applied to the body part. A second digital data word is received and used to produce a second frequency related to the second digital data word. A second microcurrent signal at the second frequency is applied to the body part. In another embodiment, a method allows direct digital synthesis of the microcurrent stimulation signal. A first digital data word is used to produce a first analog voltage which is applied to the body part. A second digital data word is used to produce a second analog voltage which is also applied to the body part, where the first analog voltage is different from the second analog voltage. In yet another embodiment, an apparatus for providing microcurrent stimulation therapy includes a digital-to-analog converter, a controller and a plurality of data words. The controller is coupled to the digital-to-analog converter and supplies the digital-to-analog converter with digital data words in order to generate an electrical signal for the microcurrent stimulation therapy.

U.S. Pat. No. 5,730,720 issued to Sites et al. on Mar. 24, 1998 with the title "Perfusion hyperthermia treatment system and method," and is incorporated herein by reference. U.S. Pat. No. 5,730,720 describes a method and apparatus to automatically monitor and control a perfusion hyperthermia treatment using a system including one or more programmed computers, and mechanical and sensor subsystems. The system includes a fluid path between a patient and an external fluid-treatment subsystem, wherein control of the external fluid-treatment subsystem includes feedback from sensors coupled to the patient. The resulting integrated system provides automated monitoring and control of the patient, the external fluid-treatment subsystem, and the treatment. In one embodiment, the fluid passing between the patient and the external fluid-treatment subsystem is blood. In one embodiment, an apparatus and method are provided for using a computerized system for a perfusion hyper/hypothermia treatment of a patient which obtains a body fluid having a temperature. A plurality of temperature signals representative of temperatures at each of a plurality of patient locations on or within the patient are coupled to the computer system. Measured temperatures are compared to a set of stored parameters in the computer system to generate a comparison value which controls a change in the temperature of the body fluid. The body fluid is then perfused into the patient to either warm, cool, or maintain the current temperature of the patient. In one such embodiment, the body fluid is blood withdrawn from the patient. In another such embodiment, the body fluid is saline.

U.S. Patent Application Publication 2014/0081369 by Sosa, Victor Manuel Valencia et al. published on Mar. 20, 2014 with the title "Headache-treatment device with gel dispensing kit and method" and is incorporated herein by reference in its entirety. Patent Application Publication 2014/0081369 describes an electrical-stimulation device with gel-dispensing kit, and a method of making and using the parts of the kit. A convenient and easy-to-use system to provide an electrically conductive path from a transcutaneous electrical nerve stimulation (TENS) device to the skin surface of a patient to supply transcutaneous stimulation, even through hair. The invention provides improved prevention and treatment for headache, depression, alertness, attention deficit hyperactivity disorder (ADHD), epilepsy, anxiety, post-traumatic stress disorder (PTSD), and behavioral and/or other disorders. Some embodiments provide a headache-treatment system that includes an electrode base shaped to conform to a back of a human head; a TENS having projecting spring electrodes each connected to the electrode base; means for holding an electrically conductive gel in a plurality of sealed pockets; and means for unsealing the means for holding the gel and applying the gel substantially simultaneously to the projecting spring electrodes.

U.S. Patent Application Publication 2017/0300098 by Sen et al. published on Oct. 19, 2017 with the title "Supplying power to a computer accessory from a captured WIFI signal" and is incorporated herein by reference in its entirety. Patent Application Publication 2017/0300098 describes examples of capturing a Wi-Fi signal from a computing device corresponding to a computing accessory and harvesting energy from the captured Wi-Fi signal. The examples power the computing accessory based on the harvested energy.

U.S. Patent Application Publication 2008/0028214 by Tafoya et al. published on Jan. 31, 2008 with the title "Secure flash media for medical records" and is incorporated herein by reference in its entirety. Patent Application Publication 2008/0028214 describes a secure mobile device for storing data in a secure manner. The secure mobile device has a microarchitecture connected via an interface to flash memory on the device. The microarchitecture is able to authenticate the access of information stored on the secure mobile device using a private key. Upon authentication of the access of information, a record owner of the device may provide the stored information to third party trusted entities using an associated public key. The secure mobile device allows for secure transaction of confidential data on a variety of systems at a number of locations.

U.S. Patent Application Publication 2010/0049180 by Jonathon D. Wells et al. published on Feb. 25, 2010 with the title "System and method for conditioning animal tissue using laser light" and is incorporated herein by reference in its entirety. Patent Application Publication 2010/0049180 describes systems and methods for prophylactic measures aimed at improving wound repair. In some embodiments, laser-mediated preconditioning would enhance surgical wound healing that was correlated with hsp70 expression. Using a pulsed laser ($\lambda$=1850 nm, $T_p$=2 ms, 50 Hz, H=7.64 mJ/cm$^2$) the skin of transgenic mice that contain an hsp70 promoter-driven luciferase were preconditioned 12 hours before surgical incisions were made. Laser protocols were optimized using temperature, blood flow, and hsp70-mediated bioluminescence measurements as benchmarks. Bioluminescent imaging studies in vivo indicated that an optimized laser protocol increased hsp70 expression by 15-fold. Under these conditions, healed areas from incisions that were laser-preconditioned were two times stronger than those from control wounds. Our data suggest that these methods can provide effective and improved tissue-preconditioning protocols and that mild laser-induced heat shock that correlated with an expression of Hsp70 may be a useful therapeutic intervention prior to or after surgery.

U.S. Pat. No. 6,385,727 issued to Cassagnol et al. on May 7, 2002 with the title "Apparatus for providing a secure processing" and is incorporated herein by reference in its entirety. U.S. Pat. No. 6,385,727 describes a secure processing environment. In one embodiment, the apparatus includes a read/write memory for storing encrypted information. It also includes a processor, a cipherer and an authenticator. The cipherer is in communication with the read/write memory for receiving encrypted information therefrom and is configured to decrypt the encrypted information into decrypted information to be returned to the memory for subsequent use by the processor. The authenticator authenticates the decrypted information prior to use by the processor and re-authenticates the information prior to re-encryption by the cipherer.

U.S. Pat. No. 7,239,910 to Tanner issued on Jul. 3, 2007 with the title "Methods and devices for transcranial magnetic stimulation and cortical cartography," and is incorporated herein by reference. U.S. Pat. No. 7,239,910 describes a method for stimulating and/or inhibiting at least one point or area of a brain using at least one stimulation device, wherein: the spatial structure of the head or brain is recorded; a three-dimensional simulation model of the surface of the brain is generated from the recording of the spatial structure of the brain; and the stimulation device is arranged relative to the head or brain using the three-dimensional simulation model of the surface of the brain, such that the at least one point or area of the brain can be stimulated using the stimulation device; a device for stimulating and/or inhibiting at least one point or area of a brain, comprising a recording device for detecting the spatial structure of the brain, a computational device for generating a simulation model of the surface of the brain and at least one stimulation or induction device, in particular a coil; a method for determining the function of a particular area of the brain, wherein at least one particular area is stimulated using a stimulation device and the stimulus response is measured at least two different positions, and a device for determining the function of a particular area of the brain, comprising at least one stimulation device and at least two stimulus detection devices.

U.S. Pat. No. 7,883,536 by Mark P. Bendett et al. issued on Feb. 8, 2011 with the title "Hybrid optical-electrical probes" and is incorporated herein by reference in its entirety. U.S. Pat. No. 7,883,536 describes an optical-signal vestibular-nerve stimulation device and method that provides different nerve stimulation signals to a plurality of different vestibular nerves, including at least some of the three semicircular canal nerves and the two otolith organ nerves. In some embodiments, balance conditions of the person are sensed by the implanted device, and based on the sensed balance conditions, varying infrared (IR) nerve-stimulation signals are sent to a plurality of the different vestibular nerves.

U.S. Pat. No. 8,160,696 by Mark P. Bendett et al. issued on Apr. 17, 2012 with the title "Nerve stimulator and method using simultaneous electrical and optical signals" and is incorporated herein by reference in its entirety. U.S. Pat. No. 8,160,696 describes an apparatus and method for stimulating animal tissue (for example to trigger a nerve action potential (NAP) signal in a human patient) by application of both electrical and optical signals for treatment and diagnosis purposes. The application of an electrical signal before or simultaneously to the application of a NAP-triggering optical signal allows the use of a lower amount of optical power or energy than would otherwise be needed if an optical signal alone was used for the same purpose and effectiveness. The application of the electrical signal may precondition the nerve tissue such that a lower-power optical signal can be used to trigger the desired NAP, which otherwise would take a higher-power optical signal were the electric signal not applied. Some embodiments include an implanted nerve interface having a plurality of closely spaced electrodes placed transversely and/or longitudinally to the nerve and a plurality of optical emitters.

U.S. Pat. No. 8,996,131 by James M. Owen et al. issued on Apr. 17, 2012 with the title "Nerve stimulator and method using simultaneous electrical and optical signals" and is incorporated herein by reference in its entirety. U.S. Pat. No. 8,996,131 describes a method and apparatus for infrared-light nerve stimulation-plus-therapeutic-heat (INS-plus-TH) that includes providing a plurality of light sources; providing a plurality of thermally conductive extensions configured to transfer heat generated by the plurality of light sources away from the plurality of light sources; emitting a plurality of infrared-light nerve-stimulation signals toward neural tissue of an animal from the plurality of light sources, wherein the emitted infrared-light nerve-stimulation signals are configured to generate action potentials in the neural tissue, and wherein the emitting of the plurality of infrared-light nerve-stimulation signals includes generating heat; controlling the emitting of the plurality of infrared-light nerve-stimulation signals to generate action potentials in the neural tissue; and transferring the heat generated by the plurality of light sources during the emitting of the plurality of infrared-light nerve-stimulation signals away from the plurality of light sources and into surrounding tissue of the animal using the plurality of thermally conductive extensions.

A publication titled "Transcranial magnetic stimulation" by Mayo Clinic, www.mayoclinic.org/tests-procedures/transcranial-magnetic-stimulation/about/pac-20384625?p=1 (2019) is incorporated herein by reference. This publication describes "Transcranial magnetic stimulation (TMS) is a noninvasive procedure that uses magnetic fields to stimulate nerve cells in the brain to improve symptoms of depression. TMS is typically used when other depression treatments haven't been effective. This treatment for depression involves delivering repetitive magnetic pulses, so it's called repetitive TMS or rTMS. How it works: During an rTMS session, an electromagnetic coil is placed against your scalp near your forehead. The electromagnet painlessly delivers a magnetic pulse that stimulates nerve cells in the region of your brain involved in mood control and depression. It's thought to activate regions of the brain that have decreased activity in depression. Though the biology of why rTMS works isn't completely understood, the stimulation appears to impact how the brain is working, which in turn seems to ease depression symptoms and improve mood."

A publication titled "Electrical Stimulation Technologies for Wound Healing" by Luther C. Kloth, Department of Physical Therapy, Marquette University (Advances in Wound Care, Vol. 3, No. 2, 2014), is incorporated herein by reference. This publication describes "The use of electric field (EF) energy applied to chronic wounds to enhance healing has been used for decades and is based on the existence of endogenous wound EFs that have been observed to direct cell migration after injury to the integument. The strength of the endogenous wound EFs measured in animals and humans that have been observed to direct cell migration (electrotaxis) after wounding have been quantified between 10 and 100 $pA/cm^2$. Research has verified that EF energy enhances the migration of lymphocytes, fibroblasts, macrophages, and keratinocytes. Furthermore, in recalcitrant wounds, it seems likely that the endogenous EFs are askew or absent, in which case the wounds often do not respond to SWC. When SWC alone fails to heal chronic wounds, electrical stimulation (ES) combined with SWC has been shown in several clinical trials to enhance healing and closure." (Footnote numbers removed.)

A publication titled "A practical guide to diagnostic transcranial magnetic stimulation: Report of an IFCN committee" by Groppa et al. was published in final edited form as: Clin. Neurophysiol. 2012 May; 123(5): 858-882. doi: 10.1016/j.clinph.2012.01.010, (www.ncbi.nlm.nih.gov/pmc/articles/PMC4890546/pdf/nihms787351.pdf) and is incorporated herein by reference. Groppa et al. describes "Transcranial magnetic stimulation (TMS) is an established neurophysiological tool to examine the integrity of the fast-conducting corticomotor pathways in a wide range of diseases associated with motor dysfunction. This includes but is not limited to patients with multiple sclerosis, amyotrophic lateral sclerosis, stroke, movement disorders, disorders affecting the spinal cord, facial and other cranial nerves. These guidelines cover practical aspects of TMS in a clinical setting. We first discuss the technical and physiological aspects of TMS that are relevant for the diagnostic use of TMS. We then lay out the general principles that apply to a standardized clinical examination of the fast-conducting corticomotor pathways with single-pulse TMS. This is followed by a detailed description of how to examine corticomotor conduction to the hand, leg, trunk and facial muscles in patients. Additional sections cover safety issues, the triple stimulation technique, and neuropediatric aspects of TMS."

U.S. Pat. No. 10,124,160 issued to Dorvall I I et al. on Nov. 13, 2018 with the title "Charge steering high density electrode array," and is incorporated herein by reference. U.S. Pat. No. 10,124,160 describes technology for deep brain stimulating including devices, systems, computer circuitry, and associated methods foe electrode arrays that are implanted in the patient's brain. Their deep brain stimulating device can include a semiconductor substrate, an array of electrodes coupled to the semiconductor substrate, and circuitry operable to control the array of electrodes. Each electrode can be operable to function as an anode, a cathode, a common, or a float independent of other electrodes in the array to create highly configurable electric fields.

There is a long-felt need for an improved method and apparatus for therapeutic application of electrical stimulation, optionally along with optical stimulation, thermal stimulation, and/or pharmaceutical stimulation, and for collection of data regarding the immediate and longer-term physiological results of such stimulation, analysis of such collected data and adjustment of the controlled parameters to future applications of the therapy to a particular patient and to sub-populations of similarly situated patients.

SUMMARY OF THE INVENTION

A system and method for applying stimulation therapy to a patient, the system including a first stimulation strip that includes a first elongated portion configured to be placed on the upper eyelid of the first eye of the patient and a second elongated portion configured to be placed on the lower eyelid of the first eye of the patient, wherein the first stimulation strip includes: a first plurality of individually controlled electrodes configured to deliver a microcurrent stimulation therapy to the patient, a first plurality of individually controlled light emitters configured to deliver light stimulation therapy to the patient, and a first plurality of individually controlled heat sources configured to deliver heat therapy to the patient; and a controller operatively coupled to the first stimulation strip and configured to control delivery of the microcurrent stimulation therapy, the light stimulation therapy, and the heat therapy.

In some embodiments, the present invention provides a microcurrent stimulation apparatus which connects to a micro-stimulation current generating device, wherein the microcurrent stimulation apparatus includes a headset device encircling the head, and connected to electrode strips (such as a one-use disposable chip-electrode array having a unique serial number or crypto code and other functionality that is used by the system to look up and deliver customized therapy to a particular patient having their own particular symptoms and medical history), which deliver the stimulation. In some embodiments, the apparatus also either contains a stimulation controller device or is connected to a separate control device, via either wired or wireless communications. Some embodiments include applying bio-electric microcurrent stimulation therapy (optionally along with optical stimulation, heat stimulation, and/or pharmaceutical therapy) for macular degeneration, retinitis pigmentosa, glaucoma, optic neuritis, Bell's Palsy and other eye diseases to key points around the eye, as well as other diseases requiring localized and precision stimulation on other body parts. Patient-specific therapy parameters (based on patient history, symptoms and past therapy sessions) are passed to the headset from a server, and patient specific data and results are collected to the server for use in adjusting parameters for future therapy sessions for the patient and other patients.

In some embodiments, the bio-electric micro-stimulation apparatus of the present invention includes a headset (similar to a crown worn on the head of the patient), that connects to one or more contact strips each having one or more sets of electrodes in contact with the skin around a perimeter of each eye of the patient, in order to provide stimulation encircling and/or overlapping the outer orbital cavity. The electrodes' contact points deliver the bio-electric microcurrent therapy when the headset is connected to a bio-electric micro-stimulation controller device (sometimes simply called the "controller") that controls the generation and delivery of such current.

In some embodiments, each contact strip having the treatment electrodes also contains a micro-chip (i.e., a "chip") that has electronics and a unique serial number (which is optionally encrypted), or a barcode to authenticate itself and the contact strip. In some embodiments, each contact strip's chip connects with the headset to control patient-specific therapy, payment, and usage. In addition, in some embodiments, there is a grounding-electrode component that includes one or more grounding electrodes. In various embodiments, the headset's electrodes are controlled by the bio-electric micro-stimulation controller device (the "controller") in one of three ways: (i) the controller is built into the headset as a self-contained unit; (ii) the controller is in a separate housing (such as a laptop computer or tablet computer) that is connected via wires to the headset and/or to the electrodes on the contact strip; or (iii) the controller is coupled to the headset via Wi-Fi or Bluetooth®. The Wikipedia entry for "Wi-Fi" indicates:

"Wi-Fi is technology for radio wireless local area networking of devices based on the IEEE 802.11 standards." The Wikipedia entry for "Bluetooth" indicates: "Bluetooth is a wireless technology standard for exchanging data over short distances (using short-wavelength UHF radio waves in the ISM band from 2.400 to 2.485 GHZ) from fixed and mobile devices, and building personal area networks (PANs)." In some embodiments, the headset is adjustable to fit various sized heads, or it may have an open-ended back which does not completely encircle the head (similar to eyeglass temples), so as to fit any sized head.

In some embodiments, the headset also couples via Wi-Fi or Bluetooth® to a server or computer, which recognizes the individual headset via algorithmic (encrypted data) codes built into the headset's control unit. Once the server or computer is connected to the headset and recognizes the headset's unique algorithmic code, the server or computer enables the headset to provide therapy using patient-specific parameters when initiated by a clinician or physician to conduct a treatment session. In some embodiments, the server or computer can simultaneously bill or charge the provider for payment of such treatment session. In some embodiments, the headset is rechargeable (e.g., via rechargeable batteries or supercapacitors or other on-headset power source) and is recharged via a base station or other power supply.

This description of the invention uses the term "bio-electric microcurrent" because the microcurrent level selected for the applied therapy mirrors the body's own biological electrical current. Hence the term: "bio-electric current."

In some embodiments, the headset device of the present invention is reusable (i.e., not a one-use disposable unit), and in others it is a one-time disposable unit. Further, in some embodiments, since the headset device does not directly touch the treated eye area or other areas of the patient's skin, there is no need for repeated sterilization or sanitization to avoid cross-patient eye contamination. In contrast, the skin-contact strip and its electrodes do touch the treated area and are considered to be one-use disposable items. The headset device will be maintained at a sanitary standard.

In some embodiments, the electrodes of the skin-contact strip, which connects to the headset, have a conductive gel (or the like) applied on at least the inner perimeter at the electrode points for proper conductivity for stimulation therapy, which generates the prescribed bio-electric microcurrent at an appropriate amplitude, duty cycle, and/or repetition rate or frequency to the appropriate area of the eye, in a timed and dosed temporal sequence to the multiple electrode points on the electrodes of the skin-contact strip affixed near or to the eye lids. In some embodiments, the electrode points also connect to a sensor (such as an electrical preamplifier and/or analog-to-digital converters, or sensors embedded in the headset or in the outside stimulation device, which will provide feedback to the device to measure for any impedance of the electrode being driven by the electrical stimulation current, and the controller and its electronics, based on the sensed current or impedance, have the ability to automatically adjust the current level to maintain the initially selected prescribed treatment bio-electric current level. In some embodiments, the electrode(s) being driven with electrical current at a given time are called "active" and the other electrodes that are not being driven with electrical current at a given time are called "passive." In some embodiments, sensor electronics connected to the "passive" electrodes measure the voltage, stimulation output level, wave pattern, frequency, and amplitude, or at various distances from the presently driven "active" electrode(s), and the controller, based on that measured voltage, stimulation output level, wave pattern, frequency, and amplitude, can adjust the drive signal(s) to the presently driven "active" electrode(s)."

Microcurrent stimulation therapy has begun to be used to treat age-related muscular degeneration (AMD) and other visual system diseases; however, the methods and apparatus used in the prior art do not maximize the therapeutic effect and do not provide a way to monitor the therapeutic delivery and encourage patient compliance with the prescribed treatment regimen. Current devices may not deliver properly concentrated stimulation signals at the point where it is appropriately needed. In addition, stimulation levels can encounter impedance, which blocks or reduces the stimulation level chosen, thereby failing to deliver the appropriate level of stimulation required for proper treatment.

This new invention contains a method to carry and apply an electrical signal, termed "bio-electric microcurrent," which is a form of electrical stimulation, or "e-stim," to a specific body part (e.g., the eye) or selected body parts for treatable diseases, to promote or enable healing of the selected and treated tissue areas. Bio-electric microcurrent is a microcurrent range (e.g., in some embodiments, 100 µA to 350 µA) pulsed into the body, which mimics the body's own electric current (e.g., in some embodiments, the microcurrent stimulation ranges from 0-1000 micro-Amps). Said apparatus can deliver the appropriate stimulation to specifically targeted selected areas, as well as maintain the appropriate pressure required to eliminate or minimize patient impedance, while also continuously monitoring the stimulation level delivered to the patient, via a proprietary sensor to ensure it stays consistent with the level selected by the clinician, regardless of impedance or other issues. The invention, which in some embodiments is placed on the upper and lower eye lids, via the sensor, can automatically adjust such stimulation to the initial prescribed dosage when impedance is detected. The present invention provides this and other solutions to ensure optimum therapy is delivered, during the administration of treatments for macular degeneration and other eye disease problems.

BRIEF DESCRIPTION OF THE DRAWINGS

A more complete understanding of the present invention may be derived by referring to the detailed description and claims when considered in connection with the figures, wherein like reference numbers refer to similar items throughout the figures.

FIG. 2E is a block diagram of a system 101' for delivering stimulation signals to at least some of a plurality 116 of electrodes 1169 connected to the skin of a patient and for optionally sensing signals from temperature sensor(s) and/or pressure sensor(s), according to some embodiments of the present invention.

DESCRIPTION OF PREFERRED EMBODIMENTS

Figure 1A:
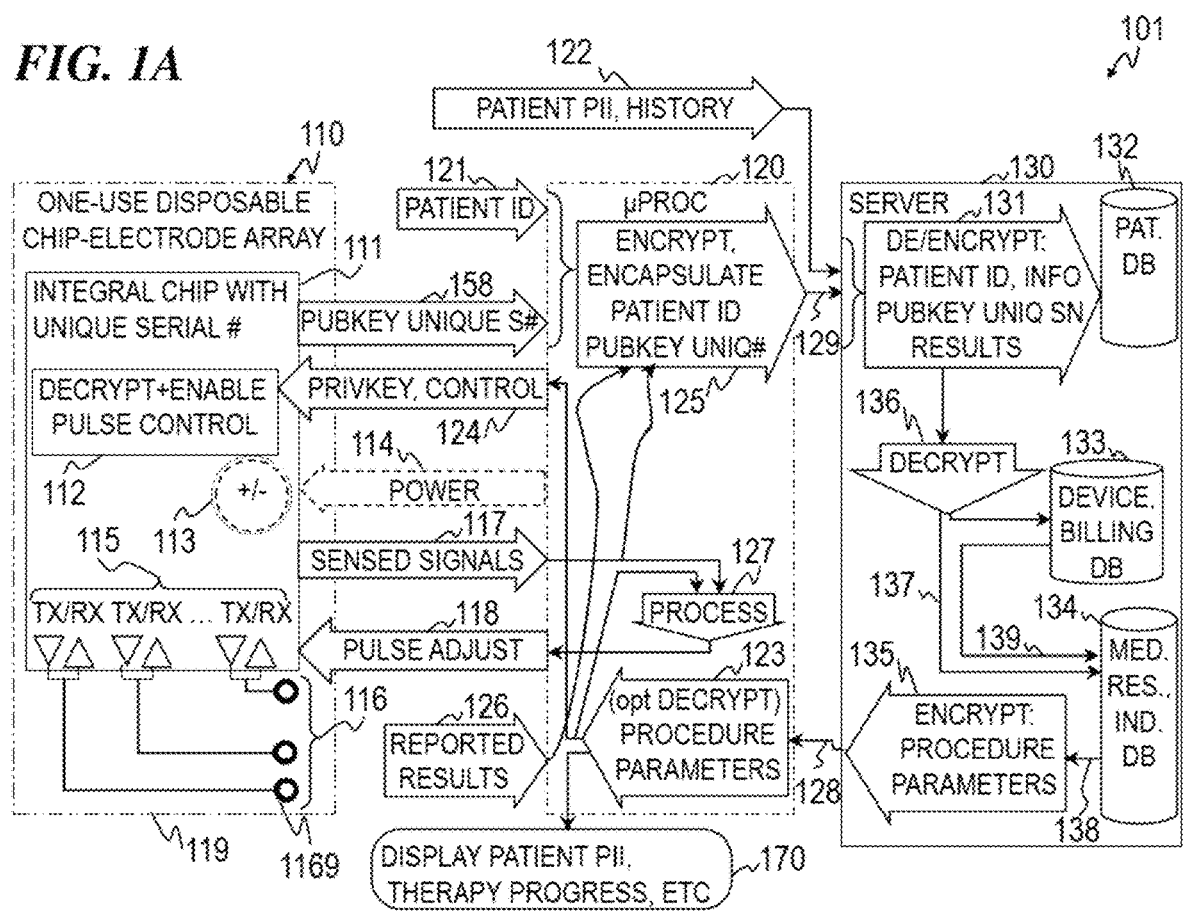
FIG. 1A is a block diagram of a system 101 for delivering stimulation signals to at least some of a plurality 116 of electrodes connected to the skin of a patient and for optionally sensing signals from at least some of the plurality 116 of electrodes, according to some embodiments of the present invention.

Although the following detailed description contains many specifics for the purpose of illustration, a person of ordinary skill in the art will appreciate that many variations and alterations to the following details are within the scope of the invention. Specific examples are used to illustrate particular embodiments; however, the invention described in the claims is not intended to be limited to only these examples, but rather includes the full scope of the attached claims. Accordingly, the following preferred embodiments of the invention are set forth without any loss of generality to, and without imposing limitations upon the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

It is specifically contemplated that the present invention includes embodiments having combinations and subcombinations of the various embodiments and features that are individually described herein (i.e., rather than listing every combinatorial of the elements, this specification includes descriptions of representative embodiments and contemplates embodiments that include some of the features from one embodiment combined with some of the features of another embodiment, including embodiments that include some of the features from one embodiment combined with some of the features of embodiments described in the patents and application publications incorporated by reference in the present application). Further, some embodiments include fewer than all the components described as part of any one of the embodiments described herein.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Certain marks referenced herein may be common-law or registered trademarks of third parties affiliated or unaffiliated with the applicant or the assignee. Use of these marks is for providing an enabling disclosure by way of example and shall not be construed to limit the scope of the claimed subject matter to material associated with such marks.

Overview of the New Technology

Embodiments of the present invention replace the need for manual application of the therapy currently used by a clinical professional. The appliance comprises a headset, connecting to a gel-strip or gel-strips containing electrodes and sensors for applying the bio-electric microcurrent therapy to the body part, in this case the eye. The headset's circular inner frame is positioned on the patient's head for both comfort and ease of treatment application. The headset is wired to either a self-contained controller or wired to connect to a separate bio-electric microcurrent stimulation device that generates the prescribed bio-electric microcurrent in sequence to the multiple electrode points on the material strips placed over to totality of the eye, or above and under the eye. The control device to which the headset invention is connected also contains a software system that is programmed to not only sequence the therapy to the various points on the material but also to detect impendence and adjust the level of bio-electric microcurrent to achieve optimum therapy.

In some embodiments, the present invention could be useful to include in a therapy for treating cancer or other maladies, for example by activating (or suppressing) chemicals of a chemotherapy or antibodies of an immunotherapy directed to a particular volume of tissue such as a tumor. In some embodiments, the activating (or suppressing) is accomplished by a combination of one or more of electrical stimulation, light stimulation, thermal stimulation and/or haptic stimulation applied with the chemicals of a chemotherapy or antibodies of an immunotherapy.

In some embodiments, the present invention includes an apparatus that replaces the need for long-duration manual applications of the microcurrent/electrostimulation therapy currently used (e.g., such as described in U.S. Pat. No. 6,035,236, which issued to Jarding, et al. on Mar. 7, 2000 with the title "Methods and apparatus for electrical microcurrent stimulation therapy" and/or U.S. Pat. No. 6,275,735, which issued to Jarding et al. on Aug. 14, 2001 with the title "Methods and apparatus for electrical microcurrent stimulation therapy") or being envisioned as used by a clinical professional. And, the present invention also enables the clinician or physician to deliver stimulation to a particular designated point on the body, as opposed to a broader coverage or blanketed area of the body. Current conventional technologies have two major drawbacks. First, conventional electrical stimulation delivered with a probe or pointer, is applied manually and takes a large amount of clinician time to administer and properly deliver the conventional electrical stimulation. Secondly, when conventional electrical stimulation gel pads are used in any kind of electrostimulation or microcurrent therapy, the gel pads cover and deliver stimulation across an area affecting a broad part of the human body, usually well in excess of 400 square millimeters. This shortcoming of conventional systems prevents the delivery of stimulation to a "pinpointed" area of, for example, 2 to 225 square millimeters (1.4 mm*1.4 mm=2 $mm^2$ to 15 mm*15 mm=225 $mm^2$), which— in contrast—the present invention does allow for, and the present invention can, in certain treatment therapies, be more efficacious due to a greater electrical stimulation level per unit area delivered on a smaller surface area that penetrates more deeply into the underlying tissue, which improves treatment performance.

FIG. 1A is a block diagram of a system 101 for delivering stimulation signals to at least some of a plurality 116 of electrodes 1169 connected to the skin of a patient and for optionally sensing signals from at least some of the plurality 116 of electrodes 1169, according to some embodiments of the present invention.

Figure 1B:
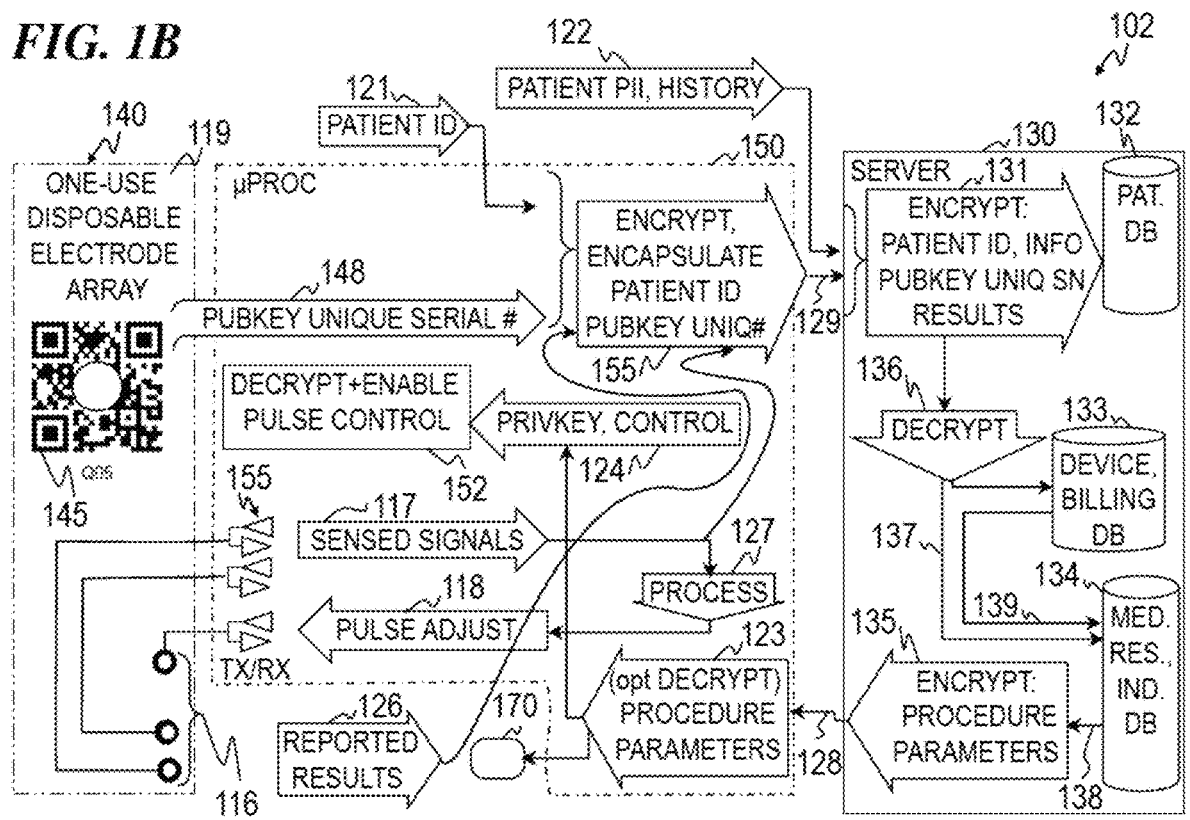
FIG. 1B is a block diagram of a system 102 for delivering stimulation signals to at least some of a plurality 116 of electrodes connected to the skin of a patient and for optionally sensing signals from at least some of the plurality 116 of electrodes, according to some embodiments of the present invention.
Figure 1C:
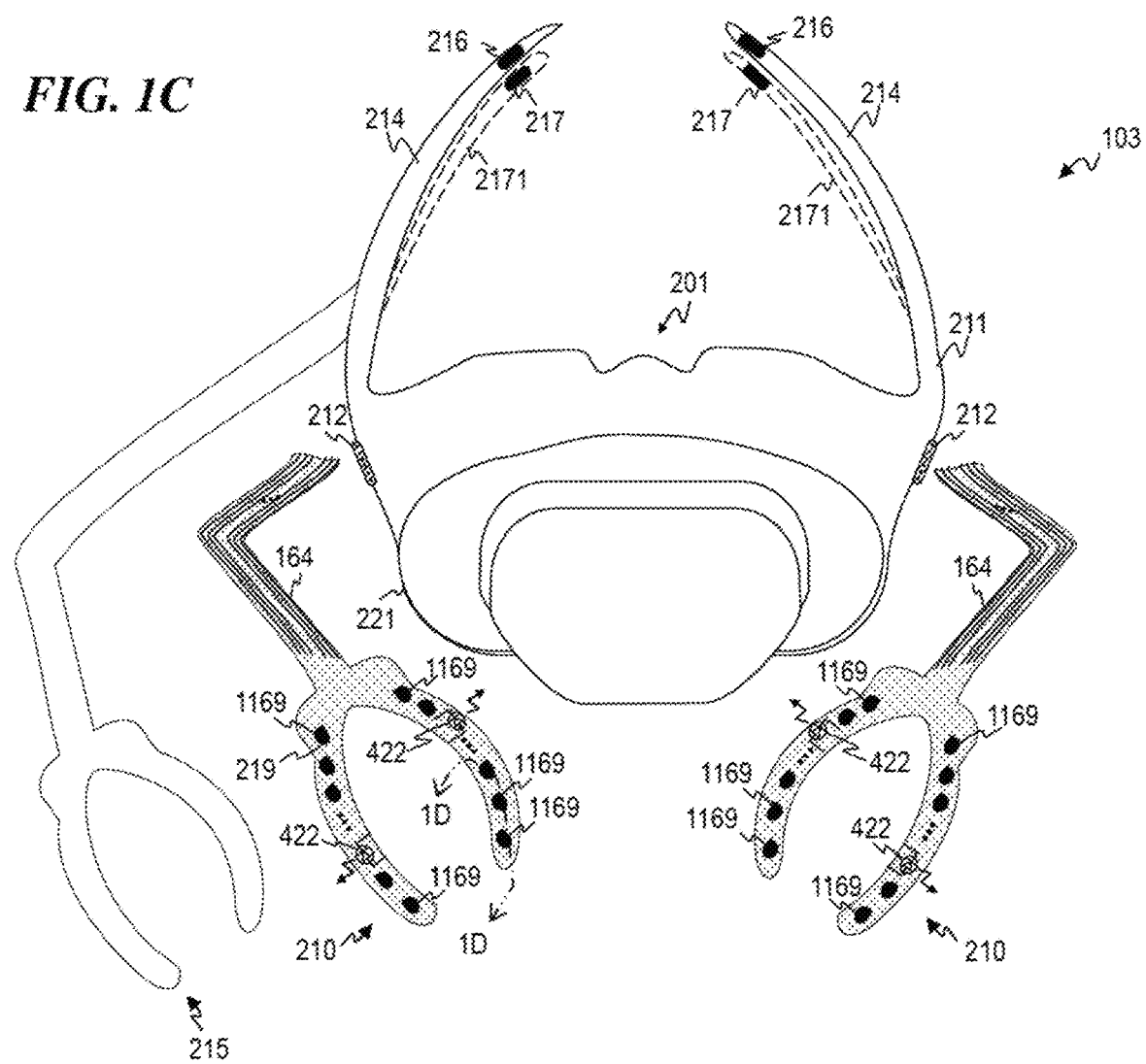
FIG. 1C is a diagram of system 103, according to some embodiments of the present invention.
Figure 1D:
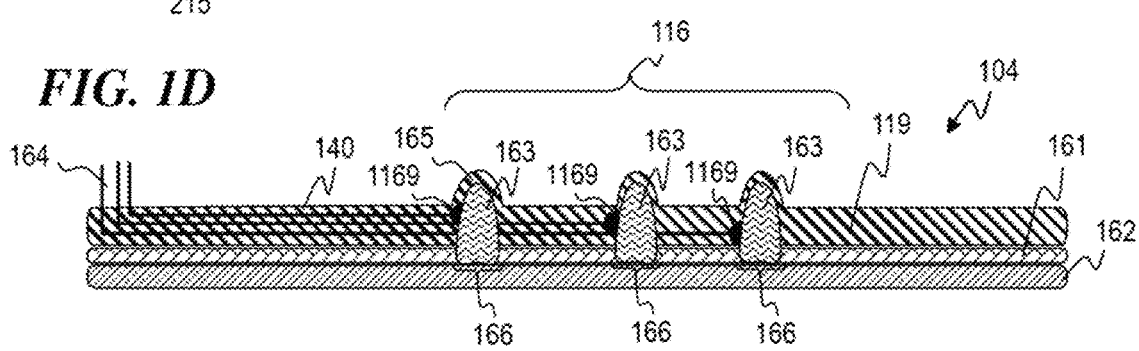
FIG. 1D is a cross-section diagram of and electrode-and-gel system 104, according to some embodiments of the present invention.
Figure 1E:
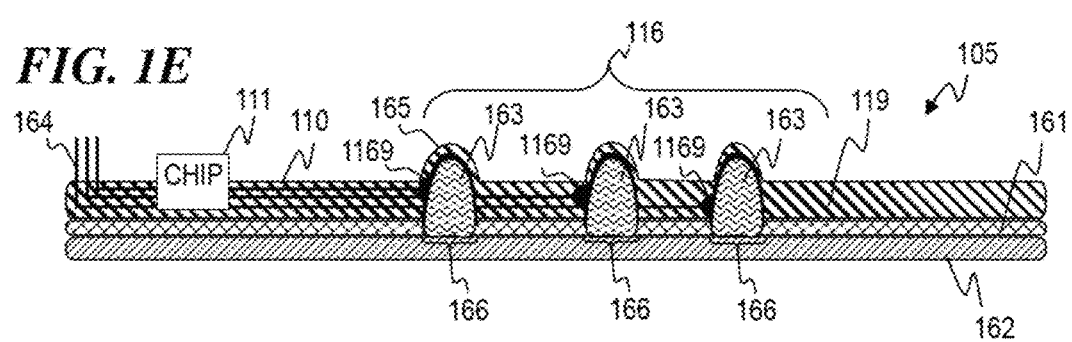
FIG. 1E is a cross-section diagram of an electrode-and-gel system 105, according to some embodiments of the present invention.
Figure 1F:
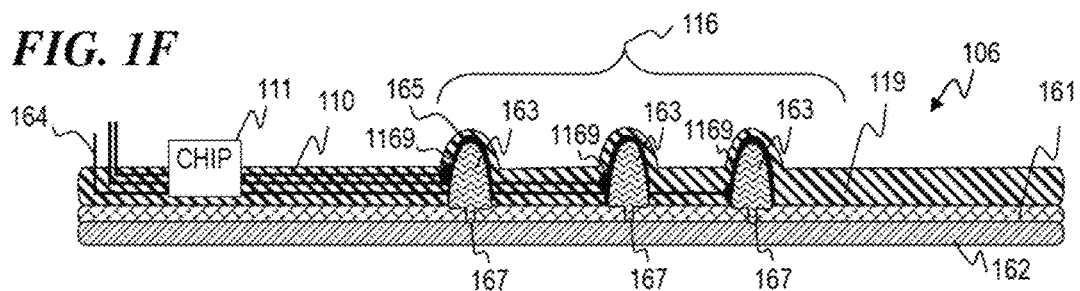
FIG. 1F is a cross-section diagram of an electrode-and-gel system 106, according to some embodiments of the present invention.

As used herein, each generically described "electrode" 1169 includes the electrical conductor (e.g., in some embodiments, a silver-plated and/or other metal conductor) that is in contact with the patient's skin either directly or via an interposed electrically conductive gel, as the area of skin contacted by the electrode and/or gel is limited in lateral extent, e.g., by a pressure-sensitive adhesive 161 (see, e.g., FIG. 1D, FIG. 1E, and/or FIG. 1F).

In some embodiments, system 101 includes a one-use disposable chip-electrode array 110 (which may include one or more integrated-circuit chips 111 and/or other circuitry along with an array of electrodes 1169 on a flexible and/or elastic substrate 119 such as described in U.S. Pat. No. 10,391,312 issued on Aug. 27, 2019 to Blair P. Mowery et al., titled "Apparatus and method for ocular microcurrent stimulation therapy"), a local microprocessor system 120, and a central server 130, wherein chip-electrode array 110 is communicatively coupled to local microprocessor system 120, and local microprocessor system 120 is communicatively coupled to central server 130. In some embodiments, chip-electrode array 110 communicates with local microprocessor system 120 via a wired connection, and/or by a wireless connection such as Bluetooth®, Wi-Fi, infrared light, or the like. In some embodiments, chip-electrode array 110 is powered by a local power source 113 such as a battery, while in other embodiments, power 114 is supplied by a wired connection 164 (see FIG. 1C) or, for example, from power captured from the Wi-Fi signal such as described in United States Patent Application Publication 2017/0300098 by Sen et al. which published on Oct. 19, 2017 with the title "Supplying power to a computer accessory from a captured WIFI signal", and which is incorporated herein by reference. In some embodiments, chip-electrode array 110 includes circuitry such as a microprocessor and signal processor 111 (in some embodiments, microprocessor and signal processor 111 is implemented as a single chip that is integral; in some other embodiments, the circuitry for microprocessor and signal processor 111 is implemented by a plurality of integrated circuit chips). In some embodiments, the plurality 116 of electrodes 1169 are further configured to provide high voltage pulsed current (HVPC) therapy (also referred to as high voltage pulsed direct current or high voltage PDC) in a manner such as described by the publication "Electrical Stimulation Technologies for Wound Healing" (Kloth, Advances in Wound Care, Vol. 3, No. 2, 2014), which is incorporated by reference above. In some embodiments, the plurality 116 of electrodes 1169 are further configured to provide low voltage pulsed current (LVPC) therapy (also referred to as low voltage pulsed direct current or low voltage PDC) in a manner such as described by the publication "Electrical Stimulation Technologies for Wound Healing", which is incorporated by reference above.

In some embodiments, microprocessor and signal processor 111 has an embedded unique serial number (USN) information 158 that uniquely identifies each one of the chip-electrode arrays 110 of a plurality of identical or similar devices in order that quality control is maintained (e.g., by tracking the manufacturing date, batch, version, and the like by the serial number (e.g., in some embodiments, in a device database 133) to help ensure that the device is fresh (not expired) and has up-to-date functionality and features suitable for each particular patient).

In some embodiments, embedded unique serial number information 158 further includes public-key encryption information that is used by server 130 to encrypt data being sent back to chip-electrode array 110, where private-key information needed to decrypt the returned encrypted data 124 from server 130 remains hidden inside microprocessor and signal processor 111 (e.g., in some embodiments, the decryptor is part of data and software in decryptor/pulse-enable-and-control module 112). In some embodiments, the present invention uses public-key encryption private-key decryption methods and systems such as described in United States Patent Application Publication 2008/0028214 by Tafoya et al. or U.S. Pat. No. 6,385,727. Such systems allow the destination system (in this case, the microprocessor and signal processor 111) send out a public key that any source (in this case, server 130) can use to encrypt data that requires the corresponding private key (which is not publicly available) to correctly descript the date returned from the source.

In some embodiments, the returned data 128 contains medically relevant stimulation-control parameters that are customized (potentially differently) for each particular patient or population of patients having a given set of diagnoses and physiological data. In some embodiments, results of each therapy are collected in database 134 and are collectively analyzed to obtain improved future therapy sessions.

By using public-key/private-key communications between the microprocessor and signal processor 111 and server 130, the returned data 124 can be checked for validity or modifications after decryption using the private key data in microprocessor and signal processor chip 111, and the risk of third parties accessing the information, including patient's data, is reduced. In some embodiments, local microprocessor system 120 also receives a unique patient identifier (UPID) 121 associated with the particular patient who is to receive therapy. In some embodiments, the UPID is associated with the patient but in a sense relatively anonymous until used by the server 130 to associate that UPID to the patient PII and medical history 122 in server 130. In some embodiments, local microprocessor system 120 appends (or otherwise combines) the USN 158 and UPID 121, and in some embodiments, encrypts the result via encryptor-encapsulator-transmission circuit 125 and then transmits this information to server 130 (e.g., via a cell phone connection and/or the internet or the like).

In some embodiments, a separate process 122 is used to input more complete patient personal identifying information (PII) and the patient's medical history that, in some embodiments, is encrypted and stored in patient database (PAT DB) 132. In some embodiments, server 130 includes a decryptor/encryptor function 131 that decrypts data from transmitted data 129 to locate and retrieve data associated with the particular patient from patient database 132. In some embodiments, the patient information itself as stored on PAT DB 132 is encrypted, and so when retrieved, the data needs to be decrypted (at least in part) by decryptor 136.

In various embodiments of the present invention, the functions shown in FIG. 1A and FIG. 1B are implemented as a combination of hardware circuitry and software, wherein the some of the various parts of the combination of hardware circuitry and software are implemented in the one-use disposable chip-electrode array 110, in a standalone local microprocessor 120 and/or in one or more mobile communications device(s) such as a cell phone, laptop, iPad® or the like. In some embodiments, some or all of local microprocessor system 120 and/or its function described above is located in a head-worn (goggle-type) apparatus worn by the patient during the procedure. In some embodiments, some or all of local microprocessor system 120 and/or its function described above is located in a bed-side device located near the patient during the procedure. In some embodiments, some or all of local microprocessor system 120 and/or its function described above is located in a cell phone located near the patient during the procedure.

When the USN and UPID information 129 from transmission circuit 125 is received by server 130, the PPID information is correlated to the particular patient to locate and retrieve patient information, history and treatment parameters from PAT DB 132, which together with USN and UPID information 129 are decrypted by decrypt function 136 and the device USN is sent to device and billing database 133.

In some embodiments, device and billing database 133 tracks each device serial number and the associated data regarding the particular chip-electrode array 110, such that system 101 can warn if the particular chip-electrode array 110 has been recalled, is out-of-date (expired due to age), has previously been used (such that re-use of the single-use device is contraindicated), is inappropriate for the particular patient or therapy procedure being requested by the medical professional, or other such problems.

In addition, in some embodiments, device and billing database 133 is used to generate a bill to the patient or their insurance carrier for the use of that device, wherein the bill can thereby reflect the cost of the device as well as the cost of the procedure and other deliverables. The patient information 137 and the device information 139 (e.g., which includes, in some embodiments, the number and configuration of electrodes 1169, the circuitry and software version, and the like) are used to access the proper therapy parameters 138 from the medical results and indication database 134. In some embodiments, those therapy parameters 138 are encrypted (e.g., in some embodiments, using the public key information in USN 158 sent from the particular chip-electrode array 110) by encryption function 135 and transmitted back to local microprocessor system 120, wherein in some embodiments, optional decryption function 123 decrypts at least some of the information for visual and/or audio presentation on display output unit 170 (such as displaying patient name, medical history and the like for review by the attending medical professional supervising the therapy session so that, for example, that medical professional and/or the patient can verify the correct therapy is being applied to the correct patient).

In some embodiments, optional decryption function 123 supplies some or all of the private key information and/or control information 124 needed by circuit 111 to decrypt the control parameters needed for the therapy session. In other embodiments, optional decryption function 123 decrypts only the patient PII (personal identifying information) and history information displayed on display 170, and for the control information, leaves that portion of the payload of data encrypted for the circuit 111 to decrypt and use to control the therapy session. In some embodiments, circuit 111 includes a plurality of transmitter/receivers (that each transmit pulsed or otherwise varying micro-current stimulation to an individual one of electrodes 1169 (wherein a common ground connection is used for the return path of the current) or to a selected pair (or other plurality) of the electrodes that are chosen/determined in order to apply the current along a chosen path from selected source electrode(s) (one or more of the plurality 116 of electrodes 1169) to selected destination electrode(s) (another one or more of the plurality 116 of electrodes 1169). In this way, the selected set paths and the selected sequence of those paths are chosen to target the desired shape and size of the volume of tissue to be receiving the therapy.

Once the integrity of the decrypted version of the returned encrypted data 124 is validated, the payload of the returned data is used to control the transmit portion of transmit/receive (TX/RX) circuitry 115 to deliver micro-stimulation signals that are customized for the particular patient. In some embodiments, the medical indication database provides the initial values for the amplitude, frequency, duty cycle, DC balance, and/or other parameters for the transmit signal sent from transmit/receive (TX/RX) circuitry 115.

In some embodiments, sensed signals 117 from the electrodes 1169 are obtained from the receive portion of transmit/receive (TX/RX) circuitry 115 and are processed by process (e.g., feedback-determining) function 127 and the pulse-adjust results 118 are used to adjust (e.g., change the amplitude, frequency, duty cycle, DC balance, and/or other parameters) the transmit signal sent from transmit/receive (TX/RX) circuitry 115. In some embodiments, the sensed signal is indicative of the impedance/resistance seen by a particular electrode or electrode pair. In some embodiments, the sensed signals are from other electrodes (one or more of the plurality 116 of electrodes 1169) not involved in the transmitted pulse and are indicative of nerve signals or other physiological processes.

In some embodiments, information reflecting the sensed signals and the corresponding stimulation (transmitted) signals on electrodes 1169 is processed and encrypted by function 125 and transmitted to server 130 to be stored in PAT DB 132 to be associated with this patient and this therapy session. In some embodiments, reported results information 126 reflecting information from the patient as to their feeling about the therapy session and the results obtained from the therapy is processed and encrypted by function 125 and transmitted to server 130 to be stored in PAT DB 132 to be associated with this patient and this therapy session.

In some embodiments, results information and therapy session information from a large plurality of patients is processed and aggregated by software in server 130 or operating on data supplied by server 130 to modify the medical indications in database 138 such that over time the therapy for each patient or each type of patient provide improved parameters for future therapy sessions.

FIG. 1B is a block diagram of a system 102 for delivering stimulation signals to at least some of a plurality 116 of electrodes 1169 connected to the skin of a patient and for optionally sensing signals from at least some of the plurality 116 of electrodes 1169, according to some embodiments of the present invention. In some embodiments, much of the functionality of circuit 111 of system 101 has been moved into a local microprocessor system 150, leaving only the electrodes 1169 and their conductor traces on a flexible substrate of one-use disposable electrode array 140. In some embodiments, a unique serial number (USN) is printed on one-use disposable electrode array 140 or its wrapper, which in some embodiments, is machine readable in the form of a bar code or quick-response (QR)-type symbol 145 or the like. In some embodiments, symbol 148 includes the USN as well as a website identifier that is used to retrieve a public-key encryption key from an internet site. In some embodiments, the data and software in decryptor/pulse-enable-andcontrol module 112 functionality that is on chip-electrode array 110 is replaced by data and software in decryptor/pulse-enable-and-control module 152 in local microprocessor system 150. In some embodiments, encryptor-encapsulator-transmission circuit 155 includes the functionality of encryptor-encapsulator-transmission circuit 125 in addition to an imager used to capture the image of QR symbol 145 (e.g., in some embodiments, the camera in a cell phone is used to obtain the data from symbol 145, and the cell phone provides the functionality, or at least part of the functionality of reference numbers 155, 123, 124, 127 and 152). In some embodiments, some of the functionality of local microprocessor system 150 (such as decryptor/pulse-enable-and-control module 152, TX/RX 155, and/or display 170) is located on a head-mounted goggle-type device 201 (such as shown in the diagram in FIG. 1C and FIG. 2), and communicates wirelessly to a cell phone that implements the remainder of functions of local microprocessor system 150. The remainder of the functions shown in FIG. 1B are as shown by like reference numbers in FIG. 1A.

FIG. 1C is a diagram of system 103, according to some embodiments of the present invention. In some embodiments, system 103 includes the goggle-type device 201 (which includes headset frame 211 (which hold the front portion/display frame 221) and temple/ear pieces 214 (which go above the ears of patient 99)), which, in some embodiments, is configured to be placed on the head and connected to the electrodes of one or more one-use disposable chip-electrode array stimulation strip 210 (e.g., an array such as array 110 or array 140 or array 160 or any other electrode strip described herein) that is placed such that a plurality 116 of electrodes 1169 are over both upper and lower eyelids, or on another body part, along with some of its components (e.g., chip 111).

Figure 2A:
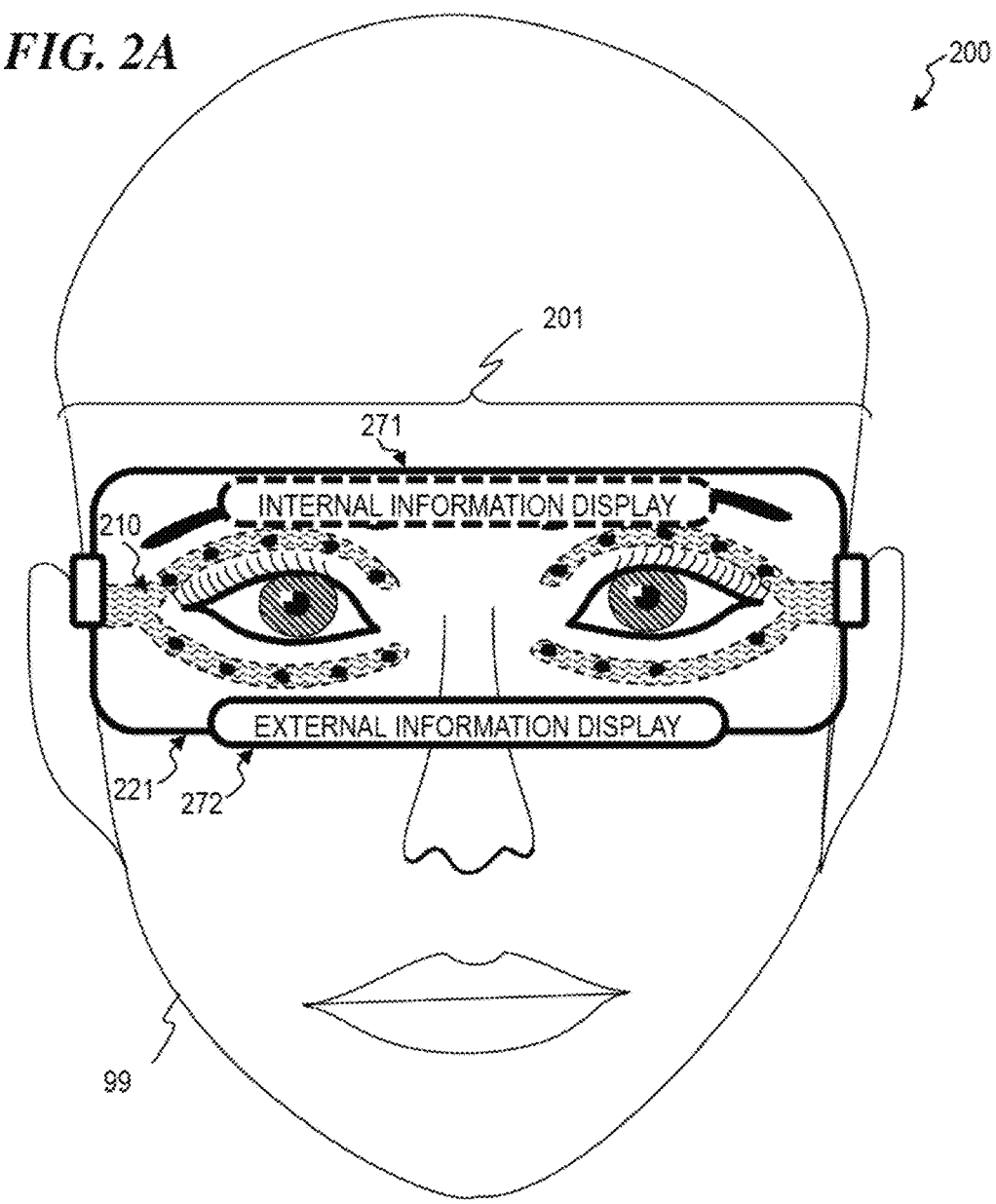
FIG. 2A is a schematic diagram of a stimulation system 200 showing device 201 in place on the head of a patient 99, according to some embodiments of the present invention.

In some such embodiments, electrodes on stimulation strips 210 are coupled to goggle-type device 201 such that display-screen frame 221 of device 201 covers stimulation strips 210 and help hold stimulation strips 210 against the skin of patient 99 during use (e.g., as shown by frame 221 and strips 210 in FIG. 2A).

In some embodiments, electrode array stimulation strip 210 further includes one or more light emitters 422 (such as LEDs or the like). In some embodiments, electrode-array stimulation strip 210 includes unique serial-number information 158 that is embedded in one or more integrated circuit chips 111. In other embodiments, electrode-array stimulation strip 210 and/or its wrapper (not shown, but similar in concept to a bandage cover that keeps the bandage sterile) includes information that is machine readable, e.g., in the form of an optically readable bar code/UPC code such as quick-response (QR)-type symbol 145 or the like. In some embodiments, system 103 further includes headset frame 211, connector 212 (e.g., in some embodiments, an electrical socket having a plurality of electrical contact points to receive the edge connector conductors 196 (see, FIG. 1G) of chip-electrode array stimulation strip 210) between conductors to the electrodes 1169 and the headset frame 211, and electrode skin-contact points 219, numbered from as few as two (2) per electrode array stimulation strip 210 to as many as ten (10) or more (in some embodiments, as shown in FIG. 1C, there are ten or more electrodes 1169 to contact corresponding skin-contact points 219 per eye). In some embodiments, the electrode skin-contact points 219 are each larger in area than the corresponding electrodes 1169 (such as shown in FIG. 1D, which shows the gel contact area 166 under gel 163 being larger than the electrode 1169); in other embodiments, the electrode skin-contact points 219 are each the same size in area as the corresponding electrodes 1169 (such as shown in FIG. 1E, which shows the gel contact area 166 under gel 163 being about the same lateral size as the electrode 1169), and in still other embodiments, the electrode skin-contact points 219 are each smaller in area than the corresponding electrodes 1169 (such as shown in FIG. 1F, which shows the gel contact area 167 under gel 163 being smaller than the electrode 1169). In some embodiments, system 103 further includes side temple piece 214 that goes around the side of the head (e.g., in some embodiments, to hook over the patient's ear as do eyeglasses), optional extended lens cover "arm" 215, which, in some embodiments, is used to adjust the contact pressure over the electrodes of the various contact points 219 around the eye socket, and zero or more optional grounding electrode(s) 216 that, in some embodiments, provides a ground connection between headset frame 211 and the patient's body. Section line 1D-1D of FIG. 1C shows the location of the cross-section of FIG. 1D. In some embodiments, not shown in FIG. 1C, a lens cover arm 215 is located on both sides of headset frame 211. In some embodiments, one or more ground electrodes 216 is/are included on the inner surface of the temple pieces 214. In other embodiments, a ground electrode conductor 217 is included as a conductor on a disposable film 2171 electrically connected to and covering the skin-contact portions of the temple pieces to touch the patient's skin above the ear.

FIG. 1D is a cross-section diagram (along section line 1D-1D of FIG. 1C) of an electrode-and-gel system 104, according to some embodiments of the present invention. In some embodiments, electrode-and-gel system 104 includes one-use disposable electrode array 140 having a skin-facing adhesive 161 on flexible and/or elastic substrate 119, wherein the adhesive 161 and electrically conductive gel 163 are covered by a removable cover 162. In some embodiments, each of the plurality 116 of conductive electrodes 1169 is formed (e.g., by printing, plating and/or etching) on a pocket 165 formed in substrate 119, wherein each pocket 165 contains a selected amount of electrically conductive gel 163 held in place by adhesive 161 and cover 162, until the cover 162 is removed so that one-use disposable electrode array 140 can be applied to the skin of the patient with each portion of gel 163 and its electrode being electrically isolated from the other electrodes and their gel. In some embodiments, each electrode 1169 is connected to a corresponding one of a plurality of electrical connectors 164 to send and receive signals and/or power to and from local microprocessor system 150 (see FIG. 1B).

FIG. 1E is a cross-section diagram of an electrode-and-gel system 105, according to some embodiments of the present invention. In some embodiments, electrode-and-gel system 105 includes one-use disposable chip-electrode array 110 having a skin-facing adhesive 161 on flexible and/or elastic substrate 119, wherein the adhesive 161 and electrically conductive gel 163 are covered by a removable cover 162. In some embodiments, each of the plurality 116 of conductive electrodes 1169 is formed (e.g., by printing, plating and/or etching) on pocket 165 formed in substrate 119 (e.g., in some embodiments, by embossing the polymer substrate 119), wherein each pocket 165 contains a selected amount of electrically conductive gel 163 held in place by adhesive 161 and cover 162, until the cover 162 is removed so that one-use disposable chip-electrode array 110 can be applied to the skin of the patient with each portion of gel 163 and its electrode being electrically isolated from the other electrodes and their gel. In some embodiments, each electrode 1169 is connected to a corresponding TX/RX 115 of chip 111, and chip 111 communicates information signals 117, 118, 158 and 124 via a plurality of electrical connectors 164 or, in other embodiments, wirelessly by Bluetooth® or Wi-Fi, to local microprocessor system 120 (see FIG. 1A).

FIG. 1F is a cross-section diagram of an electrode-and-gel system 106, according to some embodiments of the present invention. In some embodiments, electrode-and-gel system 106 is substantially similar to electrode-and-gel system 105, except that electrode skin-contact points 219 are each smaller in area than the corresponding electrodes 1169 (e.g., in some embodiments, gel contact area 167 under gel 163 is smaller than electrode 1169). In some such embodiments, the lateral size of each opening in adhesive layer 161 is made of a desired size to limit the area of skin contacted by gel 163 to "pinpoint" the electrical contact to the patient's skin. In some such embodiments, to the area of a 1.6-mm-diameter circle (i.e., a circular area of about 2 mm$^2$) or a square that is 1.4-mm on each side (i.e., a square area also of about 2 mm$^2$), or other suitable shape and skin-contact area (for example, in other embodiments, areas of 1 mm$^2$ (e.g., a square opening in adhesive 161 of 1 mm by 1 mm), 3 mm$^2$, 4 mm$^2$ (e.g., a square opening in adhesive 161 of 2 mm by 2 mm), 5 mm$^2$, 6 mm$^2$ (e.g., a rectangular opening in adhesive 161 of 2 mm by 3 mm), 8 mm$^2$ (e.g., a triangular opening in adhesive 161 of 4 mm-wide base by 4 mm height), 9 mm$^2$ (e.g., a square opening in adhesive 161 of 3 mm by 3 mm), 16 mm$^2$ (e.g., an opening in adhesive 161 of 4 mm by 4 mm), 20 mm$^2$, 25 mm$^2$ (e.g., a square opening in adhesive 161 of 5 mm by 5 mm), 36 mm$^2$ (e.g., a square opening in adhesive 161 of 6 mm by 6 mm), 49 mm$^2$ (e.g., a square opening in adhesive 161 of 7 mm by 7 mm), or other suitable-sized opening). In some other such embodiments, the lateral size of each opening in the bottom of substrate 119 and/or adhesive 161 is made of a desired size to limit the area of skin contacted by gel 163.

Figure 1G:
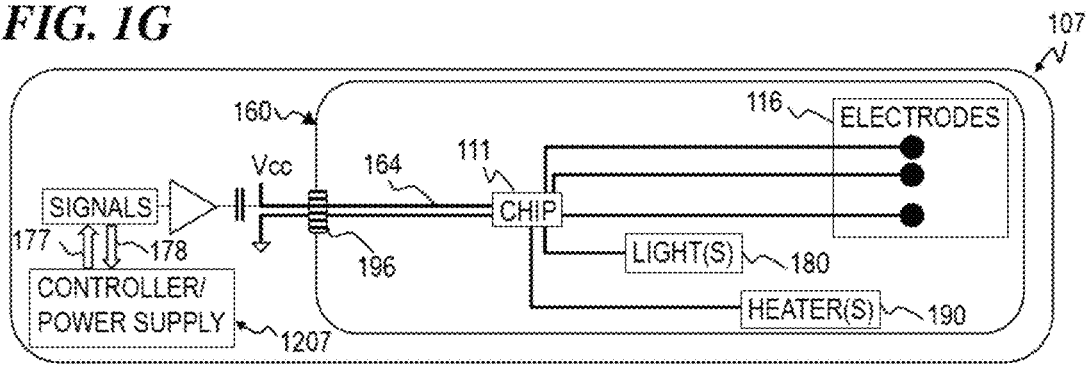
FIG. 1G is a block diagram of system 107 having a self-contained controller with a stimulation strip 160, according to some embodiments of the present invention.

FIG. 1G is a block diagram of system 107 having a self-contained controller with a stimulation strip 160, according to some embodiments of the present invention. In some embodiments, stimulation strip 160 is substantially similar to chip-electrode array 110 and/or disposable electrode array 140 except that stimulation strip 160 further includes one or more individually controllable light emitters 180 and, in some embodiments, one or more individually controllable heat sources 190. In some embodiments, light emitters 180 are configured to provide light-stimulation therapy to the patient (e.g., in some embodiments, combined optical and electrical stimulation to nerves of the patient in a manner such as described in U.S. Pat. No. 7,883,536 titled "Hybrid optical-electrical probes", U.S. Pat. No. 8,160,696 titled "Nerve stimulator and method using simultaneous electrical and optical signals", and/or U.S. Pat. No. 8,996, 131 title "Nerve stimulator and method using simultaneous electrical and optical signals", each of which is incorporated by reference above). In other embodiments, the light-stimulation therapy includes light pulses to stimulate the retina optical receptors in the patient's eye(s). In still other embodiments, an internal display such as internal information/stimulation display 271 as shown in FIG. 2A is controlled to provide a light pattern that moves across the patient's field of view to cause the patient to move their eyes to follow the pattern, in order that the eyes are in different selected spatial orientations relative to the electrical stimulation so that different portions of the patient's anatomy in and around the eyes are stimulated more effectively. In some embodiments, internal information/stimulation display 271 provides a background color to provide a relaxing ambiance to patient 99. In some embodiments, internal display 271 also provides information to patient 99 indicating the time elapsed or remaining duration of the therapy session and/or other information that may be useful (e.g., informative), interesting (e.g., entertaining), or relaxing (e.g., meditative) to patient 99 (e.g., graphical or text data).

In some embodiments, heat sources 190 are configured to provide heat therapy to the patient (e.g., in a manner such as described in U.S. Patent Application 2010/0049180 titled "System and method for conditioning animal tissue using laser light", and/or U.S. Pat. No. 8,996,131, both of which are incorporated by reference above). In some embodiments, rather than using laser-induced heating as described in U.S. Patent Application 2010/0049180, the present invention uses resistive heating elements in the stimulation strips 210 and/or goggle apparatus 201 to heat the patient's skin to a temperature of about 42 C to 43 C (42-43 degrees Celsius (centigrade)) in order to induce the patient's tissue to generate heat-shock protein 70 (hsp70) near the patient's eyes to induce a healing response. In some embodiments, stimulation strip 160 is one of two stimulation strips (one for each eye) and both stimulation strips are coupled to a goggle-type device 201 in a manner similar to chip-electrode-array stimulation strips 210 of FIG. 1C. In some embodiments, stimulation strip 160 is one of two stimulation strips (one for each eye), and the two stimulation strips are coupled to the eyes of the patient without using a goggle-type device 201.

In some embodiments, stimulation strip 160 provides a combination of microstimulation therapy and light-stimulation therapy (in some such embodiments, each therapy is delivered to the patient simultaneously; in other such embodiments, each therapy is delivered to the patient in a sequential manner such that each therapy begins at a different start time). In some embodiments, stimulation strip 160 provides a combination of microstimulation therapy, light-stimulation therapy, and heat therapy (in some such embodiments, each therapy is delivered simultaneously with the other therapies; in other such embodiments, the combination of therapies is delivered sequentially such that at least two of the three therapies begin at different start times). In some embodiments, stimulation strip 160 is one of two stimulation strips (one for each eye), and microcurrent stimulation therapy, light-stimulation therapy, and/or heat therapy is delivered to both eyes simultaneously. In other embodiments, the one or more therapies (among microcurrent stimulation therapy, light-stimulation therapy, and heat therapy) delivered to the first eye begins at a different start time than the one or more therapies delivered to the second eye (sequential therapy delivery).

In some embodiments, system 107 includes a controller/power supply 1207 that is configured to control delivery of the microcurrent stimulation therapy, light-stimulation therapy, and/or heat therapy (also referred to collectively as the stimulation therapies). In some embodiments, controller/power supply 1207 is located on the patient (e.g., in a goggle-type device such as device 201, in a device that is placed on (e.g., adhered to) the temple of the patient, or in any other suitable location on the patient). In some embodiments, controller/power supply 1207 is configured to send control signals 177 to stimulation strip 160 and receive feedback signals 178 from stimulation strip 160 via wired connections 164 with chip 111.

Figure 1H:
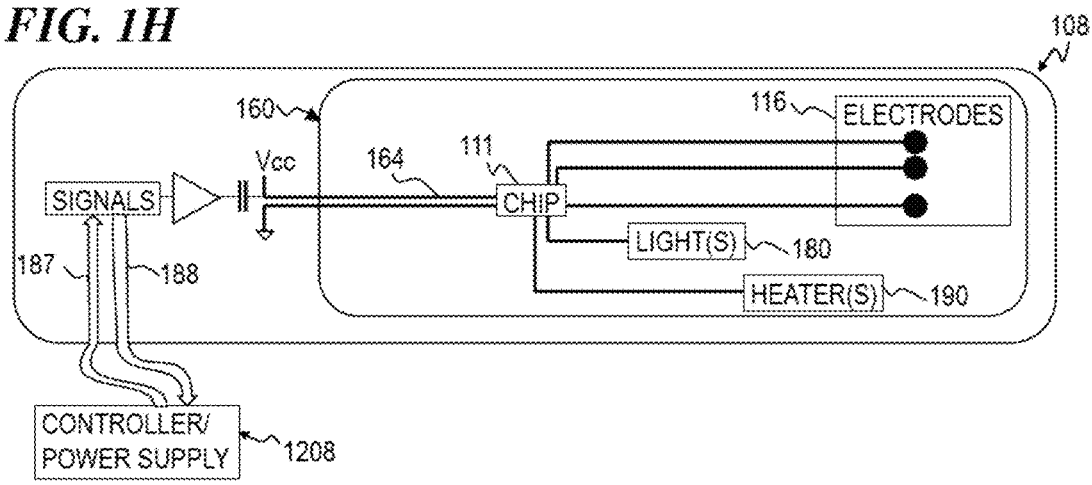
FIG. 1H is a block diagram of system 108 having a partially-contained wire-connected controller with a stimulation strip 160, according to some embodiments of the present invention.

FIG. 1H is a block diagram of system 108 having a partially-contained wire-connected controller with a stimulation strip 160, according to some embodiments of the present invention. In some embodiments, system 108 includes a controller/power supply 1208 that is configured to control delivery of the microcurrent stimulation therapy, light-stimulation therapy, and/or heat therapy (also referred to collectively as the stimulation therapies). In some embodiments, controller/power supply 1208 is located separately from the patient (e.g., in a desktop computer or other suitable control device that is not located on the patient). In some embodiments, controller/power supply 1208 is configured to transmit control signals 187 to stimulation strip 160 and receive feedback signals 188 from stimulation strip 160 via wired connections carrying signals 187/188.

Figure 1I:
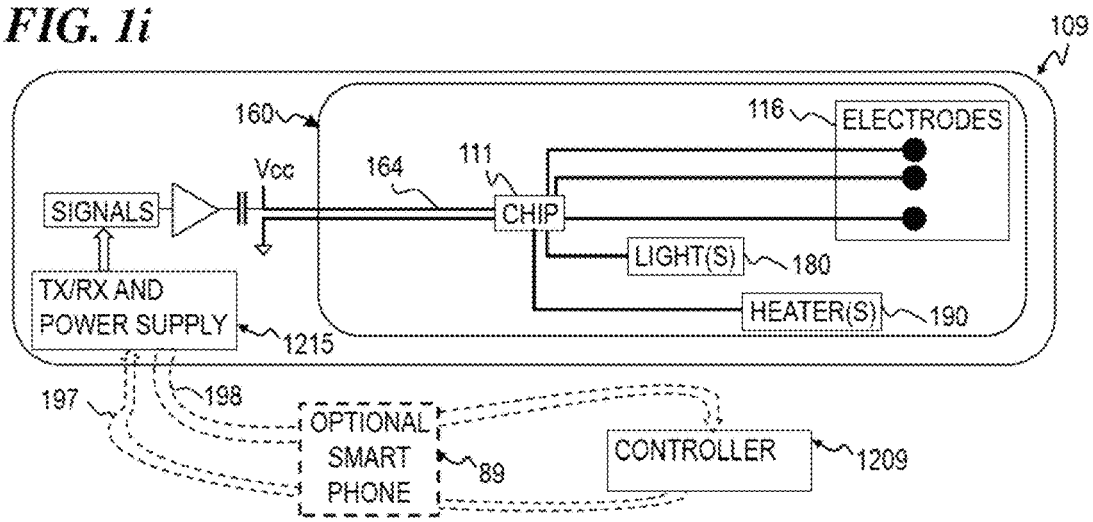
FIG. 1i is a block diagram of system 109 having a partially-contained wireless-connected controller with a stimulation strip 160, according to some embodiments of the present invention.

FIG. 1i is a block diagram of system 109 having a partially-contained wireless-connected controller with a stimulation strip 160, according to some embodiments of the present invention. In some embodiments, system 109 includes a controller/power supply 1209 that is configured to control delivery of the stimulation therapies, and, in some embodiments, controller/power supply 1209 is located separately from the patient and is configured to communicate wirelessly with stimulation strip 160. In some such embodiments, chip 111 is operatively coupled to a transmit/receive (Tx/Rx) module/power supply 1215 that is configured to communicate wirelessly with controller/power supply 1209 (in some embodiments, module 1215 is located on the patient). In some embodiments, controller/power supply 1209 is configured to transmit control signals to stimulation strip 160 and receive feedback signals from stimulation strip 160 via wireless connections 197/188. In some embodiments, controller 1209 is operated via a smart phone 89.

FIG. 2A is a schematic diagram of a stimulation system 200 showing device 201 in place on the head of a patient 99, according to some embodiments of the present invention. In some embodiments, display-screen frame 221 includes an internal information and/or stimulation display 271 that can only be seen by patient 99 when device 201 is on patient 99, and an external information display 272 that cannot be seen by patient 99 when device 201 is on patient 99. In some embodiments, external information display 272 is used to display information (e.g., stimulation level (i.e., intensity of stimulation), stimulation type (e.g., light, microcurrent, and/or heat), stimulation time elapsed and/or time remaining, skin temperature, skin impedance level, pressure on the electrodes, and the like) to a medical professional/technician or other person that is assisting/directing the delivery of the stimulation therapies from device 201 to patient 99. In some embodiments, internal information and/or stimulation display 271 is used to display information (e.g., stimulation level (i.e., intensity of stimulation), stimulation type (e.g., light, microcurrent, and/or heat), stimulation time elapsed and/or time remaining, skin temperature, skin impedance level, pressure on the electrodes, and the like) to the patient. In some embodiments, internal information and/or stimulation display 271 is used to additionally or instead display visual stimulation to the patient such as one or more points of light that move across the patient's visual field to urge the patient to move their eyes to follow the movement of the point(s) of light to orient the eyes in different positions during the therapy such that the electric field generated by the electrodes 1169 stimulate one or more selected volumes of tissue in and/or around the eye. In other embodiments, internal information and/or stimulation display 271 is used to additionally or instead display various colors (such as red wavelengths of 600 nm to about 700 nm which might trigger the release of hormones such as melatonin).

Figure 2B:
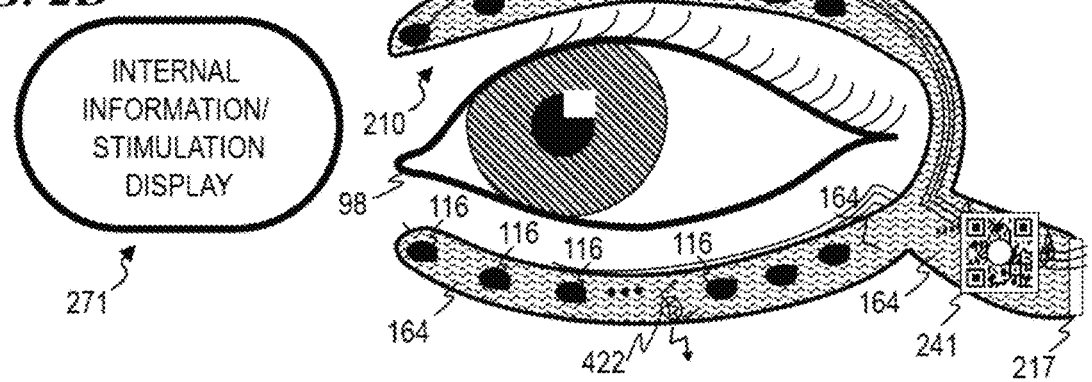
FIG. 2B is a schematic diagram of a stimulation system 202 showing how the internal information display 271 of FIG. 2A is visible to the eye 98 of patient 99, according to some embodiments of the present invention.

FIG. 2B is a schematic diagram of a stimulation system 202 showing how the internal information display 271 of FIG. 2A is visible to patient 99, according to some embodiments of the present invention. In some embodiments, system 203 includes chip-electrode array strip 210 in place around an eye 98 of patient 99, where the internal information display 271 of display-screen frame 221 is visible to eye 98.

Figure 2C:
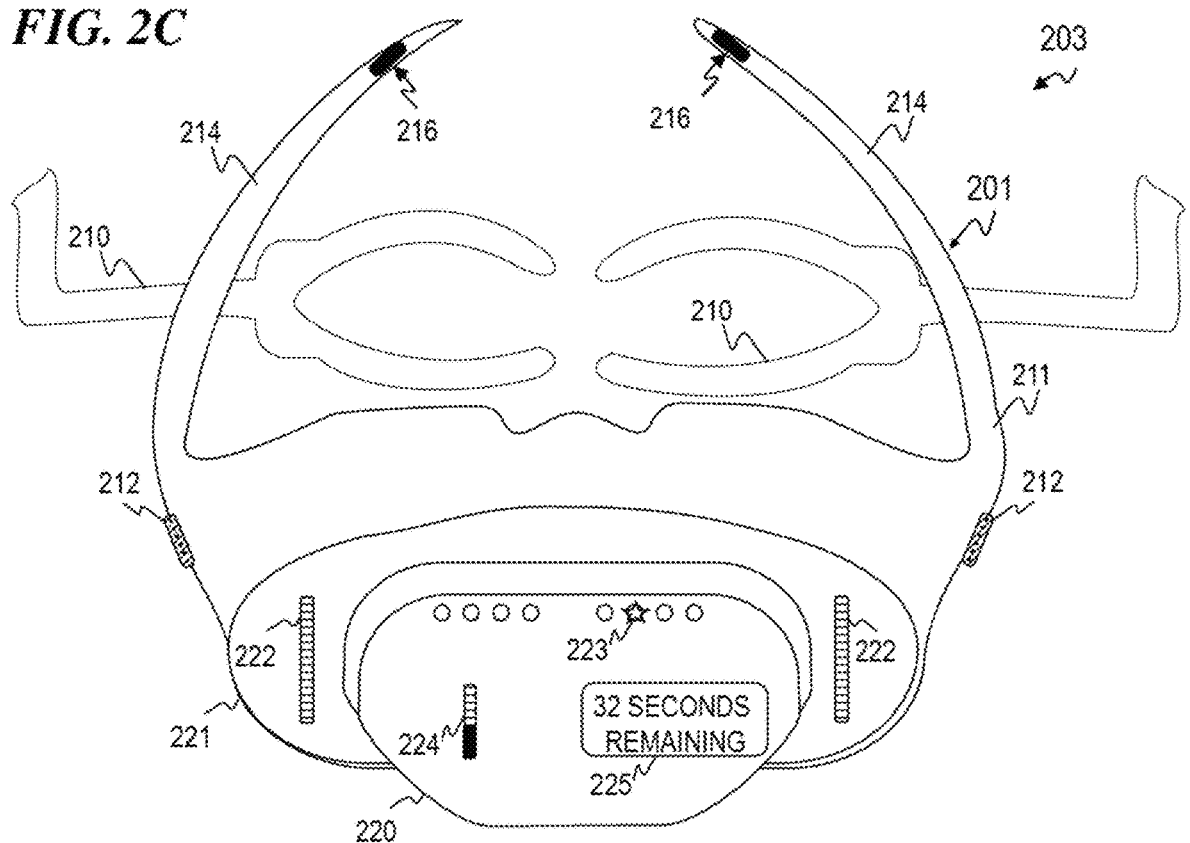
FIG. 2C is a diagram of system 203, according to some embodiments of the present invention.

FIG. 2C is a diagram of goggle-type device 203 showing various visual indicators 222 provided by device 201, according to some embodiments of the present invention. In some embodiments, device 201 includes a visual screen 220, incorporated into headset frame 211, indicating a display of the various elements of information visible on screen at any one time. In some embodiments, device 201 further includes a display-screen frame 221 that includes, for example, two (2) to ten (10) lights 222 on either or both sides of the display screen frame 221 (upper plus lower). In some embodiments, lights 222E are also configured to provide a confirmation or indication that the contact points of the electrode are functioning properly and delivering the appropriate level of current chosen to stimulate the eye. In some embodiments, display 220 includes light(s) 223 that indicate which electrode contact point(s) 219 is currently active in session, light(s) or display 224 that indicates the level of stimulation, and light(s) 225 or display that indicates the stimulation time that has elapsed or the time that remains to complete the present therapy session.

Figure 2D:
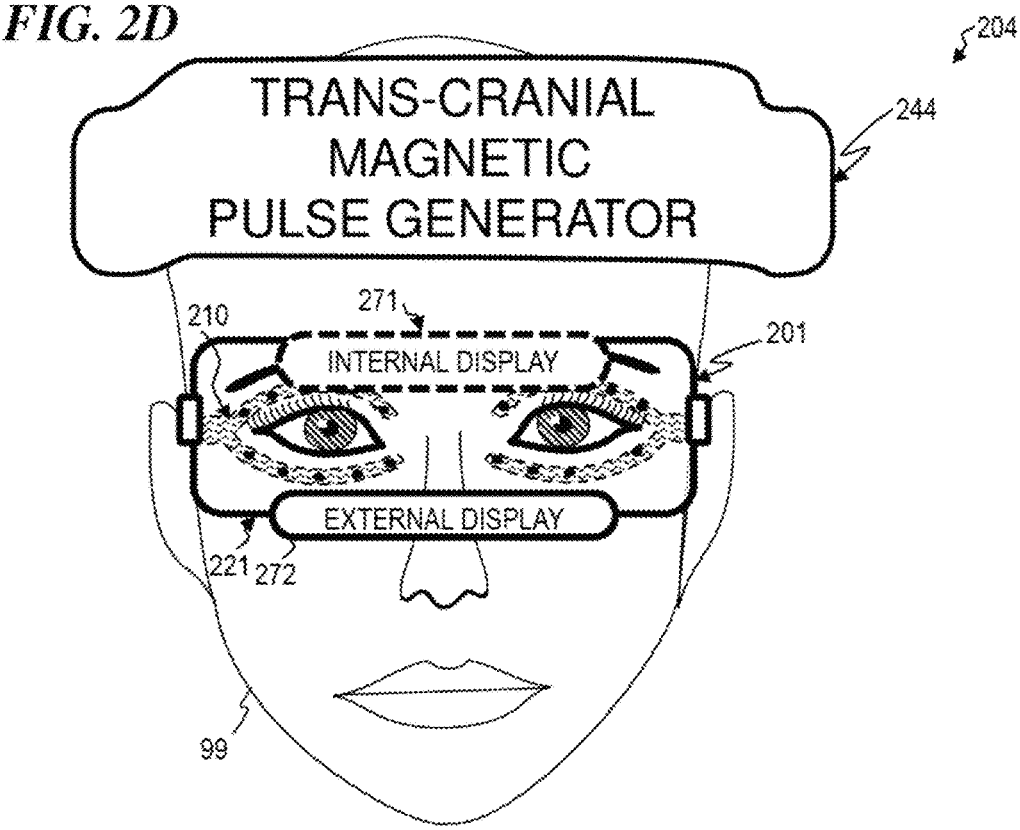
FIG. 2D is a schematic diagram of a stimulation system 204 showing device 201 in place on the head of a patient 99, in addition to TCMPG (trans-cranial magnetic pulse generator) 244, according to some embodiments of the present invention.

FIG. 2D is a schematic diagram of a stimulation system 204 showing device 201 in place on the head of a patient 99, in addition to TCMP (trans-cranial magnetic pulse) generator 244, according to some embodiments of the present invention. In some embodiments, TCMP generator 244 is substantially similar to the device described in the Mayo Clinic publication titled "Transcranial magnetic stimulation", which is incorporated by reference above. In some embodiments, the therapy provided by TCMP generator 244 is referred to as Pulsed Electromagnetic Field (PEMF) therapy. In some embodiments, TCMP generator 244 uses a device such as described in U.S. Pat. No. 7,239,910 titled "Methods and devices for transcranial magnetic stimulation and cortical cartography," but with the method described therein modified to obtain the spatial structure of one or both of the eyes of patient 99 and the surrounding tissue including brain tissue. In some embodiments, a magnetic pulse is generated by TCMP generator 244 to focus the TCMP on a selected region of the eye (in some embodiments, stimulating and/or inhibiting at least one point or area of the eye using at least one TCMP generator stimulation device 244, wherein: the spatial structure of the head or eye is recorded; a three-dimensional simulation model of the structure of the eye is generated from the recording of the spatial structure of the eye region; and the TCMP generator stimulation device 244 is arranged relative to the head or eye using the three-dimensional simulation model of the structure of the eye, such that the at least one point or area of the eye can be stimulated using the TCMP generator stimulation device 244), and is applied either simultaneously with, or alternating with, the adjustable electrical stimulation (and/or adjustable thermal stimulation and/or adjustable pressure/vibration stimulation) therapy as described elsewhere herein.

FIG. 2E is a block diagram of a system 101' for delivering stimulation signals to at least some of a plurality 116 of electrodes 1169 connected to the skin of a patient and for optionally sensing signals from temperature sensor(s) and/or pressure sensor(s), according to some embodiments of the present invention. In some embodiments, system 101' is substantially similar to system 101 of FIG. 1A, but with the addition of additional sensors and/or controllers and actuators to adjust temperature, pressure (including variable pressure and/or haptic vibration), light, aroma, and the like that can be added to or part of the stimulation strip 110'. In some embodiments, a set 176 of one or more electrical coils 1769 is manufactured on stimulation strip 210 (rather than using a separate TCMP generator stimulation device 244 as shown in FIG. 2D), wherein the electrical coils 1769 are driven with an electrical pulse to generate a TCMP magnetic pulse to the underlying tissue.

Figure 3:
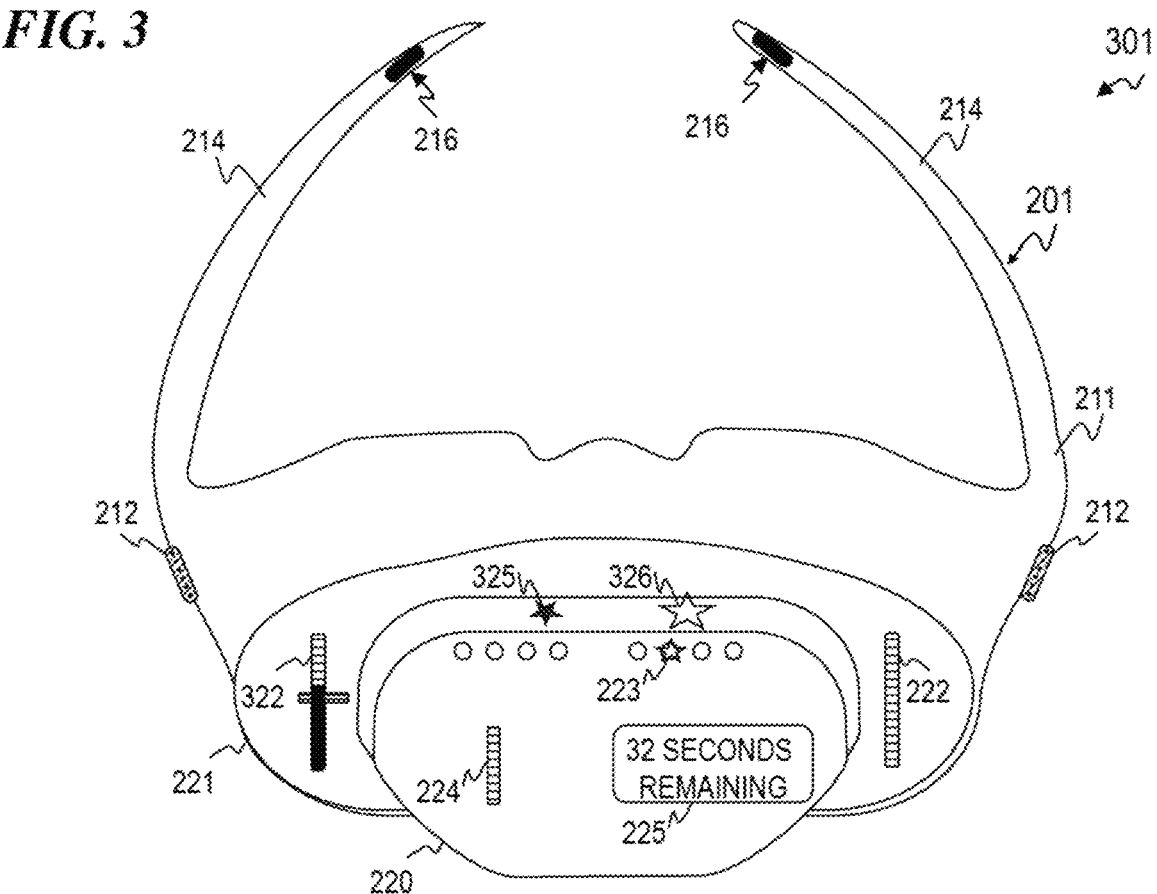
FIG. 3 is a diagram of system 301, according to some embodiments of the present invention.

FIG. 3 is a diagram of a goggle-type device 301, according to some embodiments of the present invention. In some embodiments, device 301 includes lights on the headset frame (e.g., headset frame 211) to help the clinician know the status of treatment. In some embodiments, light or display 322 indicates if there is stimulation impedance level and whether that level meets stimulation requirements for a therapy session, and if the stimulation level chosen is being properly delivered; in addition, some embodiments include ON/OFF lights. In some embodiments, the OFF light 325 activates to indicate that the treatment session has finished. In some embodiments, the ON light 326 illuminates when the treatment session is in process. There may also be individual treatment "session" lights (one per each electrode stimulation point; e.g., light(s) 223). In some embodiments, the session lights illuminate according to the specific treatment point being stimulated at that particular moment of the therapy, enabling the clinician to know exactly where in the treatment process the patient was.

Figure 4A:
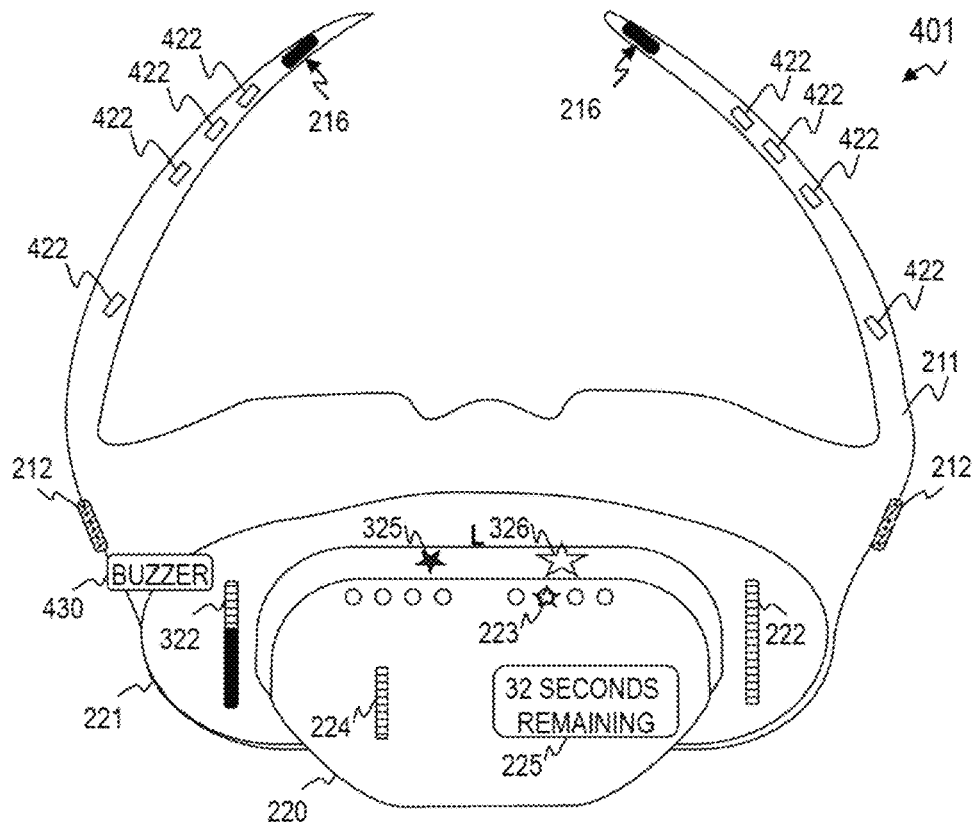
FIG. 4A is a diagram of system 401, according to some embodiments of the present invention.

FIG. 4A is a diagram of a goggle-type device 401, according to some embodiments of the present invention. In some embodiments, device 401 includes a light filament 422 (e.g., LEDs, optical fibers, low-power laser diodes, or other light source) that is used to provide indicating and/or soothing ambient light to the patient. In some embodiments, one or more light filaments 422 is/are located on the interior side of the headset frame (e.g., headset frame 211) such that light is projected toward the patient from light filament 422. A single or a double filament line may be used for filament 422. In some embodiments, device 401 further includes a vibration "filament", actuator or buzzer 430 that is embedded in the headset frame (e.g., headset frame 211).

Figure 4B:
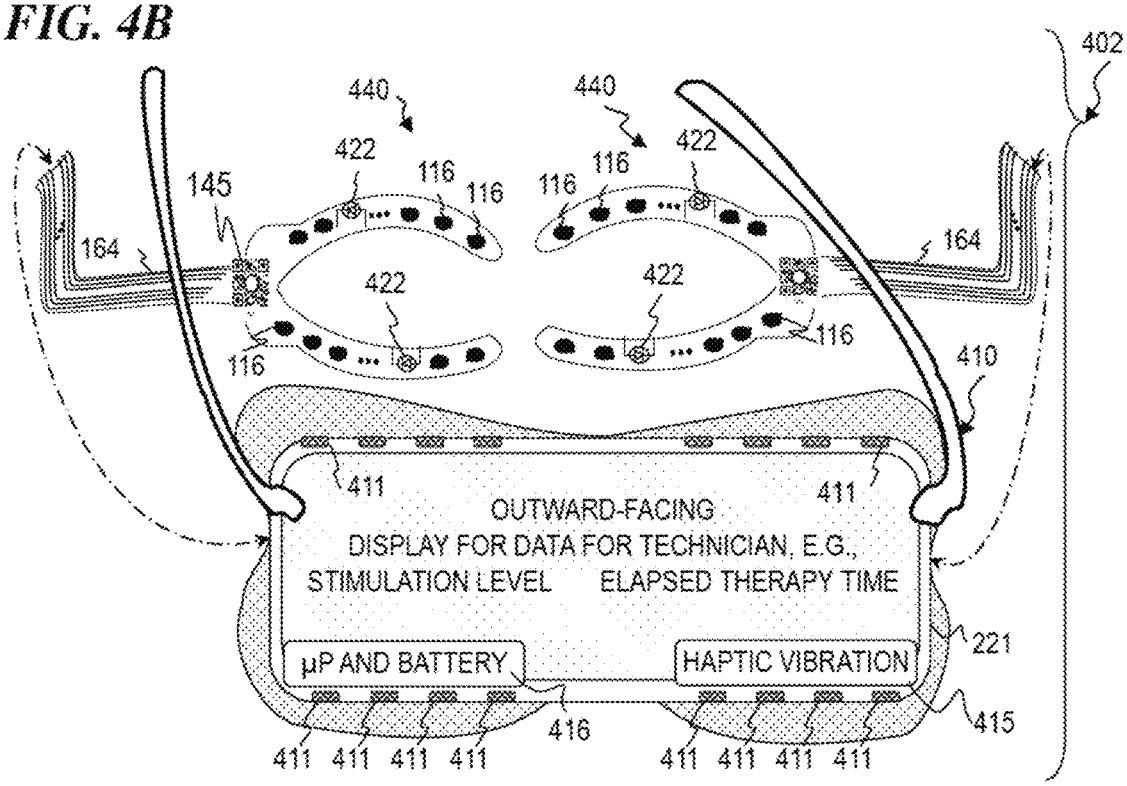
FIG. 4B is a diagram of system 402, according to some embodiments of the present invention.

FIG. 4B is a diagram of a system 402, according to some embodiments of the present invention. In some embodiments, the present invention uses one, two or more electrode strips 440 such as one-use disposable chip-electrode array 110 (as described above for FIG. 1A) or one-use disposable electrode array 140 (as described above for FIG. 1B) or one-use stimulation strip 160 (as described above for FIG. 1G, FIG. 1H, and FIG. 1i) that are electrically connected to headset 410. In some embodiments, headset 410 is worn by the patient during the therapy session, and includes the functionality as described above for local microprocessor system 120 (as described above for FIG. 1A) and/or local microprocessor system 150 (as described above for FIG. 1B). In addition, in some embodiments, headset 410 includes one or more LEDs 411 that provide flashes or other light signals (for the patient to perceive even when their eyes are closed, and/or the medical professional who is administering the micro-current electrical stimulation therapy) to indicate that the therapy is working and/or to provide other feedback or information to the patient or medical professional. Also, in some embodiments, headset 410 includes one or more haptic vibration devices 415 that provide vibration through the frame of headset 410 or by direct contact to the patient's skin (for the patient to perceive even when their eyes are closed, and/or via wireless transmission to a wrist-worn fitness monitor, Apple Watch®, Fitbit® or the like such that the medical professional who is administering the micro-current electrical stimulation therapy is notified to look at information displayed on display 272 of frame 221 or other notification) to indicate that the therapy is working and/or to provide other feedback or information to the patient or medical professional. In some embodiments, headset 410 includes an on-board microprocessor and battery 416 to support the functionality for local microprocessor system 120 (as described above for FIG. 1A) and/or local microprocessor system 150 (as described above for FIG. 1B). In some embodiments, one-use disposable chip-electrode arrayX(as described above for FIG. 1A) or one-use disposable electrode array 140 (as described above for FIG. 1B) or one-use stimulation strip 160 (as described above for FIG. 1G, FIG. 1H, and FIG. 1i) further include one or more LEDs 422 to provide an indication of functionality (e.g., that the electrode array 110 or 140 or 160 is properly electrically connected to headset 410) and/or an indication that therapy is underway. In some embodiments, power for electrode array 440 is supplied by a wired power connection 114 among the electrical conductors 164 on a flexible substrate along with the connector that lead to electrodes 116. In some embodiments, electrode array 110 or 140 has an adhesive layer 161 (see FIG. 1D) to hold the electrode array 110 or 140 to the patient's skin. In some embodiments, electrode array 110 or 140 or 160 is first adhered to the patient in the desired location, then the patient puts on headset 410 and the electrode arrays 110 or 140 or 160 are connected to a corresponding jack or other electrical connection.

Figure 5:
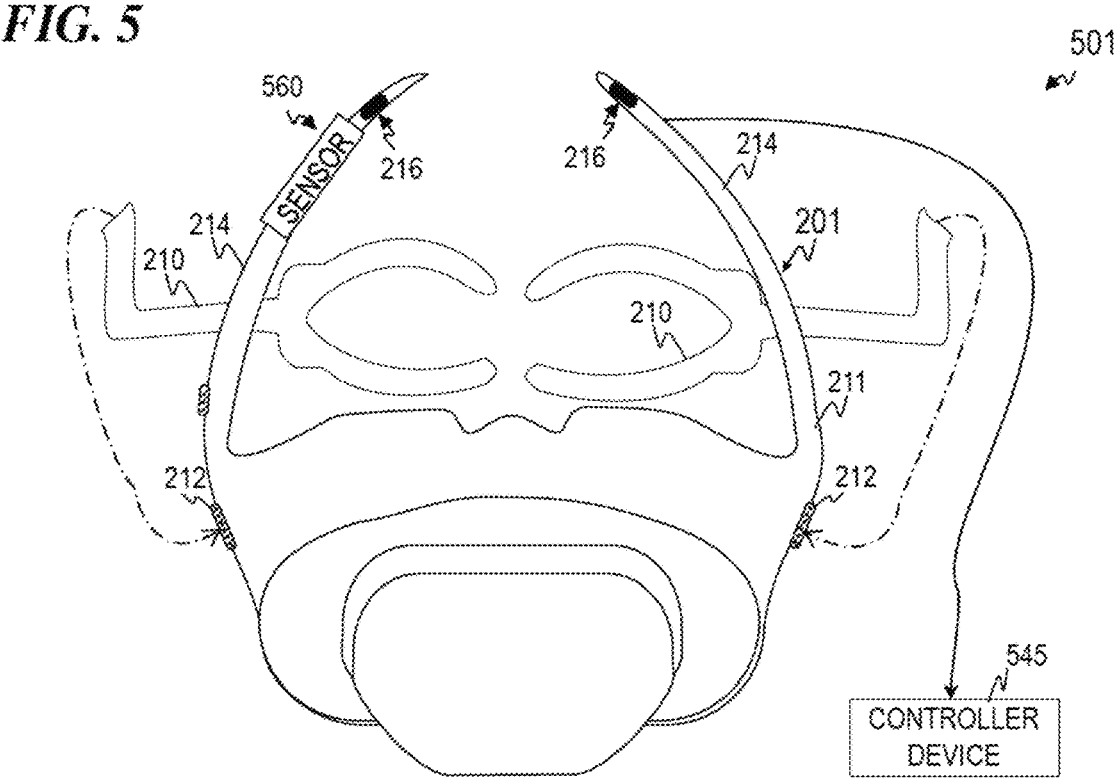
FIG. 5 is a diagram of system 501, according to some embodiments of the present invention.

FIG. 5 is a diagram of a goggle-type device 501, according to some embodiments of the present invention. In some embodiments, device 501 includes a connecting wire 541 that runs from the headset frame (e.g., headset frame 211) to a bio-electric microcurrent controller device 545 (such as a near-by laptop computer, smart cell phone, iPad®, or the like. In some embodiments, device 501 includes a bio-electric microcurrent controller device 550 that is built into the headset frame (e.g., headset frame 211). In some embodiments, device 501 includes a sensor 560 on the headset frame (e.g., headset frame 211 or temple side pieces 214) that provides feedback (such as the sensed impedance of the electrical connections between the plurality of electrodes 116 and the patient's skin, or a galvanic skin response of the patient's skin, nerve activity of areas of the patient's skin near the points of electrical stimulation during electrical stimulation of those nearby points of electrical stimulation, nerve activity of the areas at the points of electrical stimulation during "rest" time periods between the times of electrical stimulation, or the like), to the controller device (e.g., controller device 545 and/or controller device 550) for use in determining any needed adjustment in stimulation level being delivered, etc.

Figure 6:
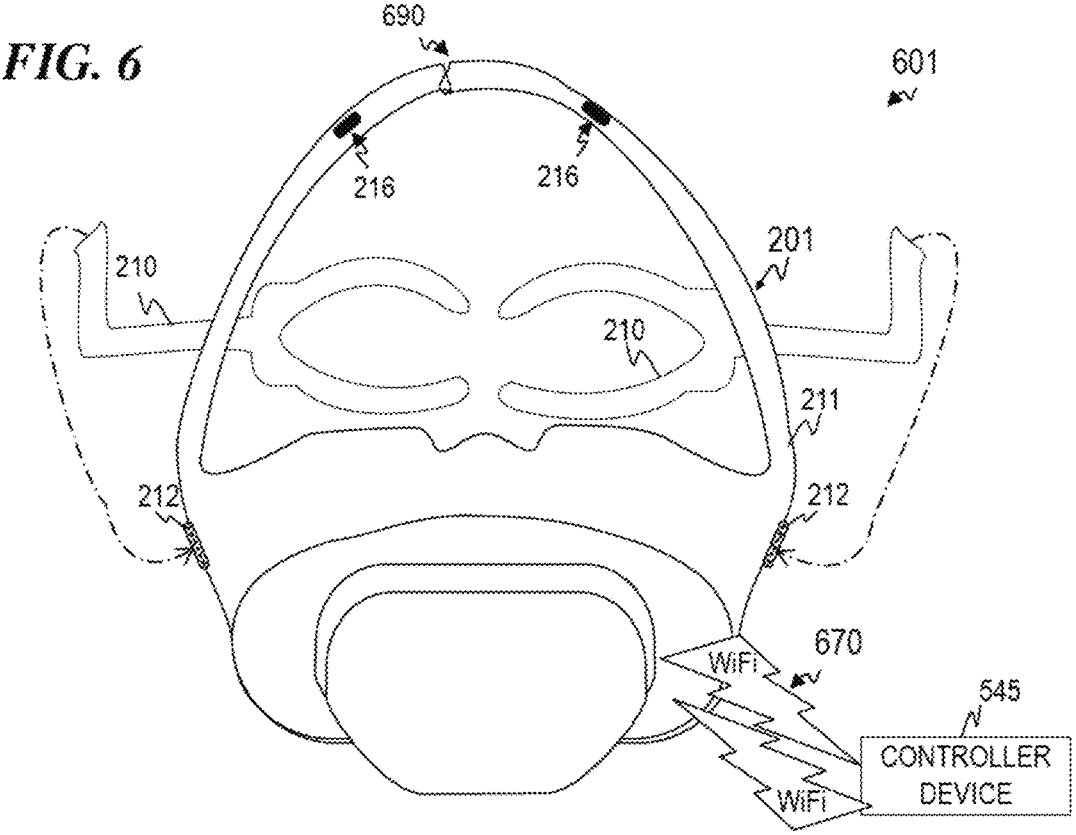
FIG. 6 is a diagram of goggle-type device 601 having a wireless RF connection 670 that allows device 601 to connect (e.g., via Wi-Fi) to a separate device such as a controller in a local laptop, computer server, iPad®, or the like, according to some embodiments of the present invention.

FIG. 6 is a diagram of a goggle-type device 601, according to some embodiments of the present invention. In some embodiments, device 601 includes a Wi-Fi connection 670 (or other wireless communication means such as infrared signals, RF signals such as Bluetooth® or the like) that allows device 601 to connect, via Wi-Fi (or other wireless bidirectional or unidirectional communication), to a separate device such as controller device 545, a server, a computer, or the like, in order to provide separated local or remote access and/or control to and/or for device 601. In some embodiments, device 601 (or other devices such as shown and described below for FIG. 7A, FIG. 7B, FIG. 8, FIG. 9A, and elsewhere herein) uses a headband 690 (rather than temple side pieces 214) to hold the goggle device 601 to the patient's head. In some such embodiments, headband 690 further includes other features such as grounding electrical conductors 216 and/or tensioning devices such as described below.

Figure 7A:
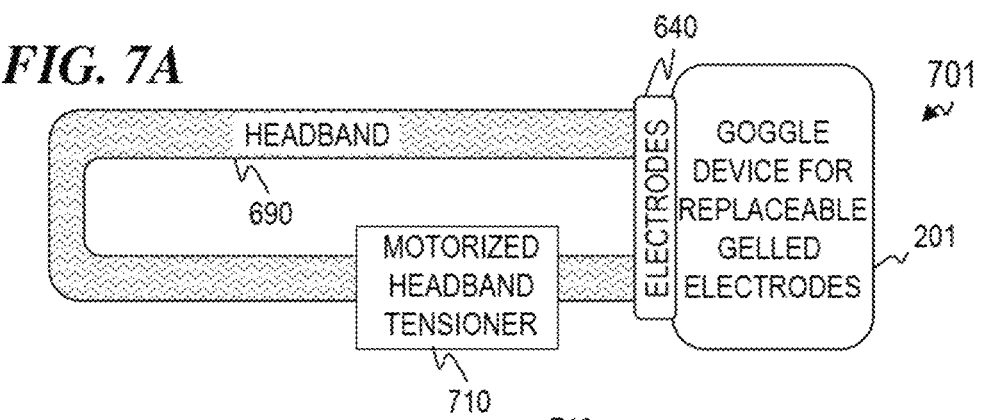
FIG. 7A is a diagram of system 701 having a headband tensioner 710 to adjust a pressure of the electrodes against the patient's skin, according to some embodiments of the present invention.

FIG. 7A is a diagram of system 701 having a headband tensioner 710 to adjust a pressure of the electrodes 1169 against the patient's skin, according to some embodiments of the present invention. In some embodiments, during an initial setup procedure, electrical pulses are applied to two or more selected ones of the plurality 116 of electrodes 1169 and headband tensioner 710 tightens and loosens the tension on headband 690 in order to achieve a desired impedance or other electrical parameter, and/or to improve patient comfort while maintaining good electrical connections to the patient's skin.

Figure 7B:
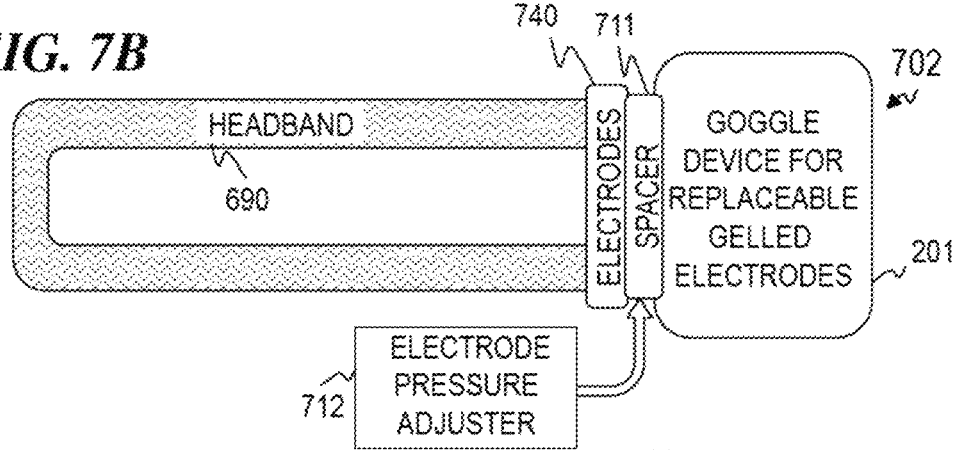
FIG. 7B is a diagram of system 702 having an adjustable-pressure spacer 712 to adjust a spacer 711 that applies pressure to the electrodes against the patient's skin, according to some embodiments of the present invention.

FIG. 7B is a diagram of system 702 having an adjustable-pressure spacer 712 to adjust a spacer 711 that applies pressure to the electrodes against the patient's skin, according to some embodiments of the present invention.

Figure 8:
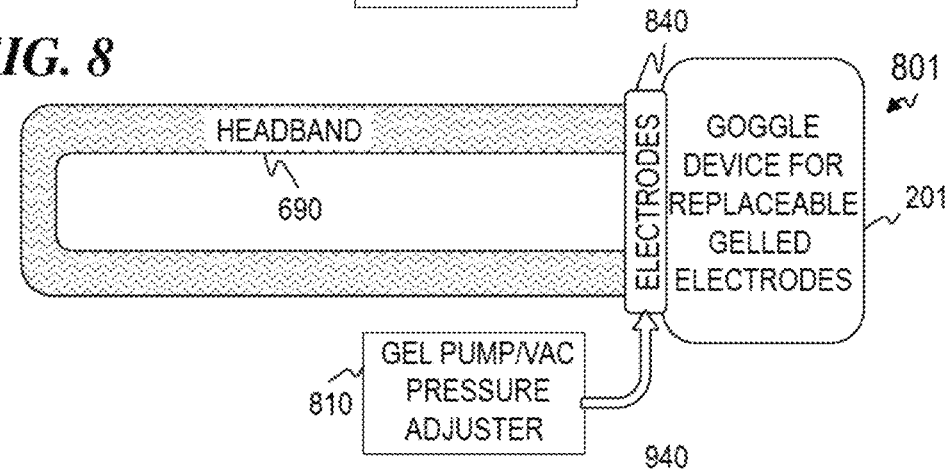
FIG. 8 is a block diagram of system 801 having an adjustable-gel-pressure/vacuum device 810 to adjust a pressure and/or suction of the gel of the electrodes against the patient's skin, according to some embodiments of the present invention.

FIG. 8 is a block diagram of system 801 having an adjustable-gel-pressure/vacuum device 810 to adjust a pressure and/or suction of the gel of the electrodes against the patient's skin, according to some embodiments of the present invention.

Figure 9A:
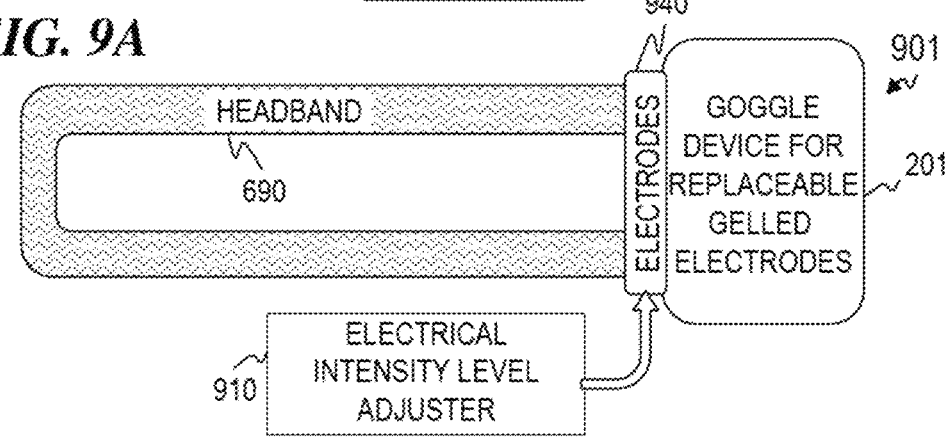
FIG. 9A is a block diagram of system 901 having an adjustable-electrical-intensity device 910 to adjust the electrical signal applied to the electrodes against the patient's skin, according to some embodiments of the present invention.

FIG. 9A is a block diagram of system 901 having an adjustable-electrical-intensity device 910 to adjust the electrical signal applied to the electrodes against the patient's skin, according to some embodiments of the present invention.

Figure 9B:
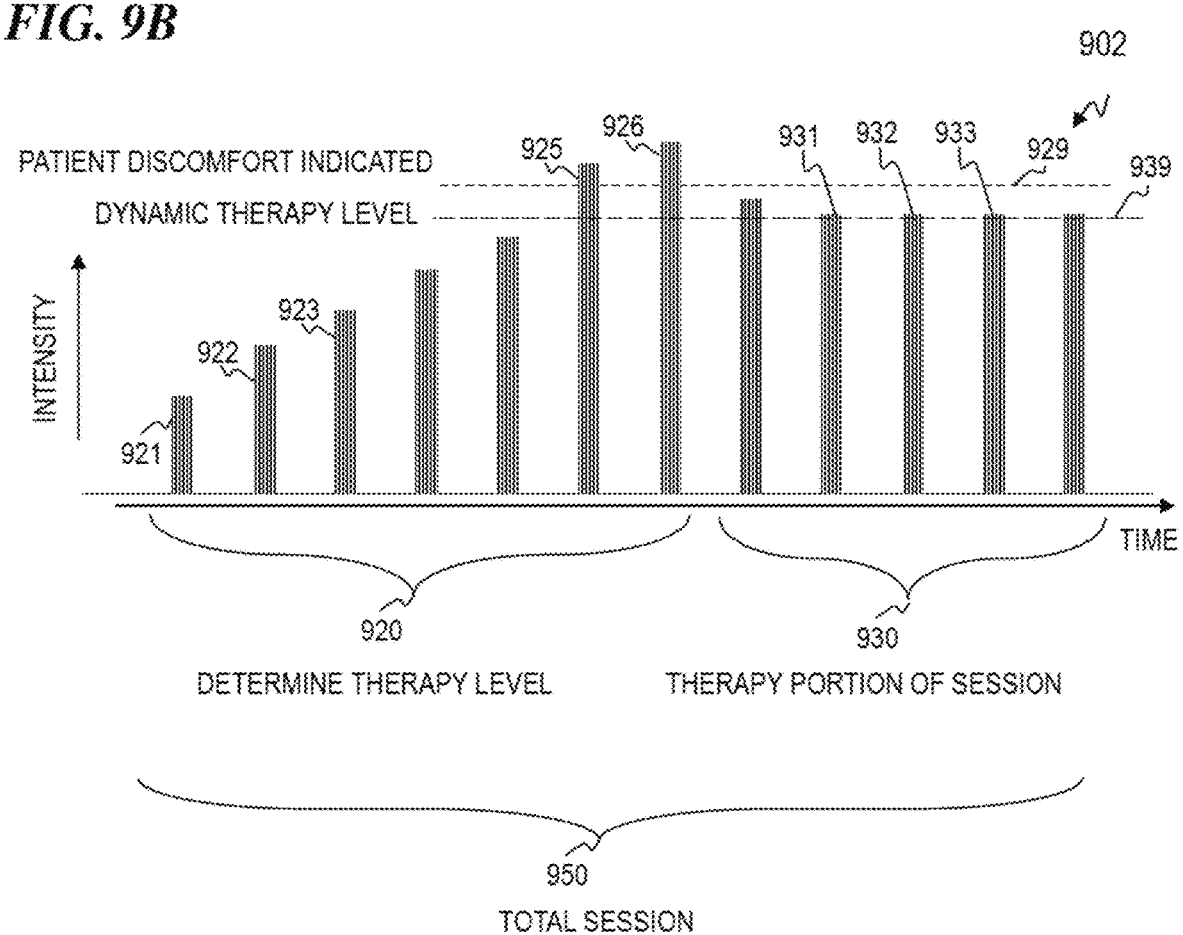
FIG. 9B is a schematic waveform diagram 902 obtained when adjusting the electrical signal applied to the electrodes against the patient's skin, according to some embodiments of the present invention.

FIG. 9B is a schematic waveform diagram 902 obtained when adjusting the electrical signal applied to the electrodes against the patient's skin, according to some embodiments of the present invention. In some embodiments, an intensity-determination series of pulses 920 are generated that have gradually increasing electrical current amplitude (see pulses 921, 922, and 923, etc.), such that adjustable-electrical-intensity device controller 910 (see FIG. 9A) receives feedback as to the skin impedance and/or patient-generated feedback (such as a voice command (or shriek) or a push-button switch signal) that indicates patient discomfort (see, e.g., pulses 925 and 926 that are above the discomfort level 929), and upon receiving such feedback signal from the patient or the patient's physiological response to the pulses), the adjustable-electrical-intensity device controller 910 reduces the current and/or voltage of the pulses to a therapeutic level 939 that is better tolerated than the level causing discomfort. Then, a therapy series of pulses 930 is applied, e.g., therapy pulses 931, 932, 933, etc. The total treatment session 950 includes the intensity-determination series of pulses 920 and the therapy series of pulses 930.

Figure 10:
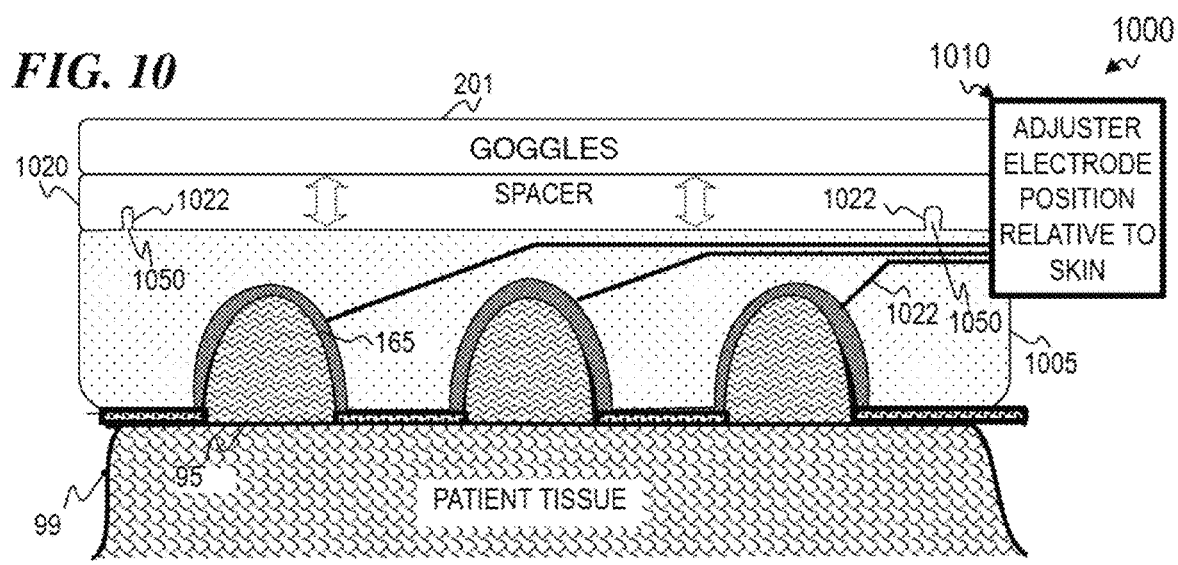
FIG. 10 is a block diagram of system 1000 having an adjustable-spacer-pressure controller 1010 and spacer 1020 to adjust a pressure of the electrodes against the patient's skin, according to some embodiments of the present invention.
Figure 11:
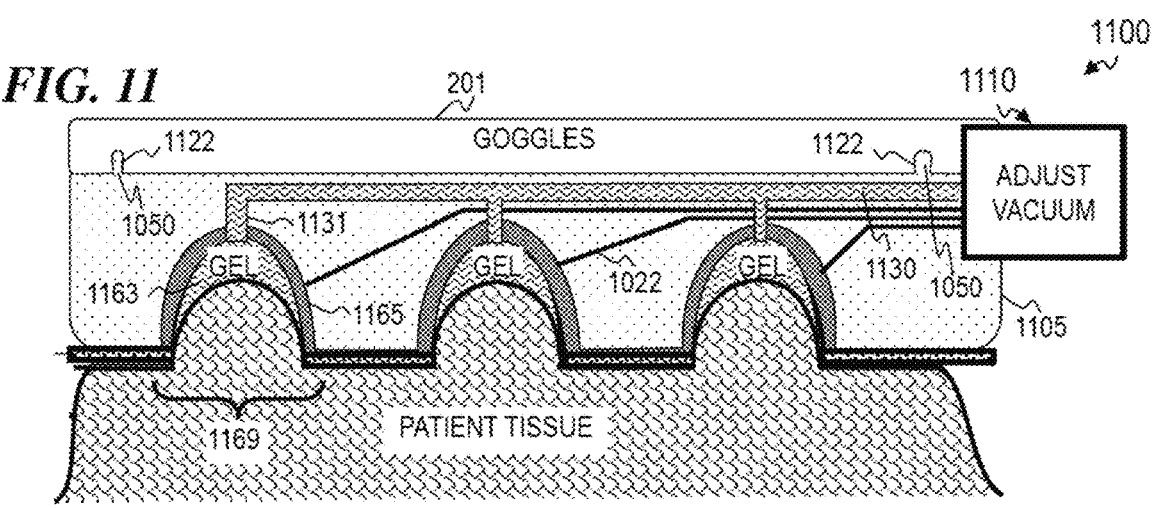
FIG. 11 is a block diagram of system 1100 having an adjustable-gel-pressure/vacuum device 1110 to adjust a pressure and/or suction of the gel of the electrodes against the patient's skin, according to some embodiments of the present invention.

FIG. 10 is a block diagram of system 1000 having an adjustable-spacer-pressure controller 1010 and spacer 1020 to adjust a pressure on stimulation strip 1005 having a plurality 116 of electrodes 1169 (see FIG. 1E) against the patient's skin 95 (e.g., in some embodiments, the eyelids of patient 99), according to some embodiments of the present invention. In some embodiments, system 1000 includes a pressure actuator 1020 (a variable-thickness spacer such as a pneumatic chamber, a linear motor, a pair of wedges, or the like) that is controlled by pressure controller 1010 to adjust the pressure against the patient's skin. In other embodiments (such as shown in FIG. 7A), system 1000 varies a tension applied to a headband 690 to adjust the pressure on the stimulation-strip electrodes. In some embodiments, pressure controller 1010 receives feedback as to the skin impedance and/or patient-generated feedback (such as a voice command (or shriek) or a push-button switch signal) that indicates patient discomfort (e.g., the pressure is too high), and upon receiving such feedback signal from the patient or the patient's physiological response to the pressure), the pressure controller 1010 reduces the pressure to a therapeutic level that is better tolerated than the level causing discomfort. In some embodiments, stimulation strip 1005 includes a plurality of snap-like protrusions and/or receivers 1050 (male/female structures) that snap together to hold stimulation strip 1005 to corresponding snap-like receivers and/or protrusions 1022 (female/male structures) on spacer 1020 (or goggles 201 as shown in FIG. 11). In some embodiments, each electrode 1169 is electrically coupled via conductors 1022 to an electrical driver circuit (such as 111 of FIG. 1A or 155 of FIG. 1B).

FIG. 11 is a block diagram of system 1100 having an adjustable-gel-pressure/vacuum device 1110 to adjust a pressure and/or suction of the gel 1163 of the electrodes 1169 against the patient's skin, according to some embodiments of the present invention. In some embodiments, system 1100 includes a stimulation strip 1105 that includes a plurality of gel-filled channels 1130 that connect to pocket 1165 of each electrode 1169 via a channel 1131. In some embodiments, system 1100 varies a vacuum (or pressure) applied to the gel 1163 in the pockets 1165 by pulling or pushing on the gel (e.g., some embodiment use a syringe operated by a linear motor or the like, the syringe pneumatically connected to passageway 1130). In some embodiments, vacuum controller 1110 receives feedback as to the skin impedance and/or patient-generated feedback (such as a voice command (or shriek) or a push-button switch signal) that indicates patient discomfort (e.g., the vacuum is too high) or a less than optimal physiological electrode connectivity to the patient, and upon receiving such feedback signal from the patient or the patient's physiological response to the pressure/vacuum), the vacuum controller 1110 relaxes the vacuum/pressure applied to a therapeutic level that is better tolerated than the level causing discomfort (or a level that obtains a better physiological signal). In some embodiments, stimulation strip 1105 includes a plurality of snap-like protrusions and/or receivers 1050 (male/female structures) that snap together to hold stimulation strip 1105 to corresponding snap-like receivers and/or protrusions 1122 (female/male structures) on goggles 201. In some embodiments, each electrode 1169 is electrically coupled via conductors 1022 to an electrical driver circuit (such as 111 of FIG. 1A or 155 of FIG. 1B). In some embodiments, system 1100 can apply a varying vacuum and/or pressure (such as shown in FIG. 12) using the same controller 1110.

Figure 12:
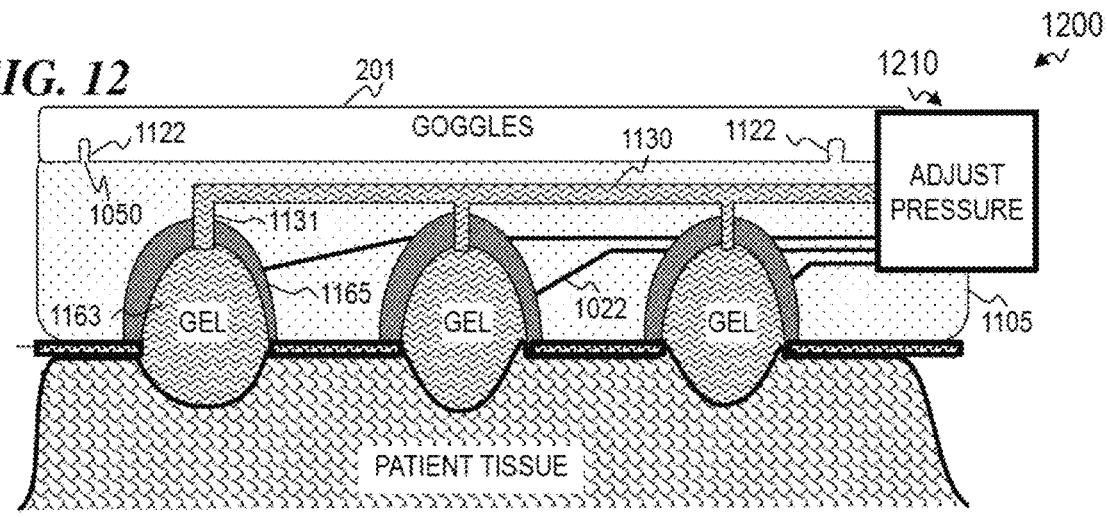
FIG. 12 is a block diagram of system 1200 having an adjustable-gel-pressure device 1210 to adjust a pressure of the gel of the electrodes against the patient's skin, according to some embodiments of the present invention.

FIG. 12 is a block diagram of system 1200 having an adjustable-gel-pressure device 1210 to adjust a pressure of the gel of the electrodes against the patient's skin, according to some embodiments of the present invention. System 1200 is substantially similar to system 1100 except that controller 1210 only varies the pressure applied to gel 1163.

The headset apparatus may contain an LED, LCD, or some other type of screen, like a small i-Phone touch screen to show the treatment sequencing, the status of such treatment, and/or to engage or halt such treatment. This screen may show graphics, pictures, or even video footage related to such treatment process, with the purpose of making it easier for a clinician to readily assess where the patient is within the treatment cycle, or to enable the clinician to start, change, or stop such treatment cycle. The screen can be a touch screen that enables the clinician to modify the treatment parameters, such as stimulation level or duration under treatment.

The headset connects via Wi-Fi to server or computer, which recognizes the individual headset via a unique set of algorithmic codes built into the headset's control unit. Once the server or computer is connected to the headset and it recognizes the headset's unique algorithmic code, it can then enable the headset, when initiated by a clinician or physician, to conduct a treatment session. It can also simultaneously bill or charge the provider for payment of such treatment session. The headset can also send the treatment parameters used to the server or computer for record of how the device was used. The headset is rechargeable for repeated use, and it connects to a base station. The base station can plug into the wall to maintain the charge to recharge the headset. The headset does not plug into the wall directly for safety purposes.

The apparatus may contain a "light" filament or filaments threaded through the headset to convey a low level of light through the patient's closed eyes, indicating to the patient, that the appliance/strip is functioning as intended. This low level of light will penetrate the patient's closed eyelid and be received by those photoreceptor cells functioning in the back of the retina. It will resemble a dull flash, and may be either a white light or a specially colored light (such as red or green, like a laser light).

The apparatus may also contain a vibrating filament threaded through the headset, to convey a light level of vibration as the stimulation is being applied. Again, this is for the function of conveying to the patient that the stimulation is being delivered for those instances where the bio-electric microcurrent, itself, may be simply unfelt by the patient. The benefit of this is that the patient can feel it working, and will then be more willing to sit and complete the full treatment session, versus a session where they have no marker to indicate that anything is happening.

The application of the apparatus will be performed by the attending physician or clinician in the clinic. The patient's eye lids will be cleaned with sterile solution contained in a wipe or similar material. The clinician, using sterile surgical gloves, will then open the packet containing the headset; the headset will then be mounted on the patient's head by the clinician. The clinician will then connect the headset (or goggle)—both forms to be used interchangeably in the following descriptions—to the bio-electric microcurrent strips, and the entire headset will be configured to the patient in the following manner:

- The headset will be sized to properly fit the patient in terms of the size of their head.
- The headset will be connected to the individual bio-electric microcurrent strip(s), (electrode)(s) whose contact points will be placed on the patient's closed eyelids, just below the eyebrows, across the bone of the upper eye orbit cavity, and also applied under the eye, along the bone of the lower orbit.
- The treatment electrode(s) contain an embedded chip to regulate the performance during treatment, including one-time usage, identification purposes, and purchase confirmation by clinic or user.
- The headset is also connected to one or two grounding electrodes placed at another point on the body to complete the closed circuit of the individual bio-electric microcurrent strips.
- The headset would be connected to the bio-electric microcurrent device (i.e., controller), built into the headset, or connected via wire when it is a separate device, or connected via Wi-Fi when it is a separate device, to initiate therapy.

In some embodiments, when the therapy is finished, a beeper will sound. The clinician will then disconnect the headset from the electrodes, and in the case of a separate control device, from the separate control device if it is attached via wires generating the bio-electric microcurrent. Next, the clinician will gently remove the headset from the patient. The headset will be cleaned in accordance with company instructions as guided by any government directives, or in the case of a disposable headset, disposed of in accordance with any government directives. The patient's eye(s) will be re-cleansed with a sterile wipe/pad.

ADVANTAGES OF THE NEW TECHNOLOGY (Microstimulation Headset Frame)

a. It is an advantage of the present invention to provide a novel electrode apparatus for providing bio-electric microcurrent stimulation therapy to a body part to combat chronic pain, injury, or disease in that body part, or to assess or monitor internal organ function within the body.

b. Another advantage of the present invention is to provide a novel electrode apparatus for treating various diseases, including macular degeneration and retinitis pigmentosa.

c. Yet another advantage of the present invention is to provide an electrode apparatus that delivers bio-electric microcurrent stimulation therapy via a headset frame attached to electrodes that are wired to (or connected via Wi-Fi to) the control apparatus and are positioned on the upper or lower eye lid with an adhesive material.

d. Yet another advantage of the headset is that the clinician can begin treatment and leave the patient during the treatment cycle for multi-tasking efficiency and reducing clinician labor.

e. Yet another advantage is that the clinician can be away from the patient, but periodically check on the patient's progress with the headset's screen.

f. Yet another advantage of the headset/goggle device, with the connected electrodes, is the automation of the treatment process and its ability to deliver a consistent treatment, thereby minimizing variability of such treatment that otherwise would be present if it were delivered manually by a clinician in terms of: time, pressure of the electrode at the point of stimulation, consistency of application, contact of the electrode, and consistency of the stimulation level being delivered as initially selected for treatment setup.

g. Yet another advantage is that both eyes are set up simultaneously for treatment, saving time since there is just one set up. (The patient may have one eye treated at a time and then the other, during the treatment cycle, OR the headset could be configured to simultaneously treat both eyes at once, one electrode point at a time per each eye until the cycle is completed.)

h. Yet another advantage of the headset's inner circular frame is that it will comfortably and easily fit most patients' heads and make for easy connection of the electrodes around the eye.

i. This headset contains or will be connected to various numbers of electrodes or sensors, which are wired and sensed individually by a controller device, which gives the ability of the apparatus to monitor the current supplied to the various contact points in the electrodes, and to adjust the current based upon the degree of impedance.

j. The invention will be packaged as sanitary, depending upon the requirements in a barrier-proof package.

k. Yet another advantage is this headset apparatus will be connected to a software program that can administer the treatment therapy, and can also collect patient information regarding the application of the treatment applied to the patient, for improved patient outcomes.

l. Yet another advantage is that the invention contains one or a number of light filaments in the headset frame, that can signal the patient that the proper level of therapy is being delivered to the patient and that they are not experiencing undue impedance.

m. Yet another advantage is in the field of safety, as the device cannot be randomly used since it needs to be pre-authorized by the server or computer, via the unique algorithm, to conduct the treatment session.

n. Yet another advantage is that the payment for each treatment is monitored on an individual basis by the server or computer, with each session used being specifically enabled by the server/computer, tracked, and accounted for, so it can be paid for by the clinic.

o. Yet another advantage is that the clinician can see the status of the therapy in session and or modify it at any time, with the use of the headset's touch screen.

p. Yet another advantage is the headset plugs into a base station device that recharges the headset, so that the headset can be recharged and used repeatedly, and so that the headset does not directly plug into the wall, which is a usage safety guard for the patient per regulatory codes.

q. Yet another advantage is that the treatment electrodes contain a chip, similar to a security chip in a credit card but optionally with additional functionality such as a controller and current drivers and receiving preamplifiers and the like, which enables a one-time use and can be tracked via the headset controller. This prevents the reuse of electrodes for a safety and hygiene basis, as well as insures proper accounting for the electrodes from a purchase and billing standpoint. This chip technology will enable confirmation of: electrode identity and authenticity, purchase, and one-time usage.

r. Accordingly, it is an advantage of the present invention to incorporate a safety element by individually wiring each electrode sensor point connected to the treatment device, which provides the bio-electric stimulation. Such design prevents more than one electrode point delivering the therapy simultaneously, unless so specifically programmed, and potentially injuring the patient.

s. The advantage of this apparatus is that the bio-electric stimulation is not carried simultaneously over the entire surface of the treated area, and that an individually targeted area of the eye can be treated with stimulation therapy, while not stimulating other areas of the eye or surrounding tissues. Stimulation is delivered at differing specific individual points in a programmed manner, versus the current standard of a general stimulation delivery over the affected area in the many other medical fields where electrode stimulation is used.

t. The advantage of highly targeted bio-electric stimulation is that this ensures that a more concentrated delivery is made to the targeted area, with a greater chance of deeper inner penetration of the stimulation, to the back of the retinal tissues, where it can do the most good to reactivate cellular activity, and avoiding higher levels of stimulation, which might otherwise be required without such targeting, which can incidentally cause damage to the more sensitive tissues.

u. Another advantage is that specific areas of bio-electric stimulation can be chosen by the physician, as determined by the program used in the bio-electric microcurrent device connected to the headset/apparatus. It has specifically sequenced points within the electrodes that can deliver timed specific stimulation to different points along the frame itself, in a pre-set sequence, for a varied or pre-set time, at an individual point of contact, or at two or more points of individual contact, with preset stimulation levels, as opposed to a single Gel Pad which offers blanket stimulation over the entire surface area of the pad.

v. Another advantage of this appliance and its treatment methodology is that it enables the physician to target bio-electric stimulation to a particular treatment point (as small as 2 millimeters, or as large as 15 millimeters), which improves treatment efficacy since a higher current dose cannot be tolerated by the body at a small pinpoint of delivery, or be effective if delivered over a larger surface area, such as by a standard gel pad. Further, this bio-electric stimulation can be delivered to a specifically designed and tolerated treatment point within a timed sequence and then on to another in a pre-set pattern designed to optimize treatment results for patients.

Elements of Apparatus Design According to Some Embodiments:

a) Method for Application to upper, and/or lower eye, as well as other body parts.

b) Bio-electric Microcurrent Headset Frame.

c) Headset Frame connects to electrodes, which stimulate the upper and lower eyelid, or other body part(s) as applied, using an electrode with a gel coating.
   a. Such electrodes contain a chip and this technology serves to identify the electrode using this chip to the controller as authentic, to allow a one-time use for safety and hygiene purposes, and to ensure payment regulation.

d) Headset frame connects to electrodes which:
   1. Have between 1-10 (or more) contact points on the top of the strip for the top closed eye lid or skin covering the upper orbit.
   2. Have between 1-10 (or more) contact points on the bottom of the strip for the bottom closed eye lid or skin covering the lower orbit.
   3. Do not stimulate entire eye, only under those specific points selected within the stimulation program determined by physician and programmed into device.
   4. Contact points can be individual or multiple, meaning that ONE contact point can stimulate at a time per eye, or body part; OR two to several contact points may stimulate simultaneously, determined by the program selected on the device. (In addition, the entirety of the strip(s), and all of the contact points may also be active with stimulation at any one given point during the treatment in addition to the individual points stimulated.)
   5. Contact points may stimulate individually or in multiple points, in a pre-programmed sequence, with a pattern that is pre-set in terms of specific stimulation level(s), individual stimulation point duration time(s), total program run time, number of times of stimulation per eye point, etc., all of which is determined by the program in the device, selected by the attending clinician delivering the stimulation.
   6. Contact points are capable of receiving varied stimulation levels as determined by device. (Meaning that the stimulation level delivered through the various contact points can vary and be increased or decreased throughout the course of the treatment program selected.)

e) This invention makes it is less labor intensive to conduct the treatment (since the clinician can turn the headset on, start the programmed treatment, and go off to do another task while the program runs its course); less time consuming (since the clinician is freed up during the programs duration to attend to other tasks), and less fatiguing (since the clinician does not need to stand over the patient and hold the stimulation probe.)

f) Safety Element: The headset and its controller (whether built in or attached via wires) rely on a safety governor built in to the controller device, so one point cannot deliver more than, for example, 1000 microamps of current. Sensors: Headset, controller, and strips have a built-in sensor to monitor stimulation level delivered to improve treatment performance:
  1. Sensor also gauges impedance of skin:
  2. Sensor to give feedback to device to actual stimulation delivered to skin. (Feedback loop)
  3. Sensor to automatically adjust bio-electric current level deliver to patient, to achieve the selected/programmed stimulation level, regardless of impedance (in some embodiments, up to 1000 microamps).

g) Headset may contain an internal light filament built in to frame to indicate stimulation delivery to patient. Filament would flash lightly in conjunction with the delivery of the stimulation. This feature can be manually turned off for no flash.

h) Headset may contain an external visible light for the clinician to monitor treatment. Light will go from constant (when selected stimulation is appropriately delivered); to flash if stimulation being delivered has impedance and is under-delivered; or, to rapid flash if impedance is high and stimulation being delivered is significantly under-delivered.

i) Headset may contain a vibration element built into frame, designed to indicate stimulation delivery.

j) Headset either has a built-in controller or contains a connection element to primary controller device, via either wires or via Wi-Fi.
  1. The controller has a unique algorithm ensuring its identification and connection to the server or computer.
  2. Each controller can be identified as to location and modified by the company as to its operational capabilities, permitting the company to upgrade the controller software and operating system at any time.
  3. The controller requires the connection to the server or computer for activation of the therapy to ensure control over the therapy sessions being delivered and to ensure proper payment for such sessions.

k) Headset has a built-in touch screen (in some embodiments, smaller, but similar to an Apple iPhone®). This touch screen enables the clinician to start the program; to stop the program; and to adjust any of the treatment variables. It also features a display with a read-out of the treatment status in progress.

l) Headset may have two moveable or "flip-oriented" lens covers, (one around each eye), that are lens-less, but designed to come in moderately tight contact, (e.g., in some embodiments, a range of two ounces per square inch (about 862 Pascals) to fifteen (15) pounds per square inch (about 0.103 megapascals)), with the closed upper and lower eye lid, to ensure proper contact with the electrode. This could be done via a spring mounted to the lens cover arm, as it is flipped down to cover the electrode strip(s), or any other suitable apparatus for applying pressure to the lens cover arm.

m) The headset design can be adjusted to accommodate different sized anatomical head configurations.

n) Headset may contain a sensor for feedback to device to register stimulation level being delivered.

o) Headset may contain a timing sensor (buzzer/chime) to notify when session is completed.

p) Headset may contain an LED or LCD type of screen, in some embodiments, similar to a small iPod screen, showing the status of the treatment session, including which eye is being stimulated, which eye point is being stimulated, where in the cycle of stimulation the treatment session is, and when the session has ended. This visual screen will also show product name, program time elapsed, and stimulation level being delivered to patient.

In some embodiments, the present invention provides an apparatus for applying bio-electric microcurrent stimulation therapy to the human body, via a disposable chip-electrode array that connects to a micro-stimulation current generating device, for application of the microcurrent stimulation therapy. In some embodiments, the apparatus includes a headset device for mounting to the patient's head; and one or more electrode strips such as a one-use disposable chip-electrode array having a unique serial number or crypto code and other functionality that is used by the system to look up and deliver customized therapy to a particular patient having their own particular symptoms and medical history, which deliver the stimulation to the patient's skin.

In some embodiments, the present invention provides a method for applying bio-electric microcurrent stimulation therapy to the human body of a particular patient, via a disposable chip-electrode array strips such as a one-use disposable chip-electrode array having a unique serial number or crypto code that connects to a micro-stimulation current generating headset, for application of the microcurrent stimulation therapy. This method includes mounting the headset to the patient's head; applying one or more electrode strips to the patient's skin; connecting the one or more electrode strips to the headset; communicating the unique serial number or crypto code to a computer server; using the unique serial number or crypto code in the computer server to look up and return a customized therapy regimen specification to the headset for the a particular patient having their own particular symptoms and medical history; and using the customized therapy regimen specification, deliver the microcurrent stimulation to the patient's skin.

In some embodiments, the present invention provides a non-transitory computer-readable medium having instructions stored thereon for causing a suitably programmed information processor to execute a method for applying bio-electric microcurrent stimulation therapy to the human body of a particular patient, via a disposable chip-electrode array strips such as a one-use disposable chip-electrode array having a unique serial number or crypto code that connects to a micro-stimulation current generating headset, for application of the microcurrent stimulation therapy. This method includes mounting the headset to the patient's head; applying one or more electrode strips to the patient's skin; connecting the one or more electrode strips to the headset. The instructions cause the suitably programmed information processor to execute a method that includes: communicating the unique serial number or crypto code to a computer server; using the unique serial number or crypto code in the computer server to look up and return a customized therapy regimen specification to the headset for the a particular patient having their own particular symptoms and medical history; and using the customized therapy regimen specification, deliver the microcurrent stimulation to the patient's skin.

In some embodiments, the present invention provides a system for applying bio-electric microcurrent stimulation therapy to a patient, the system including a head-mounted device configured to be mounted to the patient's head; a chip-electrode-array circuit operatively coupled to the head-mounted device, wherein the chip-electrode-array circuit includes at least one integrated-circuit chip and at least one electrode-array strip configured to deliver the bio-electric microcurrent stimulation therapy to the patient, wherein the chip-electrode-array circuit includes a unique identification number; and a computer server operatively coupled to the chip-electrode-array circuit, wherein the chip-electrode-array circuit is configured to communicate with the computer server in order to have the computer server look up and receiver parameters based at least in part on the unique identification number and communicated the looked-up parameters to the chip-electrode-array circuit for the bio-electric microcurrent stimulation therapy.

In some embodiments of the system, the parameters are further based on particular symptoms and medical history associated with the patient. In some embodiments, the unique identification number is a serial number stored in the at least one integrated-circuit chip and communicated from the at least one integrated-circuit chip to the computer server. In some embodiments, the unique identification number is a serial number printed on the at least one electrode-array strip and read by a camera to obtain image data that is communicated to the computer server. In some embodiments, the chip-electrode-array circuit is a one-use disposable chip-electrode-array circuit. In some embodiments, the unique identification number includes public-key encryption information that is used by the computer server to encrypt data sent to the chip-electrode-array circuit. In some embodiments, the computer server includes a medical-results-and-indication database, wherein results of the bio-electric microcurrent stimulation therapy are transmitted to the medical-results-and-indication database to be analyzed in order to improve future therapy sessions.

In some embodiments of the system, the chip-electrode-array circuit includes a microprocessor integrated with the chip-electrode-array circuit. In some embodiments, the system further includes a local microprocessor system operatively coupled to the chip-electrode-array circuit. In some embodiments, the system further includes a local microprocessor system operatively coupled to the chip-electrode-array circuit, wherein the local microprocessor system includes a first portion located on the head-mounted device and a second portion located remotely from the head-mounted device.

In some embodiments, the present invention provides a method for applying bio-electric microcurrent stimulation therapy to a patient via a chip-electrode-array circuit that includes at least one integrated-circuit chip, at least one electrode-array strip, and a unique identification number, the method including providing a head-mounted device; connecting the at least one electrode-array strip to the head-mounted device; mounting the head-mounted device to the patient's head such that the head-mounted device applies the at least one electrode-array strip to the patient's skin; transmitting information from the chip-electrode-array circuit to a computer server, wherein the transmitted information includes the unique identification number; receiving into the chip-electrode-array circuit, from the computer server, parameters for the bio-electric microcurrent stimulation therapy, wherein the received parameters are based at least in part on the unique identification number; and delivering, via the at least one electrode-array strip, the bio-electric microcurrent stimulation therapy to the patient based on the received parameters.

In some embodiments of the method, the received parameters are further based on particular symptoms and medical history associated with the patient. In some embodiments, the unique identification number is a serial number stored in the at least one integrated-circuit chip, and wherein the transmitting of the information includes communicating the serial number from the at least one integrated-circuit chip to the computer server. In some embodiments, the unique identification number is a serial number printed on the at least one electrode-array strip, and wherein the transmitting of the information includes reading, using a camera, the printed serial number to obtain image data and communicating the obtained image data to the computer server. In some embodiments, the chip-electrode-array circuit is a one-use disposable chip-electrode-array circuit. In some embodiments, the unique identification number includes public-key encryption information, the method further comprising encrypting data sent to the chip-electrode-array circuit from the computer server using the public-key encryption information.

In some embodiments, the method further includes transmitting results of the bio-electric microcurrent stimulation therapy to a database located on the computer server; and analyzing the results in order to improve future therapy sessions. In some embodiments, the method further includes integrating a microprocessor with the chip-electrode-array circuit. In some embodiments, the method further includes providing a local microprocessor system; and coupling the local microprocessor system to the chip-electrode-array circuit. In some embodiments, the method further includes providing a local microprocessor system, wherein the local microprocessor system includes a first portion and a second portion; and coupling the first portion of the local microprocessor system to the head-mounted device, wherein the second portion of the local microprocessor system is located remotely from the head-mounted device.

In some embodiments, the present invention provides a non-transitory computer-readable medium having instructions stored thereon for causing a suitably programmed information processor to execute a method for applying bio-electric microcurrent stimulation therapy to a patient via a chip-electrode-array circuit that includes at least one integrated-circuit chip, at least one electrode-array strip, and a unique identification number, wherein the chip-electrode-array circuit is coupled to a head-mounted device, the method including transmitting information from the chip-electrode-array circuit to a computer server, wherein the transmitted information includes the unique identification number; receiving into the chip-electrode-array circuit, from the computer server, parameters for the bio-electric microcurrent stimulation therapy, wherein the received parameters are based at least in part on the unique identification number; and delivering, via the at least one electrode-array strip, the bio-electric microcurrent stimulation therapy to the patient based on the received parameters.

In some embodiments, the non-transitory computer-readable medium further includes instructions such that the received parameters are further based on particular symptoms and medical history associated with the patient. In some embodiments, the non-transitory computer-readable medium further includes instructions such that the unique identification number is a serial number stored in the at least one integrated-circuit chip, and wherein the transmitting of the information includes communicating the serial number from the at least one integrated-circuit chip to the computer server. In some embodiments, the non-transitory computer-readable medium further includes instructions such that the unique identification number is a serial number printed on the at least one electrode-array strip, and wherein the transmitting of the information includes reading, using a camera, the printed serial number to obtain image data and communicating the obtained image data to the computer server. In some embodiments, the non-transitory computer-readable medium further includes instructions such that the unique identification number includes public-key encryption information, the non-transitory computer-readable medium further including instructions such that the method further includes encrypting data sent to the chip-electrode-array circuit from the computer server using the public-key encryption information.

In some embodiments, the non-transitory computer-readable medium further includes instructions such that the method further includes transmitting results of the bio-electric microcurrent stimulation therapy to a database located on the computer server; and analyzing the results in order to improve future therapy sessions.

In some embodiments, the present invention provides an apparatus for applying bio-electric microcurrent stimulation therapy to a patient, the apparatus including a head-mounted device configured to mount to a head of the patient; a plurality of electrodes coupled to the head-mounted device such that the plurality of electrodes contact the patient at a plurality of contact points when the head-mounted device is worn by the patient, wherein the plurality of electrodes is configured to deliver the bio-electric microcurrent stimulation therapy to the patient via the plurality of contact points; a controller operatively coupled to the plurality of electrodes and configured to control electrical current that passes through the plurality of electrodes during delivery of the bio-electric microcurrent stimulation therapy; and a pressure device configured to control a contact pressure of the plurality of electrodes at the plurality of contact points.

In some embodiments, the apparatus further includes at least a first ground electrode coupled to the head-mounted device and configured to be placed at a ground location on the patient. In some embodiments, the head-mounted device includes a display configured to present information related to the bio-electric microcurrent stimulation therapy. In some embodiments, the head-mounted device includes a plurality of light-emitting-diodes (LEDs) configured to provide light signals that provide information related to the bio-electric microcurrent stimulation therapy. In some embodiments, the head-mounted device includes at least a first haptic vibration device configured to provide vibration that provides information related to the bio-electric microcurrent stimulation therapy. In some embodiments, the plurality of electrodes is part of at least a first disposable chip-electrode-array circuit. In some embodiments, the plurality of electrodes is part of at least a first disposable chip-electrode-array circuit on a flexible substrate, wherein the flexible substrate further includes an adhesive layer and electrically conductive gel. In some embodiments, the controller is built into the head-mounted device. In some embodiments, the controller is located separately from the head-mounted device and is wirelessly coupled to the head-mounted device.

In some embodiments of the apparatus, the plurality of electrodes is part of at least a first disposable chip-electrode-array circuit that includes a unique serial number (USN) that identifies the at least first disposable chip-electrode-array circuit and allows encrypted communications between the controller and a remote server that contains medical and therapy information associated with the patient. In some embodiments, the apparatus further includes sensors operatively coupled to the controller and configured to provide feedback related to the bio-electric microcurrent stimulation therapy.

In some embodiments of the apparatus, the pressure device includes a lens cover coupled to the head-mounted device and configured to contact the plurality of electrodes to apply pressure between the plurality of electrodes and the plurality of contact points. In some embodiments, the pressure device includes a lens cover coupled to the head-mounted device and configured to contact the plurality of electrodes to apply pressure between the plurality of electrodes and the plurality of contact points, wherein the lens cover is spring-mounted such that the lens cover is configured to flip between a first position that contacts the plurality of electrodes and a second position that is not in contact with the plurality of electrodes. In some embodiments, the pressure device includes a lens cover coupled to the head-mounted device and configured to contact the plurality of electrodes to apply pressure between the plurality of electrodes and the plurality of contact points, the apparatus further including sensors operatively coupled to the controller and configured to provide feedback related to the bio-electric microcurrent stimulation therapy.

In some embodiments, the present invention provides a method for applying bio-electric microcurrent stimulation therapy to a patient via a disposable chip-electrode-array circuit that connects to a micro-stimulation current generating head-mounted device, the method including mounting the head-mounted device to the patient's head; applying one or more electrode strips of the disposable chip-electrode-array circuit to a plurality of contact points on the patient's skin; connecting the one or more electrode strips to the head-mounted device; controlling electrical current that passes through the one or more electrode strips during delivery of the bio-electric microcurrent stimulation therapy; and controlling a contact pressure of the one or more electrode strips at the plurality of contact points.

In some embodiments, the method further includes providing a first ground electrode; coupling the first ground electrode to the head-mounted device; and placing the first ground electrode at a ground location on the patient. In some embodiments, the method further includes displaying information related to the bio-electric microcurrent stimulation therapy. In some embodiments, the head-mounted device includes a plurality of light-emitting-diodes (LEDs), the method further including generating light signals using the plurality of LEDs in order to provide information related to the bio-electric microcurrent stimulation therapy. In some embodiments, the head-mounted device includes at least a first haptic vibration device, the method further including generating vibration signals using the at least first haptic vibration device in order to provide information related to the bio-electric microcurrent stimulation therapy.

In some embodiments, the method further includes providing a flexible substrate that includes an adhesive layer and electrically conductive gel; and mounting the at least a first disposable chip-electrode-array circuit on the flexible substrate. In some embodiments, the controlling of the electrical current occurs within the head-mounted device. In some embodiments, the controlling of the electrical current occurs remote from the head-mounted device. In some embodiments, the disposable chip-electrode-array circuit includes a unique serial number (USN) that identifies the disposable chip-electrode-array circuit for a remote server that contains medical and therapy information associated with the patient, wherein the controlling of the electrical current includes transmitting and receiving encrypted communications between the head-mounted device and the remote server.

In some embodiments, the method further includes providing one or more sensors operatively coupled to the head-mounted device, wherein the controlling of the electrical current includes receiving feedback from the one or more sensors during the applying of the bio-electric microcurrent stimulation therapy. In some embodiments, the method further includes providing a lens cover coupled to the head-mounted device, wherein the controlling of the contact pressure of the one or more electrode strips includes pushing the lens cover into the one or more electrode strips to apply pressure between the plurality of electrodes and the plurality of contact points. In some embodiments, the method further includes providing a lens cover coupled to the head-mounted device, wherein the controlling of the contact pressure of the one or more electrode strips includes flipping the lens cover between a first position that contacts the one or more electrode strips and a second position that is not in contact with the one or more electrode strips. In some embodiments, the method further includes providing a lens cover coupled to the head-mounted device, wherein the controlling of the contact pressure of the one or more electrode strips includes flipping the lens cover between a first position that contacts the one or more electrode strips and a second position that is not in contact with the one or more electrode strips; and providing one or more sensors operatively coupled to the head-mounted device, wherein the controlling of the electrical current includes receiving feedback from the one or more sensors during the applying of the bio-electric microcurrent stimulation therapy.

In some embodiments, the present invention provides a system for applying stimulation therapy to a patient, wherein the patient has a first eye and a second eye, and wherein the first eye and the second eye each include an upper eyelid and a lower eyelid, the system including a first stimulation strip that includes a first elongated portion configured to be placed on the upper eyelid of the first eye of the patient and a second elongated portion configured to be placed on the lower eyelid of the first eye of the patient, wherein the first stimulation strip includes: a first plurality of individually controlled electrodes, wherein the first plurality of individually controlled electrodes is configured to deliver therapy that includes a sequence or series of spatially and temporally separated microcurrent stimulation of varied pulsed intensity (e.g., wherein "intensity" means pulses of a given current level) to the patient's first eye, and a first plurality of light emitters, wherein the first plurality of light emitters is configured to deliver a sequence or series of spatially and temporally separated light-stimulation therapy of varied intensity (e.g., pulses) to the patient; and a controller operatively coupled to the first bifurcated stimulation strip and configured to control delivery of the microcurrent stimulation therapy and the light stimulation therapy.

In some embodiments, the "pulsed" electrical stimulation from a first electrode to a second electrode includes both positive-voltage pulses alternated with negative-voltage pulses in order to avoid charge buildup in the tissue. For example, in some embodiments, a single pulse in a positive-voltage direction is followed by a single pulse in a negative-voltage direction, wherein the amplitude and duration of the positive-voltage direction pulse and the amplitude and duration of the negative-voltage direction pulse are each selected so that one offsets the other to avoid charge buildup in the cells in the electrical path between the first electrode and the second electrode. In other embodiments, one or more pulses in the positive-voltage direction are followed by one or more pulses in a negative-voltage direction. In yet other embodiments, the stimulation includes an alternating current (AC) waveform that is amplitude modulated by gating pulses such that a plurality of the AC cycles are passed by the amplitude modulated gating pulses.

In some embodiments of the system, each respective electrode of the first plurality of electrodes contacts the patient at a respective contact pressure, the system further including a pressure-control device coupled to the first bifurcated strip and configured to selectively maintain the respective contact pressure of each respective electrode in a range of two (2) ounces per square inch (about 0.862 kilopascals) to fifteen (15) pounds per square inch (about 103.4 kilopascals). In some embodiments, each respective electrode of the first plurality of electrodes contacts the patient at a respective contact point and at a respective contact pressure, the system further including a pressure-control device coupled to the first bifurcated strip and configured to selectively maintain the respective contact pressure of each respective electrode in a range of two (2) ounces per square inch (0.862 kilopascals) to fifteen (15) pounds per square inch (103.4 kilopascals), wherein the pressure-control device is configured to provide a negative pressure such that skin of the respective contact point is pulled toward the respective electrode.

In some embodiments of the system, the controller is configured to control the first plurality of electrodes and the first plurality of light emitters such that the microcurrent stimulation therapy is delivered simultaneously with the delivery of the light stimulation therapy. In some embodiments, the controller is configured to control the first plurality of electrodes and the first plurality of light emitters such that the microcurrent stimulation therapy is delivered during a first time period and the light stimulation therapy is delivered during a second time period that follows the first time period.

In some embodiments, the present invention provides a system for applying stimulation therapy to a patient, wherein the patient has a first eye and a second eye, and wherein the first eye and the second eye each include an upper eyelid and a lower eyelid, the system including a first bifurcated stimulation strip that includes a first elongated portion configured to be placed on the upper eyelid of the first eye of the patient and a second elongated portion configured to be placed on the lower eyelid of the first eye of the patient, wherein the first bifurcated stimulation strip includes: a first plurality of electrodes, wherein a first sub-plurality of the first plurality of electrodes is configured to deliver a microcurrent stimulation therapy to the patient, and wherein a second sub-plurality of the first plurality of electrodes is configured to deliver a heat therapy to the patient; and a controller operatively coupled to the first bifurcated stimulation strip and configured to control delivery of the microcurrent stimulation therapy and the heat therapy.

In some embodiments of the system, the controller is configured to control the first plurality of electrodes such that the microcurrent stimulation therapy is delivered simultaneously with the delivery of the heat therapy. In some embodiments, the controller is configured to control the first plurality of electrodes such that the heat therapy is delivered during a first time period and the microcurrent stimulation therapy is delivered during a second timer period that follows the first time period. In some embodiments, the controller is configured to control the first sub-plurality of the first plurality of electrodes such that the microcurrent stimulation therapy is delivered via a continuous microcurrent. In some embodiments, the controller is configured to control the first sub-plurality of the first plurality of electrodes such that the microcurrent stimulation therapy is delivered via a pulsed microcurrent.

In some embodiments, the present invention provides a system for applying stimulation therapy to a patient, wherein the patient has a first eye and a second eye, and wherein the first eye and the second eye each include an upper eyelid and a lower eyelid, the system including a first bifurcated stimulation strip that includes a first elongated portion configured to be placed on the upper eyelid of the first eye of the patient and a second elongated portion configured to be placed on the lower eyelid of the first eye of the patient, wherein the first bifurcated stimulation strip includes: a plurality of electrodes, wherein the plurality of electrodes is configured to deliver a microcurrent stimulation therapy to the patient, and a plurality of light emitters, wherein the plurality of light emitters is configured to deliver light stimulation therapy to the patient, and wherein the first bifurcated stimulation strip is further configured to deliver a heat therapy to the patient; and a controller operatively coupled to the first bifurcated stimulation strip and configured to control delivery of the microcurrent stimulation therapy, the heat therapy, and the light stimulation therapy.

In some embodiments, the present invention provides a system for applying stimulation therapy to a patient, wherein the patient has a first eye and a second eye, and wherein the first eye and the second eye each include an upper eyelid and a lower eyelid, the system including: a first stimulation strip that includes a first elongated portion configured to be placed on the upper eyelid of the first eye of the patient and a second elongated portion configured to be placed on the lower eyelid of the first eye of the patient, wherein the first stimulation strip includes: a first plurality of individually controlled electrodes, wherein the first plurality of individually controlled electrodes is configured to deliver microcurrent stimulation therapy to the patient's first eye, and a first plurality of individually controlled light emitters, wherein the first plurality of individually controlled light emitters is configured to deliver light-stimulation therapy to the patient's first eye; and a controller operatively coupled to the first stimulation strip and configured to control delivery of the microcurrent stimulation therapy and the light stimulation therapy to the patient's first eye.

In some embodiments of the system, each respective electrode of the first plurality of electrodes contacts the patient at a respective contact pressure, the system further including: a pressure-control device coupled to the first strip and configured to selectively maintain the respective contact pressure of each respective electrode at a value in a range of two (2) ounces per square inch (0.862 kilopascals) to fifteen (15) pounds per square inch (103.4 kilopascals), inclusive, which, in some embodiments, is delivered to a "pinpointed" area for each electrode of, for example, 2 to 225 square millimeters (1.4 mm*1.4 mm=2 mm² to 15 mm*15 mm=225 mm²). In some embodiments, the respective incremental contact pressure (in addition to normal atmospheric pressure of air on the skin) of each respective electrode is selectively maintained at a value of three (3) ounces per square inch (1.29 kilopascals), four (4) ounces per square inch (1.72 kilopascals), five (5) ounces per square inch (2.15 kilopascals), ten (10) ounces per square inch (4.31 kilopascals), fifteen (15) ounces per square inch (6.46 kilopascals), one pound per square inch (6.89 kilopascals), two pounds per square inch (13.8 kilopascals), or any other suitable pressure value (in some such embodiments, the pressure value is set such that an impedance associated with the delivery of the microcurrent stimulation therapy is eliminated or minimized). In some embodiments, the respective contact pressure of each respective electrode is maintained at a value in a range of two (2) ounces per square inch (0.862 kilopascals) to one pound per square inch (6.89 kilopascals), inclusive; a range of eight (8) ounces per square inch (3.45 kilopascals) to one-and-a-half pounds per square inch (10.3 kilopascals), inclusive; a range of one (1) pound per square inch (6.89 kilopascals) to two pounds per square inch (13.8 kilopascals), inclusive, In some embodiments, the respective contact pressure of each respective electrode is individually maintained at a selected pressure value (e.g., in some embodiments, the contact pressure of a first respective electrode is maintained at a value of three (3) ounces per square inch (1.29 kilopascals) while the contact pressure of a second respective electrode is maintained at a value of four (4) ounces per square inch (1.72 kilopascals)).

In some embodiments, each respective electrode of the first plurality of electrodes contacts the patient at a respective contact point and at a respective contact pressure, the system further including a pressure-control device coupled to the first strip and configured to selectively maintain the respective contact pressure of each respective electrode in a range of two (2) ounces per square inch (0.862 kilopascals) to fifteen (15) pounds per square inch (103.4 kilopascals), wherein the pressure-control device generates the respective contact pressure by creating a vacuum such that skin of the respective contact point is pulled toward the respective electrode.

In some embodiments of the system, the controller is configured to control the first plurality of electrodes and the first plurality of light emitters such that the microcurrent stimulation therapy is delivered simultaneously with the delivery of the light stimulation therapy (e.g., in a manner such as described in U.S. Pat. No. 8,160,696, which is incorporated by reference above). In some embodiments, the controller is configured to control the first plurality of electrodes and the first plurality of light emitters such that the microcurrent stimulation therapy is delivered during a first time period and the light-stimulation therapy is delivered during a second timer period that follows the first time period (e.g., in a manner such as described in U.S. Pat. No. 8,160,696, which is incorporated by reference above).

In some embodiments of the system, the first plurality of electrodes includes a single-use, disposable electrode-strip housing that contains a respective gelled contact point for each respective one of the first plurality of electrodes, wherein the electrode-strip housing is configured to removably couple to the first plurality of electrodes (e.g., the electrode-strip housing snaps into the first plurality of electrodes), and wherein the electrode-strip housing includes a peel-off cover that is removed to expose each respective gelled contact point.

In some embodiments of the system, the first stimulation strip is coupled to a headset device configured to be placed on a head of the patient, wherein the first plurality of electrodes is part of a disposable (e.g., single use) housing that includes a respective gelled contact point for each respective one of the first plurality of electrodes, wherein the housing is configured to removably couple to the headset device, and wherein the housing includes a peel-off cover that is removed to expose each respective gelled contact point.

In some embodiments, the system further includes a stimulator signal generator operatively coupled to the first plurality of individually controlled electrodes and configured to generate the microcurrent stimulation therapy signals delivered by the first plurality of individually controlled electrodes. In some such embodiments, the stimulator signal generator is placed on (or near) a temple of the patient. In some embodiments, the microcurrent stimulation therapy includes a series of spatially and temporally separated microcurrent pulses. In some embodiments, the light-stimulation therapy includes a series of spatially and temporally separated light pulses.

In some embodiments, the system further includes an audio-output unit configured to provide a sound (beep, chime, ding, or the like) to indicate a characteristic of the microcurrent stimulation therapy (and/or the light-stimulation therapy) (e.g., indicate that the microcurrent stimulation therapy has started/ended, indicate that the microcurrent stimulation therapy is malfunctioning, and the like).

In some embodiments, the system further includes: a second stimulation strip that includes a first elongated portion configured to be placed on the upper eyelid of the second eye of the patient and a second elongated portion configured to be placed on the lower eyelid of the second eye of the patient, wherein the second stimulation strip includes: a second plurality of individually controlled electrodes, wherein the second plurality of individually controlled electrodes is configured to deliver microcurrent stimulation therapy to the patient's second eye, and a second plurality of individually controlled light emitters, wherein the second plurality of individually controlled light emitters is configured to deliver light-stimulation therapy to the patient's second eye; wherein the controller is operatively coupled to the second stimulation strip and the controller is further configured to control delivery of the microcurrent stimulation therapy and the light stimulation therapy to the patient's second eye. In some embodiments, at least one selected from the group consisting of microcurrent stimulation therapy and light-stimulation therapy is delivered to the patient's first eye and the patient's second eye simultaneously. In some embodiments, at least one selected from the group consisting of microcurrent stimulation therapy and light-stimulation therapy is delivered to the patient's first eye during a first time period, wherein at least one selected from the group consisting of microcurrent stimulation therapy and light-stimulation therapy is delivered to the patient's second eye during a second time period, and wherein the second time period occurs after the first time period.

In some embodiments of the system, the light-stimulation therapy is delivered as a continuous wave of light energy. In some embodiments, the light-stimulation therapy is delivered as a plurality of light pulses. In some embodiments, at least one selected from the group consisting of the microcurrent therapy and the light-stimulation therapy is delivered in a plurality of cycles, wherein each pair of sequential cycles within the plurality of cycles is separated by a rest period (e.g., a rest period in a range of 60 seconds to ten (10) minutes). In some embodiments, the first stimulation strip further includes a ground electrode operatively coupled to the first plurality of electrodes and configured to be placed on the patient (e.g., on or near the eyelids or other location on the head, neck, shoulder, chest, or any other suitable part of the patient). In some embodiments, the first stimulation strip is coupled to a headset device configured to be placed on a head of the patient. In some embodiments, the first stimulation strip is coupled to a headset device configured to be placed on a head of the patient, and wherein the headset device includes the controller. In some embodiments, the first stimulation strip includes a microchip, and wherein the controller communicates wirelessly with the microchip. In some embodiments, the first plurality of electrodes is coupled to the controller via a three-layer wiring, and wherein the three-layer wiring includes an interference-blocking layer.

In some embodiments, the present invention provides a system for applying stimulation therapy to a patient, wherein the patient has a first eye and a second eye, and wherein the first eye and the second eye each include an upper eyelid and a lower eyelid, the system including: a first stimulation strip that includes a first elongated portion configured to be placed on the upper eyelid of the first eye of the patient and a second elongated portion configured to be placed on the lower eyelid of the first eye of the patient, wherein the first stimulation strip includes: a first plurality of individually controlled electrodes configured to deliver microcurrent stimulation therapy to the patient's first eye, a first plurality of individually controlled heat sources configured to deliver heat therapy to the patient's first eye; and a controller operatively coupled to the first stimulation strip and configured to control delivery of the microcurrent stimulation therapy and the heat therapy to the patient's first eye. In some embodiments, the controller is configured to control the first plurality of electrodes such that the microcurrent stimulation therapy is delivered simultaneously with the delivery of the heat therapy. In some embodiments, the heat therapy is delivered during a first time period and the microcurrent stimulation therapy is delivered during a second timer period that follows the first time period. In some embodiments, the controller is configured to control the first plurality of electrodes such that the microcurrent stimulation therapy is delivered via a continuous microcurrent. In some embodiments, the controller is configured to control the first plurality of electrodes such that the microcurrent stimulation therapy is delivered via a pulsed microcurrent. In some embodiments, the system further includes a trans-cranial magnetic pulse generator operatively coupled to the controller and configured to provide pulsed electromagnetic field (PEMF) therapy to the patient (e.g., eyelids or other areas near the first and/or second eye of the patient). In some embodiments, the first plurality of individually controlled electrodes is further configured to provide high voltage pulsed current (HVPC) therapy to the patient (e.g., the first and/or second eye of the patient). In some embodiments, the first plurality of individually controlled electrodes is further configured to provide low voltage pulsed current (LVPC) therapy to the patient (e.g., the first and/or second eye of the patient).

In some embodiments of the system, the first plurality of heat sources includes a plurality of electrically-driven heat elements. In some embodiments of the system, the first plurality of heat sources includes a dual heat sourced electrode that can individually activate heat at either one or more of the upper-eyelid electrode(s) or one or more of the bottom eyelid electrode(s), or activate both upper and lower simultaneously. In some embodiments, the microcurrent stimulation therapy is delivered simultaneously with the delivery of the heat therapy. In some embodiments, the heat therapy is delivered during a first time period, wherein the microcurrent stimulation therapy is delivered during a second time period, and wherein the second time period occurs after the first time period.

In some embodiments, the system further includes a second stimulation strip that includes a first elongated portion configured to be placed on the upper eyelid of the second eye of the patient and a second elongated portion configured to be placed on the lower eyelid of the second eye of the patient, wherein the second stimulation strip includes: a second plurality of individually controlled electrodes, wherein the second plurality of individually controlled electrodes is configured to deliver microcurrent stimulation therapy to the patient's second eye, and a second plurality of individually controlled heat sources configured to deliver a heat therapy to the patient's second eye; wherein the controller is operatively coupled to the second stimulation strip and the controller is further configured to control delivery of the microcurrent stimulation therapy and the heat therapy to the patient's second eye.

In some embodiments of the system, at least one selected from the group consisting of microcurrent stimulation therapy and heat therapy is delivered to the patient's first eye and the patient's second eye simultaneously. In some embodiments, at least one selected from the group consisting of microcurrent stimulation therapy and heat therapy is delivered to the patient's first eye during a first time period, wherein at least one selected from the group consisting of microcurrent stimulation therapy and heat therapy is delivered to the patient's second eye during a second time period, and wherein the second time period occurs after the first time period.

In some embodiments, the heat therapy is configured to increase blood flow to the back of the patient's first eye (and blood temperature to the eye region), and in some embodiments, the heat therapy is delivered to change the temperature of the tissue of the patient to achieve a tissue temperature value in a range of approximately 36.6 degrees Celsius (98 degrees Fahrenheit) to approximately 43 degrees Celsius (approximately 109.4 degrees Fahrenheit), inclusive, and for a therapy time period in a range from one (1) second to thirty (30) minutes, inclusive. For example, in some embodiments, a therapy time period of 30 seconds, 60 seconds, two minutes, five minutes, 10 minutes, 20 minutes, 30 minutes, or any other suitable time period). In some embodiments, the heat therapy is delivered at a temperature value in a range of approximately 36.6 degrees Celsius (98 degrees Fahrenheit) to approximately 48.9 degrees Celsius (approximately 120 degrees Fahrenheit), inclusive. In some embodiments, the heat therapy is applied in a controlled temperature-change-per-unit-time manner to prevent thermal shock that might damage tissue or cause discomfort to the patient. In some embodiments, the rate of temperature rise (or fall) is maintained at a rate of no more than one degree Celsius per 10 seconds, a rate of no more than one degree Celsius per 20 seconds, a rate of no more than one degree Celsius per 30 seconds, a rate of no more than one degree Celsius per 40 seconds, a rate of no more than one degree Celsius per 50 seconds, or a rate of no more than one degree Celsius per 60 seconds. In some such embodiments, the rate of change of temperature is varied as the temperature is raised or lowered. In some such embodiments, a temperature sensor is used to obtain temperature parameters at the stimulation strip, and the controller adjusts the current supplied to the resistive heaters on the stimulation strip to control the rate of temperature change, in a manner modified from whole-body hyperthermia methods such as described in U.S. Pat. No. 5,730,720 to Sites et al., but rather than perfusing blood or other fluid into the patient as described by Sites et al., the present invention applies heat at a controlled rate to the outer skin of the patient via resistive or other heat-generation devices on the stimulation strip or on the goggle-like devices that press the stimulation strip against the skin of the patient. In other embodiments, a thermo-electric cooler (such as a Peltier device) is used to cool the skin at the electrode locations, and in some such embodiments, the present invention applies cooling at a controlled rate, and then at the end of the therapy session, raises the temperature at a controlled rate.

In some embodiments, the first stimulation strip includes one or more temperature sensors configured to sense a temperature of the patient's tissue at the contact point of the heat (or cooling) source such that the heat therapy is delivered based on the sensed temperature of the patient's tissue at the contact point. In some embodiments, the heat therapy is delivered such that the sensed temperature of the patient's tissue at the contact point is approximately 37 degrees Celsius, approximately 37.5 degrees Celsius, approximately 38 degrees Celsius, approximately 38.5 degrees Celsius, approximately 39 degrees Celsius, approximately 39.5 degrees Celsius, approximately 40 degrees Celsius, approximately 41 degrees Celsius, approximately 42 degrees Celsius, approximately 42.5 degrees Celsius, or any other suitable temperature. In some embodiments, the temperature is kept at or below 43 degrees Celsius to avoid thermal damage to the tissue. In some embodiments, the temperature rate of change is kept at or below one degree Celsius per 20 seconds to avoid thermal-shock damage to the tissue or discomfort to the patient. In some embodiments, each respective electrode of the first plurality of electrodes contacts the patient at a respective contact point, wherein the first plurality of heat sources includes a first heat source located at a first respective contact point and a second heat source located at a second respective contact point, wherein the heat therapy includes delivery of heat for a first time period via the first heat source, and delivery of heat for a second time period via the second heat source. In some embodiments, each of the first plurality of heat sources is configured to deliver the heat therapy simultaneously such that a majority portion of the first stimulation strip is heated during delivery of the heat therapy.

In some embodiments of the system, at least one selected from the group consisting of the microcurrent therapy and the heat therapy is delivered in a plurality of cycles, wherein each pair of sequential cycles within the plurality of cycles is separated by a rest period (e.g., a rest period in a range of 60 seconds to ten (10) minutes, inclusive; in some embodiments, a rest period of 90 seconds, a rest period of 120 seconds, a rest period of 180 seconds, a rest period of 240 seconds, a rest period of five minutes, a rest period of six minutes, a rest period of seven minutes, a rest period of eight minutes, a rest period of nine minutes, a rest period of ten minutes, or any other suitable rest period between each therapy time period). In some embodiments, the first stimulation strip further includes a ground electrode operatively coupled to the first plurality of electrodes and configured to be placed on a head of the patient. In some embodiments, the first stimulation strip is coupled to a headset device configured to be placed on a head of the patient. In some embodiments, the first stimulation strip is coupled to a headset device configured to be placed on a head of the patient, and wherein the headset device includes the controller. In some embodiments, the first stimulation strip includes a microchip, wherein the controller communicates wirelessly with the microchip.

In some embodiments, the present invention provides a system for applying stimulation therapy to a patient, wherein the patient has a first eye and a second eye, and wherein the first eye and the second eye each include an upper eyelid and a lower eyelid, the system including a first stimulation strip that includes a first elongated portion configured to be placed on the upper eyelid of the first eye of the patient and a second elongated portion configured to be placed on the lower eyelid of the first eye of the patient, wherein the first stimulation strip includes: a first plurality of individually controlled electrodes, wherein the first plurality of electrodes is configured to deliver a microcurrent stimulation therapy to the patient's first eye, and a first plurality of individually controlled light emitters, wherein the first plurality of light emitters is configured to deliver light-stimulation therapy to the patient's first eye, a first plurality of individually controlled heat sources configured to deliver heat therapy to the patient's first eye; and a controller operatively coupled to the first stimulation strip and configured to control delivery of the microcurrent stimulation therapy, the light-stimulation therapy, and the heat therapy to the patient's first eye.

In some embodiments of the system, the microcurrent stimulation therapy, the light-stimulation therapy, and the heat therapy are delivered simultaneously. In some embodiments, the microcurrent stimulation therapy is delivered during a first time period, wherein the light-stimulation therapy is delivered during a second time period, and wherein the heat therapy is delivered during a third time period.

In some embodiments, the system further includes: a second stimulation strip that includes a first elongated portion configured to be placed on the upper eyelid of the second eye of the patient and a second elongated portion configured to be placed on the lower eyelid of the second eye of the patient, wherein the second stimulation strip includes: a second plurality of individually controlled electrodes, wherein the second plurality of individually controlled electrodes is configured to deliver microcurrent stimulation therapy to the patient's second eye, and a second plurality of individually controlled light emitters, wherein the second plurality of individually controlled light emitters is configured to deliver light-stimulation therapy to the patient's second eye, a second plurality of individually controlled heat sources configured to deliver heat therapy to the patient's second eye; wherein the controller is operatively coupled to the second stimulation strip and the controller is further configured to control delivery of the microcurrent stimulation therapy, the light-stimulation therapy, and the heat therapy to the patient's second eye. In some embodiments, at least one selected from the group consisting of microcurrent stimulation therapy, light-stimulation therapy, and heat therapy is delivered to the patient's first eye and the patient's second eye simultaneously. In some embodiments, at least one selected from the group consisting of microcurrent stimulation therapy, light-stimulation therapy, and heat therapy is delivered to the patient's first eye during a first time period, wherein at least one selected from the group consisting of microcurrent stimulation therapy, light-stimulation therapy, and heat therapy is delivered to the patient's second eye during a second time period, and wherein the second time period occurs after the first time period.

In some embodiments of the system, the heat therapy is configured to increase blood flow to the back of the patient's first eye, and wherein the heat therapy is delivered at a temperature in a range of approximately 36.6 degrees Celsius (98 degrees Fahrenheit) to approximately 43 degrees Celsius (approximately 109.4 degrees Fahrenheit) and for a time period in a range from one (1) second to thirty (30) minutes (e.g., in some embodiments, 30 seconds). In some embodiments, each respective electrode of the first plurality of electrodes contacts the patient at a respective contact point, wherein the first plurality of heat sources includes a first heat source located at a first respective contact point and a second heat source located at a second respective contact point, wherein the heat therapy includes delivery of heat for a first time period via the first heat source, and delivery of heat for a second time period via the second heat source. In some embodiments, each of the first plurality of heat sources is configured to deliver the heat therapy simultaneously such that a majority portion of the first stimulation strip is heated during delivery of the heat therapy.

In some embodiments, at least one selected from the group consisting of the microcurrent therapy, the light-stimulation therapy, and the heat therapy is delivered in a plurality of cycles, wherein each pair of sequential cycles within the plurality of cycles is separated by a rest period (e.g., a rest period in a range of 60 seconds to ten (10) minutes). In some embodiments, the light-stimulation therapy is delivered as a continuous wave of light energy. In some embodiments, the light-stimulation therapy is delivered as a plurality of light pulses. In some embodiments, the first stimulation strip further includes a ground electrode operatively coupled to the first plurality of electrodes and configured to be placed on a head of the patient. In some embodiments, the first stimulation strip is coupled to a headset device configured to be placed on a head of the patient. In some embodiments, the first stimulation strip is coupled to a headset device configured to be placed on a head of the patient, and wherein the headset device includes the controller. In some embodiments, the first stimulation strip includes a microchip, and wherein the controller communicates wirelessly with the microchip.

In some embodiments, the present invention provides a method for applying stimulation therapy to a patient, wherein the patient has a first eye and a second eye, and wherein the first eye and the second eye each include an upper eyelid and a lower eyelid, the method including: providing a first stimulation strip that includes a first elongated portion and a second elongated portion, and wherein the first stimulation strip includes a first plurality of individually controlled electrodes and a first plurality of individually controlled light emitters; placing the first elongated portion of the first stimulation strip on the upper eyelid of the first eye of the patient; placing the second elongated portion of the first stimulation strip on the lower eyelid of the first eye of the patient; delivering a microcurrent stimulation therapy to the patient's first eye via the first plurality of individually controlled electrodes; and delivering a light-stimulation therapy to the patient's first eye via the first plurality of individually controlled light emitters.

In some embodiments of the method, the delivering of the microcurrent stimulation therapy includes ramping up the microcurrent stimulation therapy from a first microcurrent level during a first time period to a second microcurrent level during a second time period that follows the first time period. In some embodiments, the delivering of the microcurrent stimulation therapy includes setting a level of the microcurrent stimulation therapy based on a tolerance of the patient, wherein the tolerance is determined (e.g., at the beginning of a treatment session) by gradually increasing an intensity of the microcurrent stimulation therapy (e.g., increasing the amplitude of current in each successive pulse or series of pulses at a rate that is gradual enough to allow the patient to respond to discomfort and indicate to stop the increase in intensity) until the patient provides feedback indicating that the microcurrent stimulation therapy has reached an discomfort threshold, and then decreasing the intensity of the microcurrent stimulation therapy until the patient provides feedback indicating that the microcurrent stimulation therapy is below the discomfort threshold, wherein the level of microcurrent stimulation therapy is set at the intensity that brings the patient below the discomfort threshold (in some embodiments, for example, the tolerance may vary from patient to patient, and the tolerance may vary from day to day for a given patient). In some embodiments, the delivering of the microcurrent stimulation therapy includes setting a level of the microcurrent stimulation therapy based on a tolerance of the patient, wherein the tolerance is determined by gradually increasing an intensity of the microcurrent stimulation therapy at a rate that allows the patient to respond to discomfort until the patient provides feedback indicating that the microcurrent stimulation therapy has reached a patient-indicated discomfort threshold, and then decreasing the intensity by a predetermined amount below the discomfort threshold (e.g., to a level of about 60%, 70%, 80%, or 90% of the intensity that resulted in the patient indicating discomfort), wherein the level of microcurrent stimulation therapy is set at the intensity that brings the patient below the discomfort threshold.

In some embodiments of the method, each respective electrode of the first plurality of electrodes contacts the patient at a respective contact pressure, the method further including selectively maintaining the respective contact pressure of each respective electrode at a value in a range of two (2) ounces per square inch (0.862 kilopascals) to fifteen (15) pounds per square inch (103.4 kilopascals). In some embodiments, the delivering of the microcurrent stimulation therapy and the delivering of the light-stimulation therapy occurs simultaneously. In some embodiments, the delivering of the microcurrent stimulation therapy occurs during a first time period, wherein the delivering of the light-stimulation therapy occurs during a second timer period that follows the first time period. In some embodiments, the delivering of the microcurrent stimulation therapy includes generating and delivering a series of spatially and temporally separated microcurrent pulses to the patient's first eye.

In some embodiments, the method further includes: providing a second stimulation strip that includes a first elongated portion and a second elongated portion, and wherein the second stimulation strip includes a second plurality of individually controlled electrodes and a second plurality of individually controlled light emitters; placing the first elongated portion of the second stimulation strip on the upper eyelid of the second eye of the patient; placing the second elongated portion of the second stimulation strip on the lower eyelid of the second eye of the patient; delivering a microcurrent stimulation therapy to the patient's second eye via the second plurality of individually controlled electrodes; and delivering a light-stimulation therapy to the patient's second eye via the second plurality of individually controlled light emitters. In some embodiments, the delivering of the microcurrent stimulation therapy to the patient's second eye occurs simultaneously with the delivering of the microcurrent stimulation therapy to the patient's first eye. In some embodiments, the delivering of the light-stimulation therapy includes generating and delivering a continuous wave of light energy to the patient's first eye. In some embodiments, the delivering of the light-stimulation therapy includes generating and delivering a plurality of light pulses to the patient's first eye.

In some embodiments of the method, the delivering of the microcurrent stimulation therapy and the delivering of the light-stimulation therapy includes delivering a plurality of stimulation cycles, wherein each pair of sequential cycles within the plurality of cycles is separated by a rest period (e.g., a rest period in a range of 60 seconds to ten (10) minutes).

In some embodiments, the present invention provides a method for applying stimulation therapy to a patient, wherein the patient has a first eye and a second eye, and wherein the first eye and the second eye each include an upper eyelid and a lower eyelid, the method including: providing a first stimulation strip that includes a first elongated portion and a second elongated portion, and wherein the first stimulation strip includes a first plurality of individually controlled electrodes and a first plurality of individually controlled heat sources; placing the first elongated portion of the first stimulation strip on the upper eyelid of the first eye of the patient; placing the second elongated portion of the first stimulation strip on the lower eyelid of the first eye of the patient; delivering a microcurrent stimulation therapy to the patient's first eye via the first plurality of individually controlled electrodes; and delivering a heat therapy to the patient's first eye via the first plurality of individually controlled light heat sources.

In some embodiments of the method, each respective electrode of the first plurality of electrodes contacts the patient at a respective contact pressure, the method further including: selectively maintaining the respective contact pressure of each respective electrode at a value in a range of two (2) ounces per square inch (0.862 kilopascals) to fifteen (15) pounds per square inch (103.4 kilopascals). In some embodiments, the delivering of the microcurrent stimulation therapy and the delivering of the heat therapy occurs simultaneously. In some embodiments, the delivering of the microcurrent stimulation therapy occurs during a first time period, and wherein the delivering of the heat therapy occurs during a second timer period that follows the first time period.

In some embodiments, the method further includes: providing a second stimulation strip that includes a first elongated portion and a second elongated portion, and wherein the second stimulation strip includes a second plurality of individually controlled electrodes and a second plurality of individually controlled heat sources; placing the first elongated portion of the second stimulation strip on the upper eyelid of the second eye of the patient; placing the second elongated portion of the second stimulation strip on the lower eyelid of the second eye of the patient; delivering a microcurrent stimulation therapy to the patient's second eye via the second plurality of individually controlled electrodes; and delivering a heat therapy to the patient's second eye via the second plurality of individually controlled heat sources. In some embodiments, the delivering of the microcurrent stimulation therapy to the patient's second eye occurs simultaneously with the delivering of the microcurrent stimulation therapy to the patient's first eye. In some embodiments, the heat therapy is configured to increase blood flow to the back of the patient's first eye, wherein the delivering of the heat therapy includes setting a temperature of the heat therapy at a temperature value in a range of approximately 36.6 degrees Celsius (98 degrees Fahrenheit) to approximately 43 degrees Celsius (approximately 109.4 degrees Fahrenheit) and for a time period in a range from one (1) second to thirty (30) minutes (e.g., in some embodiments, 30 seconds). In some embodiments, each respective electrode of the first plurality of electrodes contacts the patient at a respective contact point, wherein the first plurality of heat sources includes a first heat source located at a first respective contact point and a second heat source located at a second respective contact point, wherein the delivering of the heat therapy includes delivering heat for a first time period via the first heat source, and delivering heat for a second time period via the second heat source. In some embodiments, the delivering of the heat therapy includes delivering heat to the patient's first eye from each one of the first plurality of heat sources simultaneously.

In some embodiments, the present invention provides a method for applying stimulation therapy to a patient, wherein the patient has a first eye and a second eye, and wherein the first eye and the second eye each include an upper eyelid and a lower eyelid, the method including providing a first stimulation strip that includes a first elongated portion and a second elongated portion, and wherein the first stimulation strip includes a first plurality of individually controlled electrodes, a first plurality of individually controlled heat sources, and a first plurality of individually controlled light emitters; placing the first elongated portion of the first stimulation strip on the upper eyelid of the first eye of the patient; placing the second elongated portion of the first stimulation strip on the lower eyelid of the first eye of the patient; delivering a microcurrent stimulation therapy to the patient's first eye via the first plurality of individually controlled electrodes; delivering a heat therapy to the patient's first eye via the first plurality of individually controlled light heat sources; and delivering a light-stimulation therapy to the patient's first eye via the first plurality of individually controlled light emitters.

In some embodiments, the method further includes: providing a second stimulation strip that includes a first elongated portion and a second elongated portion, and wherein the second stimulation strip includes a second plurality of individually controlled electrodes, a second plurality of individually controlled heat sources, and a second plurality of light emitters; placing the first elongated portion of the second stimulation strip on the upper eyelid of the second eye of the patient; placing the second elongated portion of the second stimulation strip on the lower eyelid of the second eye of the patient; delivering a microcurrent stimulation therapy to the patient's second eye via the second plurality of individually controlled electrodes; delivering a heat therapy to the patient's second eye via the second plurality of individually controlled heat sources; and delivering a light-stimulation therapy to the patient's second eye via the second plurality of individually controlled light emitters. In some embodiments, the delivering of the microcurrent stimulation therapy to the patient's second eye occurs simultaneously with the delivering of the microcurrent stimulation therapy to the patient's first eye.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should be, therefore, determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

What is claimed is:

1. A system for application of a stimulation therapy to a patient, the system comprising:
   a first set of one or more light emitters, wherein each of the one or more light emitters are configured to deliver light-stimulation therapy to a first eye of the patient;
   a first substrate comprising one or more electrodes, wherein each of the one or more electrodes are configured to deliver microcurrent stimulation therapy to the first eye of the patient; and
   a controller configured to control delivery of the microcurrent stimulation therapy via the one or more electrodes of the first substrate and the light-stimulation therapy via the one or more light emitters of the first set to the first eye of the patient.

2. The system of claim 1, wherein each of the one or more electrodes are individually controllable by the controller.

3. The system of claim 1, further comprising a unique identifier on the substrate, and wherein the controller is configured to control a specific therapy regimen specified for the patient based on the unique identifier.

4. The system of claim 1, further comprising:
   a second set of one or more light emitters, wherein each of the one or more light emitters are configured to deliver light-stimulation therapy to a second eye of the patient; and
   a second substrate comprising second one or more electrodes, wherein each of the second one or more electrodes are configured to deliver microcurrent stimulation therapy to the second eye of the patient, and
   wherein the controller is further configured to control delivery of the microcurrent stimulation therapy via the second one or more electrodes of the second substrate and the light stimulation therapy via the one or more light emitters of the second set to the second eye of the patient.

5. The system of claim 4, wherein the controller is configured to cause delivery of the light-stimulation therapy and the microcurrent stimulation therapy to both the first eye and the second eye during the first time period.

6. The system of claim 4, wherein the controller is configured to cause delivery of the microcurrent stimulation therapy and the light-stimulation therapy in a sequential manner such that each stimulation therapy begins at a different start time to the first eye of the patient during a first time period and at a different start time to the second eye of the patient during a second time period after the first time period.

7. The system of claim 4, wherein the controller is configured to cause delivery of both the microcurrent stimulation therapy and the light-stimulation therapy alternately to the first eye of the patient and then to the second eye of the patient.

8. The system of claim 4, wherein the controller is configured to cause delivery of the microcurrent stimulation therapy alternately to the first eye of the patient and then to the second eye of the patient, and configured to cause delivery of the light-stimulation therapy alternately to the second eye and then to the first eye.

9. The system of claim 4, wherein the controller is configured to deliver the microcurrent stimulation therapy and the light-stimulation therapy simultaneously to both the first eye and the second eye of the patient during a first time period.

10. The system of claim 1, wherein each of the one or more electrodes includes a respective gelled contact point on the substrate.

11. The system of claim 1, wherein the first set of one or more light emitters is included in a head-mounted display device configured to be mounted on the patient's head, wherein the display device includes an internal stimulation display configured to be visible to the patient when the display device is mounted on the patient, and wherein the controller is configured to control delivery of the light-stimulation therapy from the display device.

12. The system of claim 11, wherein the light-stimulation therapy comprises red wavelengths in a range of 600 nm to 700 nm.

13. The system of claim 12, wherein the controller is further configured to control the display device to cause formation of one or more points of light that move across a visual field of the patient to urge the patient to move their eyes to follow the movement of the one or more points of light to orient eyes of the patient in different positions during the light-stimulation therapy.

14. The system of claim 1, wherein the first set of one or more light emitters is included on the first substrate.

15. The system of claim 1, wherein the light-stimulation therapy is delivered to both eyes of the patient simultaneously.

16. The system of claim 1, wherein the microcurrent stimulation therapy is delivered to both eyes of the patient simultaneously.

17. The system of claim 1, wherein the system is configured to deliver a combination of microcurrent stimulation therapy and light-stimulation therapy, wherein the microcurrent stimulation therapy is delivered to the patient in a sequential manner with the light-stimulation therapy such that each therapy begins at a different start time.

18. An apparatus for applying stimulation therapy to a patient, the apparatus comprising:
 a first set of one or more individually controlled light emitters;
 a first substrate, wherein the first substrate comprises a first plurality of individually controlled electrodes;
 means for delivering a first microcurrent stimulation therapy to the first eye of the patient via the first plurality of individually controlled electrodes; and
 means for delivering a first light-stimulation therapy to the first eye of the patient via the first set of one or more individually controlled light emitters.

19. A method for applying stimulation therapy to a patient, the method comprising:
 providing a first set of light emitters;
 providing a first substrate comprising one or more electrodes;
 delivering a first microcurrent stimulation therapy to a first eye of the patient via the one or more electrodes; and
 delivering a first light-stimulation therapy to the first eye of the patient via the first set of one or more light emitters.

20. The method of claim 19, wherein each respective electrode of the one or more electrodes contacts the patient at a respective contact pressure, the method further comprising:
 selectively maintaining the respective contact pressure of each respective electrode at a value in a range of about two (2) ounces per square inch to about fifteen (15) pounds per square inch.

21. The method of claim 19, further comprising delivering the first microcurrent stimulation therapy and the first light-stimulation therapy simultaneously.

22. The method of claim 19, further comprising:
 providing a stimulator configured to generate the microcurrent stimulation therapy delivered by the one or more electrodes;
 operatively coupling the stimulator to the one or more electrodes; and
 placing the stimulator on the patient.

23. The method of claim 19, further comprising:
 providing a stimulator configured to generate the microcurrent stimulation therapy delivered by the one or more electrodes;
 operatively coupling the stimulator to the one or more electrodes; and
 placing the stimulator in a location separate from the patient.

24. The method of claim 19, further comprising generating an indicative sound to indicate a characteristic of the first microcurrent stimulation therapy.

25. The method of claim 19, further comprising:
 providing a second set of one or more light emitters;
 providing a second substrate comprising a second one or more electrodes;
 delivering a second microcurrent stimulation therapy to a second eye of the patient via the second one or more electrodes; and
 delivering a second light-stimulation therapy to the second eye of the patient via the second set of one or more light emitters.

26. The method of claim 25, wherein the delivering of the first microcurrent stimulation therapy to the first eye occurs simultaneously with the delivering of the second microcurrent stimulation therapy to the second eye.

27. The method of claim 25, further comprising:
 receiving a unique identifier from the first substrate; and
 using the unique identifier by the controller to control a specific therapy regimen specified for the patient.

28. The method of claim 25, further comprising:
 providing a head-mounted display device configured to be placed on the patient's head, wherein the display device includes an internal stimulation display configured to be seen by the patient when the display device is on the patient; and
 delivering a light-stimulation output from the display device onto the patient's retina.

29. The method of claim 28, wherein the light-stimulation output includes red wavelengths in a range of 600 nm to 700 nm.

30. The method of claim 28, wherein delivering of the light-stimulation output includes moving one or more points of light across the patient's visual field to urge the patient to move their eyes to follow the movement of the one or more points of light to orient the eyes in different positions during the therapy.

* * * * *